US011111529B2

(12) United States Patent
Rondelez et al.

(10) Patent No.: US 11,111,529 B2
(45) Date of Patent: Sep. 7, 2021

(54) METHOD OF ELIMINATING BACKGROUND AMPLIFICATION OF NUCLEIC ACID TARGETS

(71) Applicants: THE UNIVERSITY OF TOKYO, Tokyo (JP); CENTRE NATIONAL DE LA RECHERCHE SCIENTIFIQUE (CNRS), Paris (FR)

(72) Inventors: Yannick Rondelez, Tokyo (JP); Guillaume Gines, Tokyo (JP); Kevin Montagne, Tokyo (JP); Teruo Fujii, Tokyo (JP)

(73) Assignees: THE FOUNDATION FOR THE PROMOTION OF INDUSTRIAL SCIENCE, Tokyo (JP); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 0 days.

(21) Appl. No.: 15/998,749

(22) PCT Filed: Feb. 16, 2017

(86) PCT No.: PCT/EP2017/053560
§ 371 (c)(1),
(2) Date: Aug. 16, 2018

(87) PCT Pub. No.: WO2017/140815
PCT Pub. Date: Aug. 24, 2017

(65) Prior Publication Data
US 2020/0149096 A1 May 14, 2020

(30) Foreign Application Priority Data

Feb. 16, 2016 (WO) .................. PCT/IB2016/000352

(51) Int. Cl.
*C12Q 1/68* (2018.01)
*C12Q 1/6844* (2018.01)
*C12Q 1/6876* (2018.01)

(52) U.S. Cl.
CPC ......... *C12Q 1/6844* (2013.01); *C12Q 1/6876* (2013.01)

(58) Field of Classification Search
CPC ....................................................... C12G 1/68
(Continued)

(56) References Cited

U.S. PATENT DOCUMENTS 8,071,308 B2 12/2011 Piepenburg et al.
9,121,046 B2 9/2015 Tanner et al.
(Continued)

FOREIGN PATENT DOCUMENTS

AU 2015202439 A1 6/2015
CN 104662159 A 5/2015
(Continued)

OTHER PUBLICATIONS

Baccouche et al., Dynamic DNA-toolbox reaction circuits: A walk-through, Methods, May 15, 2014;67(2):234-49. doi:10.1016/j.ymeth.2014.01.015. Epub Feb. 2, 2014.*

(Continued)

*Primary Examiner* — Aaron A Priest
(74) *Attorney, Agent, or Firm* — Foley & Lardner LLP; Sunit Talapatra

(57) ABSTRACT

An object is to provide a method of eliminating background amplification in detection of rare nucleic acids based on isothermal amplification. The method comprising steps of: preparing a mixture including solution and enzymes, and adding a first and a second template into the mixture, wherein the first template is an amplification template, and the second template is a leak absorption template. Methods (Continued)

to use this approach for multiplexed, ultrasensitive and ultra-specific detection of nucleic acids are presented.

20 Claims, 49 Drawing Sheets

Specification includes a Sequence Listing.

(58) Field of Classification Search
USPC .......................................................... 435/6.12
See application file for complete search history.

(56) References Cited

U.S. PATENT DOCUMENTS

| | | | |
|---|---|---|---|
| 2009/0081670 | A1 | 3/2009 | Maples et al. |
| 2011/0136104 | A1* | 6/2011 | Pregibon .............. C12Q 1/6851 435/6.12 |
| 2013/0012255 | A1 | 1/2013 | Kim et al. |
| 2013/0260422 | A1 | 10/2013 | Ong et al. |
| 2013/0323793 | A1 | 12/2013 | Tanner et al. |
| 2020/0172967 | A1* | 6/2020 | Gines ................... C12Q 1/6846 |

FOREIGN PATENT DOCUMENTS

| | | |
|---|---|---|
| WO | WO-02/057487 A2 | 7/2002 |
| WO | WO-2004/067726 A | 8/2004 |
| WO | WO-2009/012246 A | 1/2009 |

OTHER PUBLICATIONS

Aubert et al., Computer-assisted design for scaling up systems based on DNA reaction networks, J R Soc Interface. Apr. 6, 2014; 11(93): 20131167. doi: 10.1098/rsif.2013.1167.*

Milligan et al., Using RecA protein to enhance kinetic rates of DNA circuits, Chem Commun (Camb), Jun. 11, 2015;51(46):9503-6. doi: 10.1039/c5cc02261d.*

Xu Ying et al: "Ultrasensitive and rapid detection of miRNA with three-way junction structure-based trigger-assisted exponential enzymatic amplification", Biosensors and Bioelectronics, Elsevier BV, NL, vol. 81, Mar. 2, 2016 (Mar. 2, 2016), pp. 236-241, ISSN: 0956-5663, DOI: 10.1016/J.BIOS.2016.02.034.*

Baccouche, Alexandre et al., "Dynamic DNA-Toolbox Reaction Circuits: A walkthrough", Methods, (Feb. 2014).

Gasparic, Meti Buh et al., "Comparison of nine different real-time PCR chemistries for qualitative and quantitative applications in GMO detection", Anal Bioanal Chem 396, 2023-2029 (2010).

Ma, Cuiping et al., "Ultrasensitive detection of microRNAs based on hairpin fluorescence probe assisted isothermal amplification", Biosensors and Bioelectronics, vol. 58, pp. 57-60 (Aug. 2014).

Dang, Chinh et al., "Oligonucleotide Inhibitors of TaqDNA Polymerase Facilitate Detection of Low Copy Number Targets by PCR", 264, 268-27863 (1996).

Desbois, Linda et al.,: "A microfluidic device for on-chip agarose microbead generation with ultralow reagent consumption", Biomicrofluidics , vol. 6, No. 4, p. 44101 (2012).

Tan, Eric et al., "Isothermal DNA Amplification with Gold Nanosphere-Based Visual Colorimetric Readout for Herpes Simplex Virus Detection," Clinical Chemistry 53, No. 11 (Sep. 21, 2007).

Fukui, Kenji et al., "Simultaneous Use of MutS and RecA for Suppression of Nonspecific Amplification during PCR", Journal of Nucleic Acids, 1-5 (2013).

Guatelli, John C. et al., "Isothermal, in vitro amplification of nucleic acids by a multienzyme reaction modeled after retroviral replication," P Natl Acad Sci USA 87, 7797-1878 (1990).

Jia, Hongxia et al., "Ultrasensitive Detection of microRNAs by Exponential Isothermal Amplification," Angewandte Chemie International Edition 49, No. 32: 5498-5501(Jul. 26, 2010).

International Search Report issued in PCT/EP2017/053560, dated May 8, 2017.

Ye, Li-Ping et al., "Surface-Enhanced Raman Spectroscopy for Simultaneous Sensitive Detection of Multiple microRNAs in Lung Cancer Cells", Chemical Communications 50, No. 80: 11883-86 (Aug. 14, 2014).

Mitani, Yasumasa et al., "Rapid SNP diagnostics using asymmetric isothermal amplification and a new mismatch-suppression technology", Nat Meth 4, 257-262 (2007).

Ogata, Norio et al., "Creation of genetic information by DNA polymerase of the thermophilic bacterium *Thermus thermophiles*" Nucleic Acids Research 26(20):4657-4661(1998).

Padirac, Adrien et al., "Quencher-free multiplexed monitoring of DNA reaction circuits", Nucleic Acids Research 40, e118 (2012).

Piepenburg, Olaf et al., "DNA Detection Using Recombination Proteins" PLOS biology 4(7):e204 (2006).

Qian, Jifeng et al., "Sequence dependence of isothermal DNA amplification via EXPAR", Nucleic Acids Research 40(11):e87-e87 (2012).

Tan, Eric et al., "Isothermal DNA Amplification Coupled with DNA Nanosphere-Based Colorimetric Detection" Anal Chem 77(24):7984-7992 (2005).

Tan, Eric et al., "Specific versus Nonspecific Isothermal DNA Amplification through Thermophilic Polymerase and Nicking Enzyme Activities" Biochemistry 47(38):9987-9999 (2008).

Van Ness, Jeffrey et al., "Isothermal reactions for the amplification of oligonucleotides", P Natl Acad Sci USA 100(8):4504-4509 (Apr. 15, 2003).

Van Roekel, Hendrik W.H. et al., "Automated Design of Programmable Enzyme-Driven DNA Circuits", ACS Synthetic Biology (2014).

Walker, G. Terrance et al., "Isothermal in vitro amplification of DNA by a restriction enzyme/DNA polymerase system", P Natl Acad Sci USA 89(1):392 (1992).

Wang, Jianping et al., "Exponential amplification of DNA with very low background using graphene oxide and single-stranded binding protein to suppress non-specific amplification", Mikrochimica Acta, Springer Verlag, Vienna, AT, vol. 182, No. 5, pp. 1095-1101(Dec. 5, 2014).

Written Opinion of the International Searching Authority issued in PCT/EP2017/053560, dated May 8, 2017.

Zhang, Xiaobo et al., "Lab on a single microbead: an ultrasensitive detection strategy enabling microRNA analysis at the single-molecule level", Chemical Science 6, No. 11: 6213-18 (2015).

Xu, Ying et al., "Ultrasensitive and rapid detection of miRNA with three-way junction structure-based trigger-assisted exponential enzymatic amplification", Biosensors and Bioelectronics, Elsevier BV, NL, vol. 81, pp. 236-241(Mar. 2, 2016).

Yamagata, Atsushi et al., "Overexpression, purification and characterization of RecJ protein from Thermus thermophilus HB8 and its core domain", Nucleic Acids Research 29(22):4617 (2001).

Zhang, Kaixiang et al. "Digital quantification of miRNA directly in plasma using integrated comprehensive droplet digital detection", The Royal Society of Chemistry (2015).

Zhang, Yan et al., "Sensitive Detection of microRNA with Isothermal Amplification and a Single-Quantum-Dot-Based Nanosensor", Anal. Chem (2012).

* cited by examiner

\*\*\* Phosphorothioate modifications protecting against exonuclease
● 3' phosphate avoiding extension by the polymerase ① Incorporation of a pseudo-template (eliminates background amplification)
② Shortened autocatalytic template (removal of a few nucleotides)
③ Addition of an exonuclease (to avoid saturation)

F I G. 5

| Enzymes | Concentration |
|---|---|
| Bst2.0 WS | 4 u/mL |
| Nb.BsmI | 400 u/mL |
| ttRecJ | 25 nM |

| Oligonucleotides | |
|---|---|
| CBe12-2PS3 | 50 nM |
| pTBe12T5SP | various |

| Reaction buffer and condition | |
|---|---|
| Tris-HCL, pH 7.9 | 20 mM |
| $(NH_4)_2SO_4$ | 10 mM |
| KCl | 10 mM |
| $MgSO_4$ | 8.4 mM |
| NaCl | 50 mM |
| dithiothreitol | 3 mM |
| Symperonic F108 | 0.1% |
| BSA | 100 µg/mL |
| EvaGreen | 1x |
| Netropsin | 2 µM |
| dNTP | 50 µM each |
| Temperature | 45 °C |

FIG. 7

| Enzymes | Concentration |
|---|---|
| Bst2.0 WS | 4 u/mL |
| Nb.BsmI | 400 u/mL |
| ttRecJ | 25 nM |

| Oligonucleotides | |
|---|---|
| CBa12-2PS3 | 50 nM |
| decoy1 or decoy 2 | various |

| Reaction buffer and condition | |
|---|---|
| Tris-HCL, pH 7.9 | 20 mM |
| $(NH_4)_2SO_4$ | 10 mM |
| KCl | 10 mM |
| $MgSO_4$ | 8.4 mM |
| NaCl | 50 mM |
| dithiothreitol | 3 mM |
| Symperonic F108 | 0.1% |
| BSA | 100 µg/mL |
| EvaGreen | 1x |
| Netropsin | 2 µM |
| dNTP | 50 µM each |
| Temperature | 45 °C |

F I G. 9

| Enzymes | Concentration |
|---|---|
| Bst2.0 WS | 4 u/mL |
| Nb.BsmI | 400 u/mL |
| ttRecJ | 25 nM |

| Oligonucleotides | |
|---|---|
| various | 50 nM |
| various | various |

| Reaction buffer and condition | |
|---|---|
| Tris-HCL, pH 7.9 | 20 mM |
| $(NH_4)_2SO_4$ | 10 mM |
| KCl | 10 mM |
| $MgSO_4$ | 8.4 mM |
| NaCl | 50 mM |
| dithiothreitol | 3 mM |
| Symperonic F108 | 0.1% |
| BSA | 100 µg/mL |
| EvaGreen | 1x |
| Netropsin | 2 uM |
| dNTP | 50 uM each |
| Temperature | 45 °C |

FIG. 11

| Enzymes | Concentration |
|---|---|
| ttRecJ | 25 nM |
| Bst2.0 WS | 8 u/mL |
| Nt.BstNBI | 200 u/mL |
| Oligonucleotides | |
| Ck12-2PS4bioteg | 50 nM |
| Reaction buffer and condition | |
| Tris-HCL, pH 7.9 | 45 mM |
| $(NH_4)_2SO_4$ | 10 mM |
| NaCl | 50 mM |
| KCl | 10 mM |
| $MgSO_4$ | 5 mM |
| NaCl | 50 mM |
| Dithiothreitol | 3 mM |
| Symperonic F108 | 0.1% |
| BSA | 250 ug/mL |
| EvaGreen | 0.5x |
| Netropsin | 2 uM |
| dNTP | 50 uM |
| Temperature | 45C |

Ck12-2PS4bioteg = bioteg*C*A*A*TGACUCCTGCAATGACTCC-phos (SEQ ID NO: 33)

FIG. 13

| Enzymes | Concentration |
|---|---|
| ttRecJ | 25 nM |
| Bst full length | 50 u/mL |
| Nb.BsmI | 300 u/mL |

| Oligonucleotides | |
|---|---|
| CBa12-2biot3 | 100 nM |
| pTBa12A5SP | various |

| Reaction buffer and condition | |
|---|---|
| Tris-HCl, pH 7.9 | 20 mM |
| $(NH_4)_2SO_4$ | 10 mM |
| KCl | 10 mM |
| $MgSO_4$ | 8.4 mM |
| NaCl | 50 mM |
| dithiothreitol | 3 mM |
| Synperonic F108 | 0.1 % |
| BSA | 100 ug/mL |
| Streptavidin | 100 nM |
| Evagreen | 1x |
| Netropsin | 2 uM |
| dNTP | 30 uM |
| Temperature | 45 °C |

CBa12-2biot3 = C*T*C*G*TCAGAATGCTCGTCAGAATG bioteg  (SEQ ID NO: 34)
pTBa12A5SP = A*A*A*A*A- CTC GTC AGA ATG phos  (SEQ ID NO: 35)

FIG 14

| Enzymes | Concentration |
|---|---|
| ttRecJ | 25 nM |
| Vent(exo-) | 50 u/mL |
| Nb.BsmI | 400 u/mL |

| Oligonucleotides | |
|---|---|
| CBe12-2S4P | 50 nM |
| ApTBe12A3S3P | various |

| Reaction buffer and condition | |
|---|---|
| Tris-HCl, pH 7.9 | 20 mM |
| $(NH_4)_2SO_4$ | 10 mM |
| KCl | 10 mM |
| $MgSO_4$ | 8.4 mM |
| NaCl | 50 mM |
| dithiothreitol | 3 mM |
| Synperonic F108 | 0.1 % |
| BSA | 100 ug/mL |
| Evagreen | 1x |
| Netropsin | 2 uM |
| dNTP | 30 uM |
| Temperature | 50 °C |

CBe12-2S4P = C*G*A*T*CCTGAATG- CGATCCTGAA phos (SEQ ID NO: 36)
ApTBe12A3S3P = A*A*A - *CGA TCC TGA ATG phos (SEQ ID NO: 37)

FIG. 15

| Enzymes | Concentration |
|---|---|
| ttRecJ | 40 nM |
| Vent(exo-) | 50 u/mL |
| Nb.BsmI | 400 u/mL |

| Oligonucleotides | |
|---|---|
| CBe12-2noPS3 | 50 nM |
| ApTBe12A3S3P | various |

| Reaction buffer and condition | |
|---|---|
| Tris-HCl, pH 7.9 | 20 mM |
| $(NH_4)_2SO_4$ | 10 mM |
| KCl | 10 mM |
| $MgSO_4$ | 8.4 mM |
| NaCl | 50 mM |
| dithiothreitol | 3 mM |
| Synperonic F108 | 0.1 % |
| BSA | 100 ug/mL |
| Evagreen | 1x |
| Netropsin | 2 uM |
| dNTP | 30 uM |
| Temperature | 50 °C |

CBe12-2noPS3 = C*G*A*TCCTGAATGCGATCCTGAA  (SEQ ID NO: 38)
ApTBe12A3S3P = A*A*A - *CGATCCTGAATG phos  (SEQ ID NO: 37)

FIG. 16

| Enzymes | Concentration |
|---|---|
| ttRecJ | 25 nM |
| Vent(exo-) | 50 u/mL |
| Nt.BstNBI | 400 u/mL |

| Oligonucleotides | |
|---|---|
| Ck12-2S4noUbioteg | 50 nM |
| ApTK12A5S3P | various |

| Reaction buffer and condition | |
|---|---|
| Tris-HCl, pH 7.9 | 20 mM |
| $(NH_4)_2SO_4$ | 10 mM |
| KCl | 10 mM |
| $MgSO_4$ | 8.4 mM |
| NaCl | 50 mM |
| dithiothreitol | 3 mM |
| Synperonic F108 | 0.1 % |
| BSA | 100 ug/mL |
| Evagreen | 1x |
| Netropsin | 2 uM |
| dNTP | 30 uM |
| Temperature | 45 °C |

Ck12-2S4noUbioteg = bioteg CAATGACTCCTGCAATGACTCC phos (SEQ ID NO: 39)
ApTK12A5S3P = A*A*A*AA- CAATGACUCCTGA phos (SEQ ID NO: 40)

FIG. 19

| Enzymes | Concentration |
|---|---|
| ttrecJ | 25 nM |
| Vent exo- | 50 u/mL |
| Nt.BstNBI | 50 u/mL |
| Nb.BsmI | 400 u/mL |

| Oligonucleotides | |
|---|---|
| CBe12-2AULP | 50 nM |
| ApTBe12A3SP | 0 or 20 nM |
| D21tof5TBe12S3P | 0.1 nM |

| Reaction buffer and condition | |
|---|---|
| Tris-HCL, pH 7.9 | 20 mM |
| $(NH_4)_2SO_4$ | 10 mM |
| KCl | 10 mM |
| $MgSO_4$ | 8.4 mM |
| NaCl | 50 mM |
| dithiothreitol | 3 mM |
| Symperonic F108 | 0.1% |
| BSA | 100 µg/mL |
| EvaGreen | 1x |
| Netropsin | 2 µM |
| dNTP | 10 µM each |
| Temperature | 45 °C |

FIG. 22

| Enzymes | Concentration |
|---|---|
| ttRecJ | 25 nM |
| Vent exo- | 50 u/mL |
| Nt.BstNBI | 50 u/mL |
| Nb.BsmI | 400 u/mL |

| Oligonucleotides | |
|---|---|
| CBe12-3noPS3 | 100 nM |
| ApTBe12A3SP | 2.5 nM |
| D21toBe12S0P | 0.1 nM |

| Reaction buffer and condition | |
|---|---|
| Tris-HCl, pH 7.9 | 20 mM |
| $(NH_4)_2SO_4$ | 10 mM |
| KCl | 10 mM |
| $MgSO_4$ | 8.4 mM |
| NaCl | 50 mM |
| dithiothreitol | 3 mM |
| Symperonic F108 | 0.1% |
| BSA | 100 ug/mL |
| EvaGreen | 0.4 x |
| Netropsin | 2 uM |
| dNTP | 40 uM |
| Temperature | 50 °C |

CBe12-3noPS3 = C*T*C*G*TCAGAATG-CTCGTCAGA. (SEQ ID NO: 43)
ApTBe12A3SP = A*A*A*-CGATCCTGAATG-A-phos (SEQ ID NO: 37)
D21toBe12S0P = CGATCCTGAATG C-AA-TCAACATCAGTCTGATAAGCTA-phos (SEQ ID NO: 44)

FIG. 25
FIG. 25A  FIG. 25B
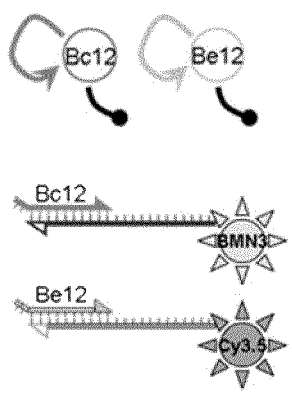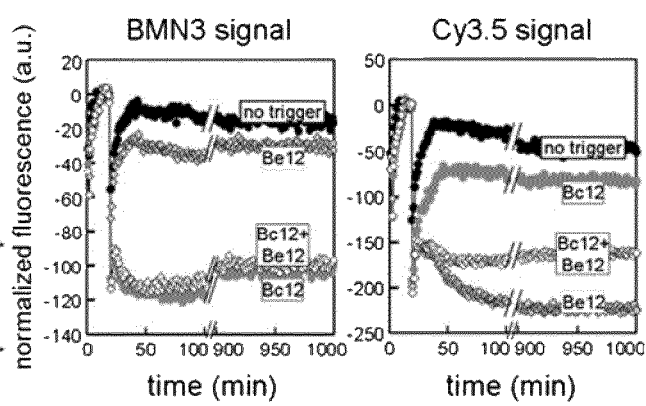

FIG. 26

| Enzymes | Concentration |
|---|---|
| ttRecJ | 25 nM |
| Bst2.0 WS | 4 u/mL |
| Nb.BsmI | 400 u/mL |
| Oligonucleotides | |
| CBe-2SPCy355 | 25 nM |
| CBc12-2SPBMN35 | 25 nM |
| pTBc12T5SP | 8 nM |
| pTBe12T5SP | 8 nM |
| Reaction buffer and condition | |
| Tris-HCL, pH 7.9 | 20 mM |
| $(NH_4)_2SO_4$ | 10 mM |
| KCl | 10 mM |
| $MgSO_4$ | 8.4 mM |
| NaCl | 50 mM |
| dithiothreitol | 3 mM |
| Symperonic F108 | 0.1% |
| BSA | 100 ug/mL |
| EvaGreen | 1x |
| Netropsin | 2 uM |
| dNTP | 50 uM |
| Temperature | 45C |

CBe12-2SPCy355 = Cy3.5*C*G*A*TCCTGAATG-CGATCCTGAA-phos  (SEQ ID NO: 45)
CBc12-2SPBMN35 = BMN3*C*A*G*TCCAGAATG-CAGTCCAGAA-phos  (SEQ ID NO: 46)
pTBc12T5SP  = T*T*T*T*T-CAGTCCAGAATG-phos  (SEQ ID NO: 47)
pTBe12T5SP = T*T*T*T*T-CGATCCTGAATG-phos  (SEQ ID NO: 5)

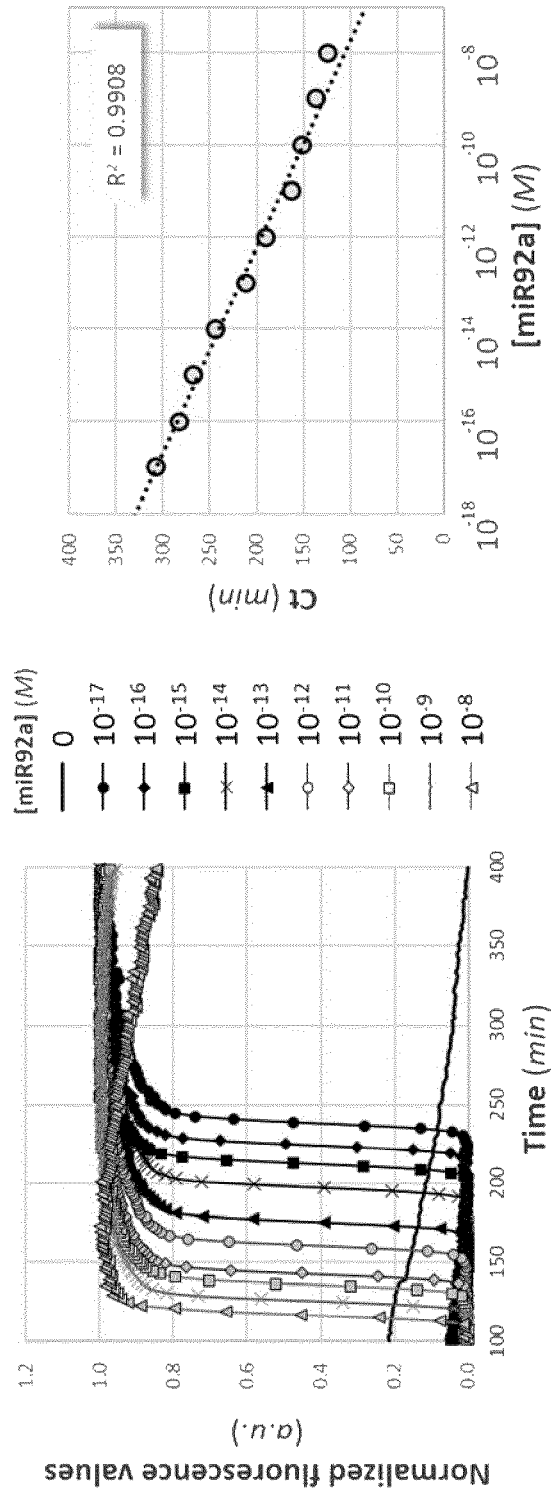

FIG. 28

| Enzymes | Concentration |
|---|---|
| Vent(exo-) | 50 u/mL |
| Nb.BsmI | 400 u/mL |
| Nt.BstNBI | 20 u/mL |
| ttRecJ | 37.5 nM |

| Oligonucleotides | |
|---|---|
| CBe12-3noPS3 | 100 nM |
| ApTBe12A3SP | 2.5 nM |
| 92atoF5TBe12PS0 | 0.1 nM |

| Reaction buffer and condition | |
|---|---|
| Tris-HCL, pH 7.9 | 20 mM |
| $(NH_4)_2SO_4$ | 10 mM |
| KCl | 10 mM |
| $MgSO_4$ | 8.4 mM |
| NaCl | 50 mM |
| dithiothreitol | 3 mM |
| Symperonic F108 | 0.1% |
| BSA | 100 µg/mL |
| EvaGreen | 1x |
| Netropsin | 2 µM |
| dNTP | 40 µM each |
| Temperature | 50 °C |

FIG. 30

| Enzymes | Concentration |
|---|---|
| Vent(exo-) | 50 u/mL |
| Nb.BsmI | 400 u/mL |
| Nt.BstNBI | 20 u/mL |
| ttRecJ | 25 nM |

| Oligonucleotides | |
|---|---|
| CBa12-2AULP | 100 nM |
| ApTBa12A3SP | 2.5 nM |
| Let7atoF5TBa12PS0 | 0.1 nM |

| Reaction buffer and condition | |
|---|---|
| Tris-HCL, pH 7.9 | 20 mM |
| $(NH_4)_2SO_4$ | 10 mM |
| KCl | 10 mM |
| $MgSO_4$ | 8.4 mM |
| NaCl | 50 mM |
| dithiothreitol | 3 mM |
| Symperonic F108 | 0.1% |
| BSA | 100 µg/mL |
| EvaGreen | 1x |
| Netropsin | 2 µM |
| dNTP | 40 µM each |
| Temperature | 50 °C |

$\Delta_{bind} = \Delta rG_1 - \Delta rG_2$
$\Delta_{ext} = \Delta rG_2 - \Delta rG_3$

*** Phosphorothioate modifications protecting against exonuclease
● 3' phosphate avoiding extension by the polymerase

FIG. 36 (followed)

c

| Enzymes | Concentration |
|---|---|
| Vent(exo-) | 50 u/mL |
| Nb.BsmI | 400 u/mL |
| Nt.BstNBI | 10 u/mL |
| ttRecJ | 11,25 nM |

| Oligonucleotides | |
|---|---|
| CBe12-3noPS3 | 100 nM |
| pTBe12T5SP | 2.5 nM |
| 92atof5TBe12PS0 | 0.1 nM |
| RPBe-Cy5 | 25 nM |
| RPBa-Hex | 25 nM |

| Reaction buffer and condition | |
|---|---|
| Tris-HCL, pH 7.9 | 20 mM |
| $(NH_4)_2SO_4$ | 10 mM |
| KCl | 10 mM |
| $MgSO_4$ | 8.4 mM |
| NaCl | 50 mM |
| dithiothreitol | 3 mM |
| Symperonic F108 | 0.1% |
| BSA | 500 µg/mL |
| EvaGreen | 0.8x |
| Netropsin | 2 µM |
| dNTP | 50 µM each |
| Temperature | 50 °C | d

| Enzymes | Concentration |
|---|---|
| Vent(exo-) | 50 u/mL |
| Nb.BsmI | 400 u/mL |
| Nt.BstNBI | 10 u/mL |
| ttRecJ | 11,25 nM |

| Oligonucleotides | |
|---|---|
| CBa12-3noPS3 | 100 nM |
| pTBa12T5SP | 2.5 nM |
| Let7atof5TBa12PS0 | 0.1 nM |
| RPBe-Cy5 | 25 nM |
| RPBa-Hex | 25 nM |

| Reaction buffer and condition | |
|---|---|
| Tris-HCL, pH 7.9 | 20 mM |
| $(NH_4)_2SO_4$ | 10 mM |
| KCl | 10 mM |
| $MgSO_4$ | 8.4 mM |
| NaCl | 50 mM |
| dithiothreitol | 3 mM |
| Symperonic F108 | 0.1% |
| BSA | 500 µg/mL |
| EvaGreen | 0.8x |
| Netropsin | 2 µM |
| dNTP | 50 µM each |
| Temperature | 50 °C |

FIG. 37 (followed)

c

| Enzymes | Concentration |
|---|---|
| Vent(exo-) | 50 u/mL |
| Nb.BsmI | 400 u/mL |
| ttRecJ | 11,25 nM |

| Oligonucleotides | |
|---|---|
| CBe12-3noPS3 | 100 nM |
| RPBe-Cy5(2) or RPBe-Cy5(3) | 0-100 nM |

| Reaction buffer and condition | |
|---|---|
| Tris-HCL, pH 7.9 | 20 mM |
| $(NH_4)_2SO_4$ | 10 mM |
| KCl | 10 mM |
| $MgSO_4$ | 8.4 mM |
| NaCl | 50 mM |
| dithiothreitol | 3 mM |
| Symperonic F108 | 0.1% |
| BSA | 500 µg/mL |
| EvaGreen | 0.5x |
| Netropsin | 2 µM |
| dNTP | 50 µM each |
| Temperature | 50 °C |

| Buffer | PP |
|---|---|
| DTT | 3 mM |
| dNTPmix | 50 µM |
| Evagreen | 2.5 % |
| BSA9000S | 2.5 % |
| Nb.BSMI | 4% |
| BsmI (RE) | 0.5 % |
| Vent (Exo-) | 2.5 % |
| ttRecJ/140 | 1.5 % |
| USER | 0.5 % |
| T | 50 °C |
| CFX | |
| Cbe12-3noPS3 | 100 nM |
| pTBe12T5SP | no |
| Various MBBe12 | 0-100 nM |

FIG. 40
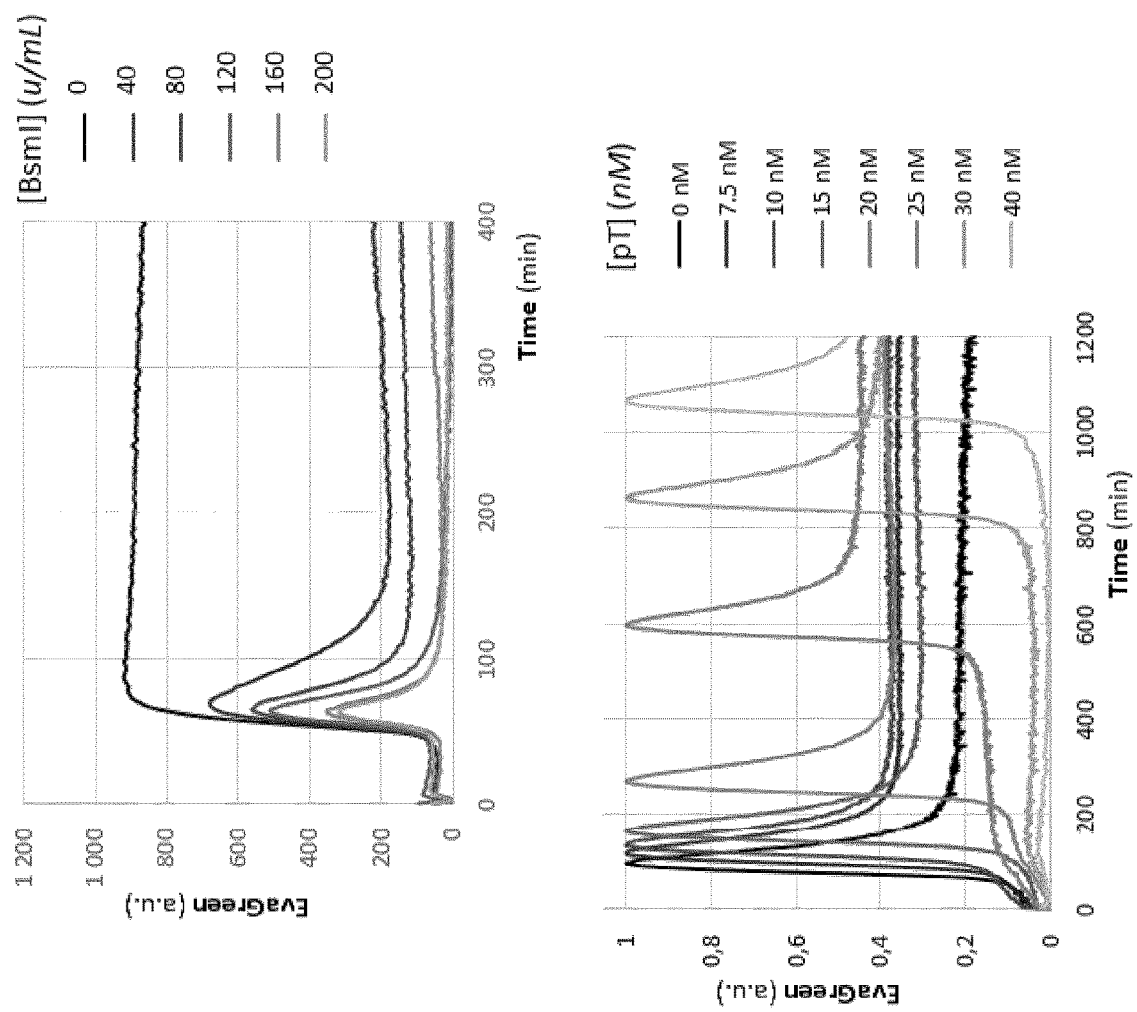
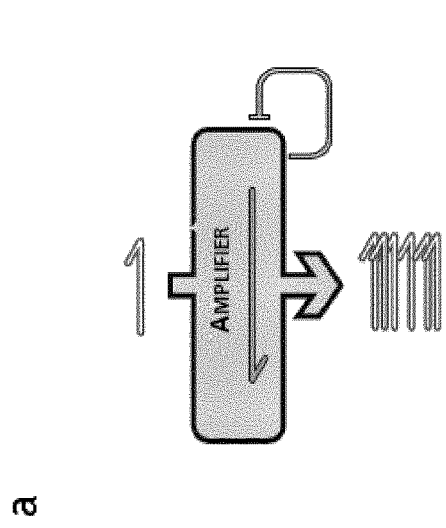
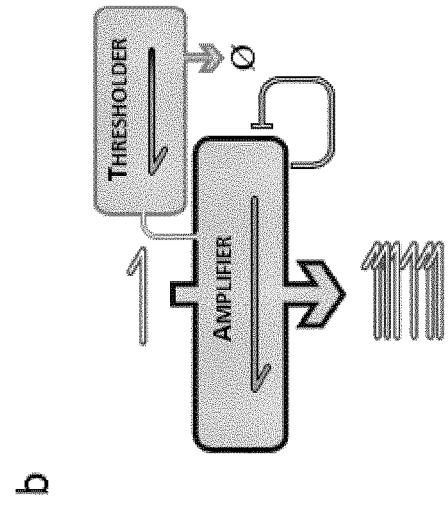

FIG. 40 (followed)

C

| Enzymes | Concentration |
|---|---|
| Bst ws 2.0 | 0.4 u/mL |
| Nb.BsmI | 400 u/mL |
| ttRecJ | 3.75 nM |
| BsmI | 100 u/mL |

| Oligonucleotides | |
|---|---|
| CBa12-1S4bioteg | 100 nM |
| pTBa12A6biot | 0-20 nM |

| Reaction buffer and condition | |
|---|---|
| Tris-HCL, pH 7.9 | 20 mM |
| $(NH_4)_2SO_4$ | 10 mM |
| KCl | 10 mM |
| $MgSO_4$ | 8.4 mM |
| NaCl | 50 mM |
| dithiothreitol | 3 mM |
| Symperonic F108 | 0.1% |
| BSA | 500 µg/mL |
| EvaGreen | 0.4x |
| Netropsin | 2 µM |
| dNTP | 50 µM each |
| Streptavidin | 100 nM |
| Temperature | 45 °C |

| Enzymes | Concentration |
|---|---|
| Bst ws 2.0 | 0.4 u/mL |
| Nb.BsmI | 400 u/mL |
| ttRecJ | 3.75 nM |
| BsmI | 0-200 u/mL |

| Oligonucleotides | |
|---|---|
| CBa12-1S4bioteg | 100 nM |

| Reaction buffer and condition | |
|---|---|
| Tris-HCL, pH 7.9 | 20 mM |
| $(NH_4)_2SO_4$ | 10 mM |
| KCl | 10 mM |
| $MgSO_4$ | 8.4 mM |
| NaCl | 50 mM |
| dithiothreitol | 3 mM |
| Symperonic F108 | 0.1% |
| BSA | 500 µg/mL |
| EvaGreen | 0.4x |
| Netropsin | 2 µM |
| dNTP | 50 µM each |
| Streptavidin | 100 nM |
| Temperature | 45 °C |

FIG. 41 (followed)
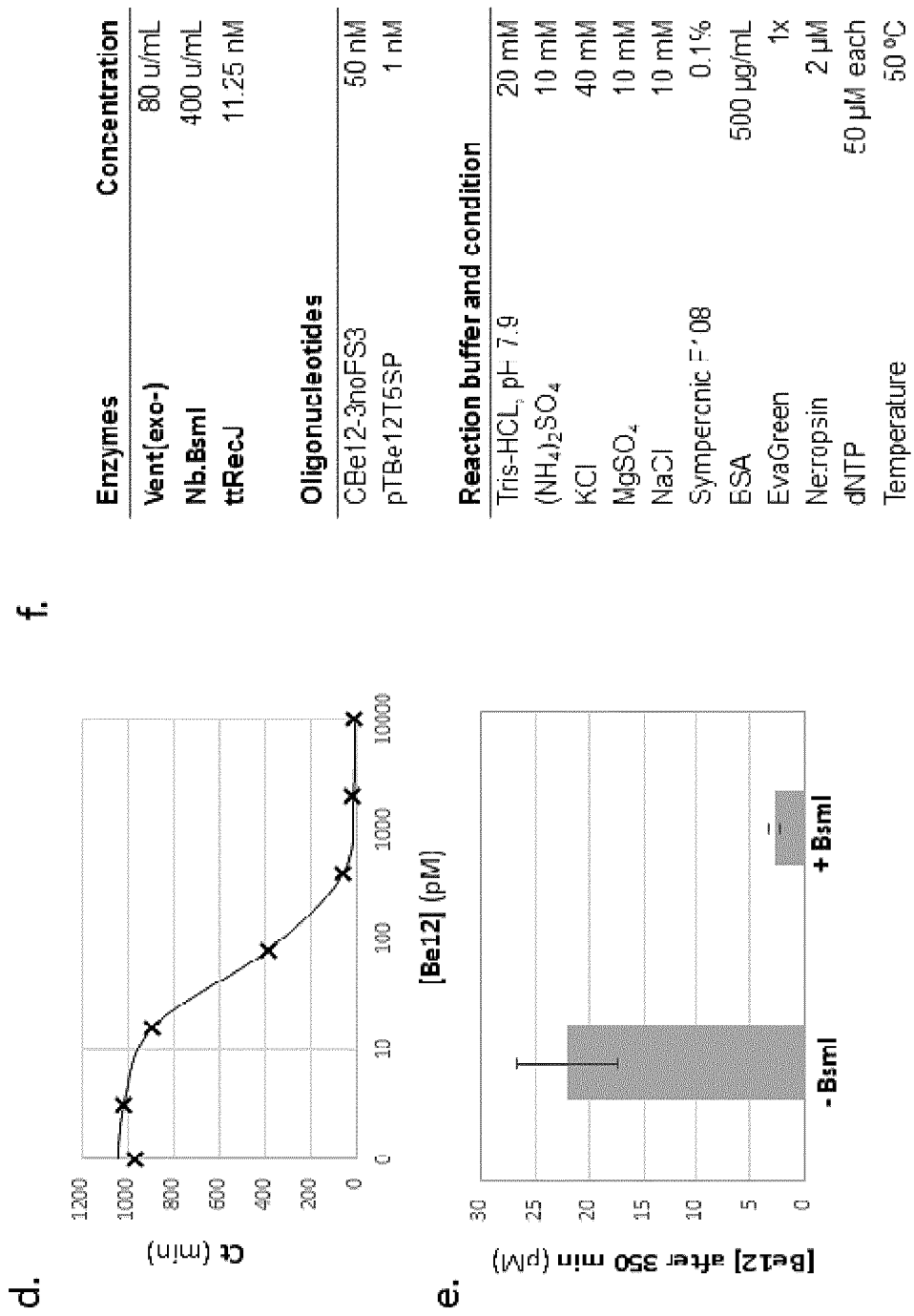

FIG. 42 (followed)

b

| Enzymes | Concentration |
|---|---|
| Vent(exo-) | 60 u/mL |
| Nb.BsmI | 400 u/mL |
| ttRecJ | 11.25 nM |
| Nt.BstNBI | 10 u/mL |
| BsmI | 0 or 100 u/mL |

| Oligonucleotides | |
|---|---|
| CBe12-3noPS3 | 30 nM |
| pTBe12T5SP | 0.75 nM |
| 92atof1Be12-3+3 | 1 nM |
| RPBe-Cy5(2) | 15 nM |
| CBa12-3noPS3 | 30 nM |
| pTBa12T5SP | 0.75 nM |
| Let7atof1Ba12-3+3 | 1 nM |
| RPBa-HEX | 15 nM |

| Reaction buffer and condition | |
|---|---|
| Tris-HCL, pH 7.9 | 20 mM |
| $(NH_4)_2SO_4$ | 10 mM |
| KCl | 10 mM |
| $MgSO_4$ | 8.4 mM |
| NaCl | 50 mM |
| dithiothreitol | 3 mM |
| Symperonic F108 | 0.1% |
| BSA | 500 µg/mL |
| EvaGreen | 0.5x |
| Netropsin | 2 µM |
| dNTP | 50 µM each |
| Temperature | 50 °C |

FIG. 43 (followed)

C

| Enzymes | Concentration |
|---|---|
| Bst ws 2.0 | 0.4 u/mL |
| Nb.BsmI | 400 u/mL |
| ttRecJ | 0 or 3.75 nM |
| BsmI | 100 u/mL |

| Oligonucleotides | |
|---|---|
| CBe12-3noPS3 | 30 nM |
| pTBe12T5SP | 0.75 nM |
| 92atof1Be12-3+3 | 1 nM |
| RPBe-Cy5(2) | 15 nM |
| CBa12-3noPS3 | 30 nM |
| pTBa12T5SP | 0.75 nM |
| Let7atof1Ba12-3+3 | 1 nM |
| RPBa-HEX | 15 nM |

| Reaction buffer and condition | |
|---|---|
| Tris-HCL, pH 7.9 | 20 mM |
| $(NH_4)_2SO_4$ | 10 mM |
| KCl | 10 mM |
| $MgSO_4$ | 8.4 mM |
| NaCl | 50 mM |
| dithiothreitol | 3 mM |
| Symperonic F108 | 0.1% |
| BSA | 500 µg/mL |
| EvaGreen | 0.2x |
| Netropsin | 2 µM |
| dNTP | 50 µM eac |
| Streptavidin | 100 nM |
| Temperature | 50 °C |

METHOD OF ELIMINATING BACKGROUND AMPLIFICATION OF NUCLEIC ACID TARGETS

CROSS-REFERENCE TO RELATED APPLICATIONS

This application is the National Phase of International Patent Application No. PCT/EP2017/053560, filed Feb. 16, 2017, published on Aug. 24, 2017 as WO 2017/140815 A1, which claims priority to International Patent Application No. PCT/IB2016/000352, filed Feb. 16, 2016. The contents of these applications are herein incorporated by reference in their entirety.

TECHNICAL FIELD

The present invention relates to a method of eliminating background amplification in isothermal DNA amplification.

BACKGROUND ART

Hitherto, isothermal exponential amplifications of nucleic acids have a wide range of potential applications. One example is to replace protocols based on PCR (Polymerase Chain Reaction) for the sensitive detection of biomarkers, because they can provide huge amplification of the signal and are simple and fast (see, for example, NPL 1-6).

CITATION LIST

Non Patent Literature

NPL 1: Qian J, et al. (2012) Sequence dependence of isothermal DNA amplification via EXPAR. Nucleic Acids Research 40(11):e87-e87.
NPL 2: Tan E, et al. (2005) Isothermal DNA amplification coupled with DNA nanosphere-based colorimetric detection. Anal Chem 77(24):7984-7992.
NPL 3: Zhang K, et al. (2015) Digital quantification of miRNA directly in plasma using integrated comprehensive droplet digital detection. Lab Chip. doi:10.1039/C5LC00650C.
NPL 4: Van Ness J, Van Ness L, Galas D (2003) Isothermal reactions for the amplification of oligonucleotides. P Natl Acad Sci Usa 100(8):4504-4509.
NPL 5: Tan E, et al. (2008) Specific versus nonspecific isothermal DNA amplification through thermophilic polymerase and nicking enzyme activities. Biochemistry 47(38):9987-9999.
NPL 6: 1. Guatelli, J. C. et al. Isothermal, in vitro amplification of nucleic acids by a multienzyme reaction modeled after retroviral replication. P Natl Acad Sci USA 87, 7797-1878 (1990).
NPL 7: Walker G, Little M, Nadeau J, Shank D (1992) Isothermal in vitro amplification of DNA by a restriction enzyme/DNA polymerase system. P Natl Acad Sci USA 89(1):392.
NPL 8 (Cancel)
NPL 9: Ong J, Evans T C, Tanner N (2012) Compositions and Methods Relating to Variant DNA Polymerases and Synthetic DNA Polymerases. (Ser. No. 13/823,811).
NPL 10: Piepenburg O, Williams C H, Stemple D L, Armes N A (2006) DNA detection using recombination proteins. PLOS biology 4(7):e204.
NPL 11: Recombinase polymerase amplification
NPL 12: Tanner N, Evans TC (2013) Compositions and Methods for Reducing Background DNA Amplification. (Ser. No. 13/799,463).
NPL 12b: Dang C, Janaseya, S D (1996) Oligonucleotide Inhibitors of TaqDNA Polymerase Facilitate Detection of Low Copy Number Targets by PCR, 264, 268-27863
NPL 13: Tanner N, Evans TC Jr (2012) Reducing Template Independent Primer Extension and Threshold Time for Loop Mediated Isothermal Amplification. (Ser. No. 13/671,123).
NPL 14: Fukui, K. & Kuramitsu, S. Simultaneous Use of MutS and RecA for Suppression of Nonspecific Amplification during PCR. Journal of Nucleic Acids 2013, 1-5 (2013).
NPL 15: Mitani, Y. et al. Rapid SNP diagnostics using asymmetric isothermal amplification and a new mismatch-suppression technology. Nat Meth 4, 257-262 (2007).
NPL 16: Padirac, A., Fujii, T. & Rondelez, Y. Quencher-free multiplexed monitoring of DNA reaction circuits. Nucleic Acids Research 40, e118 (2012).
NPL 17: Buh Gasparic, M. et al. Comparison of nine different real-time PCR chemistries for qualitative and quantitative applications in GMO detection. Anal Bioanal Chem 396, 2023-2029 (2010).

PATENT LITERATURE

PTL 1: US 2009/081670 A
PTL 2: WO 2004/067726 A
PTL 3: CN 104662159
PTL 4: AU 2015202439
PTL 5: US 2013/012255 A
PTL 6: WO 2009/012246 A

SUMMARY OF INVENTION

Technical Problem

However, the aforementioned applications are hampered by a general tendency of exponential nucleic acid amplification schemes to have an uncontrolled background signal. This means that, even in the complete absence of the target biomarker (i.e. the single-stranded or double-stranded nucleic acid sequence of interest), the test would ultimately produce non-specific amplification, possibly leading to an erroneous positive conclusion. This is an unavoidable property of the positive amplification loop used in these applications, where the basal state is intrinsically unstable and DNA amplification (of the target sequence or of another sequence) is bound to happen. Primer dimers constitute a well known example in the case of PCR, but many isothermal amplification schemes are even more sensitive to this phenomenon of false positive amplification or background amplification.

For example an important class of isothermal amplification schemes based on repetitive cycles of polymerization and nicking events (referred in the following as "polymerase-nickase amplifications") were initially described in NPL 7 using a restriction enzyme and a DNA template with a modified backbone to implement the nicking step. Later this technique was extended to the use of asymmetric restriction endonucleases called nickases (or nicking enzymes), which cut only one side of the DNA duplex, following recognition of its specific binding site, thereby allowing the use of non-modified DNA template backbones (see, for example, NPL 6-10). Some patents have been taken for these techniques (see, for example, PTL 1-4 and 6). However, it was also obvious that this family of amplification strategy was prone to background (untriggered) amplification, a fact that limited their usefulness in detection strategies. The phenomenon of background amplification in polymerase-nickase exponential amplification has been studied in details (see, for example, NPL 5), and it was shown that two different mechanisms were at play, the first one explaining the self-ignition of the amplification loop (i.e. the false-positive amplification of the correct sequence), and the second one explaining the slower emergence of parasitic species of typically longer lengths (i.e. amplification of a sequence different than the expected one). Various approaches have been proposed to address these problems, in polymerase-nickase amplifications as well as for other types of isothermal amplification, along two lines. In the first one, one attempts to increase the stringency of the amplification loop by improving the molecular amplification machinery that is used. One can for example try to improve the enzymes (e.g. NPL 9), or the template sequence (in the case of polymerase-nickase amplification, after it was shown that some sequences behave better than others in NPL 1). One can also try to improve the buffer and experimental conditions, for example by optimizing the concentrations of salts, by using so called "hot-start" strategies (see, for example, NPL 10-11), or by using additives, which may be small molecules (see, for example, NPL 12), inhibiting oligonucleotides (see, for example NPL 12b) but also surfactants, crowding agents, single strand binding protein (see, for example, NPL 13-14 and PTL 5), mismatch binding protein such as MutS (see, for example, NPL 15) etc. The second approach, which can be used in combination with the first one, consists in using a specific reporting strategy, where the generation of signal is initiated only if one precise sequence is being amplified, not if another one is, thereby avoiding the generation of false positive, even if side reactions occur in the mixture. Well known examples include Taqman® probes, primetime assays, Zen™ probes, cycling probes, molecular beacons and the like (some examples and details are given in NPL 16-17). Here we propose a new approach to reduce and completely eliminate the phenomenon of background amplification. Contrary to previous attempts we do not try to improve the function of the molecular components, but use concepts from molecular programming and dynamical system to ensure that the non-amplified state becomes a possible long-term outcome of the mixture, while retaining the possibility to exponentially amplify the signal, if sufficient stimulus is provided. We also show that this new approach is suitable to build robust, multiplexable, ultra-sensitive and ultra-specific isothermal detection schemes for various nucleic acid targets.

An object of the present invention is to provide a method of eliminating background amplification in isothermal amplification used for the detection of traces nucleic acids.

Solution to Problem

Accordingly, the present invention provides a method of eliminating background amplification in isothermal amplification of nucleic acid targets, the method comprising steps of; preparing a mixture including buffer and enzymes; and adding a first, a second and a third oligonucleotides into the mixture, wherein the first oligonucleotide is an amplification oligonucleotide, the second oligonucleotide is a leak absorption oligonucleotide and the third oligonucleotide is a target-specific conversion oligonucleotide.

In another method, the first oligonucleotide includes a partial repeat structure containing a nicking enzyme recognition site, and the second oligonucleotide is able to bind, extend, deactivate and slowly release the products of polymerization along the first oligonucleotide, thereby inducing a threshold effect.

In yet another method, a 3' side of the third oligonucleotide can bind to a target sequence and upon polymerization and nicking, the third oligonucleotide outputs a sequence able to activate the first oligonucleotide above the threshold adjusted by controlling concentration of the second oligonucleotide.

In yet another method, the enzymes are selected from a list of polymerases, nicking enzymes and exonucleases, the polymerase and the nicking enzyme can drive the isothermal amplification and the exonuclease can avoid saturation of the system.

In yet another method, signal amplification is initiated only when a mixture of enzymes and oligonucleotides receives stimulation above a predetermined threshold.

In yet another method, the threshold is adjusted by controlling a concentration of the second oligonucleotide.

In yet another method, a 3' end of the first oligonucleotide has a reduced affinity for an amplified sequence.

In yet another method, a 3' end of the second oligonucleotide is complementary to the sequence amplified by the first oligonucleotide, and a 5' end of the second oligonucleotide serves as a template to add a deactivating tail to the amplified sequence.

In yet another method, concentrations of the first and second oligonucleotides are selected so that a reaction of the first oligonucleotide is faster than a reaction of the second oligonucleotide at high concentration of the amplified sequence but the reaction on the second oligonucleotide is faster than the reaction of the first oligonucleotide at low concentration of the amplified sequence, thereby effectively eliminating amplification unless the stimulus threshold is crossed.

In yet another method, the target sequence is an RNA or DNA strand of known sequence, which can be used as a biomarker, and its presence or concentration is detected in an ultrasensitive and ultra-specific manner.

In yet another method, multiple target sequences are simultaneously detected within the same sample using multiple sets of the first, the second and the third oligonucleotide with orthogonal sequences able to detect and report independently their specific targets.

In yet another method, forth oligonucleotide which is a reporting probe is added.

In yet another method, the reporting probe is a fluorescent probe.

In yet another method, the reporting probe detects the signal strand amplified by the amplification oligonucleotide.

In yet another method, the probe is a self-complementary structure modified at both extremities by a fluorophore and/or a quencher. As used herein, the term "self-complementary" means that two different of the same molecule can hybridize to each other due to base complementary (A-T and G-C). In our case, the two extremity of the single strand probe (a few nucleotides on the 3' and 5' part) can hybridize to each other and induce the quenching of the fluorophore by the quencher.

In yet another method, the probe comprises a loop which includes a nicking recognition site.

In yet another method, the amplification oligonucleotide contains a recognition site of a restriction enzyme. In this embodiment, several restriction enzymes well known in the art may be used. Examples of such enzymes are BsmI, EcoRI, PstI, BamHI, PvuI. Preferably, the restriction enzyme used in this embodiment is BsmI In yet another method, the degradation speed of the double strand amplification template is controlled by varying the ratio nickase/restriction enzyme.

In yet another method, a restriction enzyme is added, preferably with an exonuclease.

Advantageous Effects of Invention

According to the present invention, background amplification in isothermal exponential DNA amplification is effectively eliminated.

BRIEF DESCRIPTION OF DRAWINGS

FIG. 5 is a table showing experimental condition in Example 2.

FIG. 7 is a first table showing experimental condition in Example 3.

FIG. 9 is a second table showing experimental condition in Example 3.

FIG. 11 is a first table showing experimental condition in Example 4.

FIG. 13 is a second table showing experimental condition in Example 4.

FIG. 14 is a third table showing experimental condition in Example 4.

FIG. 15 is a fourth table showing experimental condition in Example 4.

FIG. 16 is a fifth table showing experimental condition in Example 4.

FIG. 19 is a first table showing experimental condition in Example 5.

FIG. 22 is a second table showing experimental condition in Example 5.

FIG. 25 is a set of schematic views showing multiplexing the detection modules with sequence specific fluorescent reporting.

FIG. 26 is a table showing experimental condition in Example 6.

FIG. 27 is a set of graphs showing experimental results concerning the detection of miRNA miR92a.

FIG. 28 is a table showing experimental condition in Example 8.

FIG. 30 is a table showing experimental condition in Example 8.

FIG. 40 shows a transitory production of signal strand. a. The enzymatic processor is completed with a varying amount of the restriction enzymes (RE) (BsmI, from 0 to 200 u/mL). b. The autocatalytic template is put in presence of varying concentration of pseudo-template which is used here to delays the self-start. c. Experimental conditions.

DESCRIPTION OF EMBODIMENTS

An embodiment will be described in detail with reference to the drawings.

Figure 1:
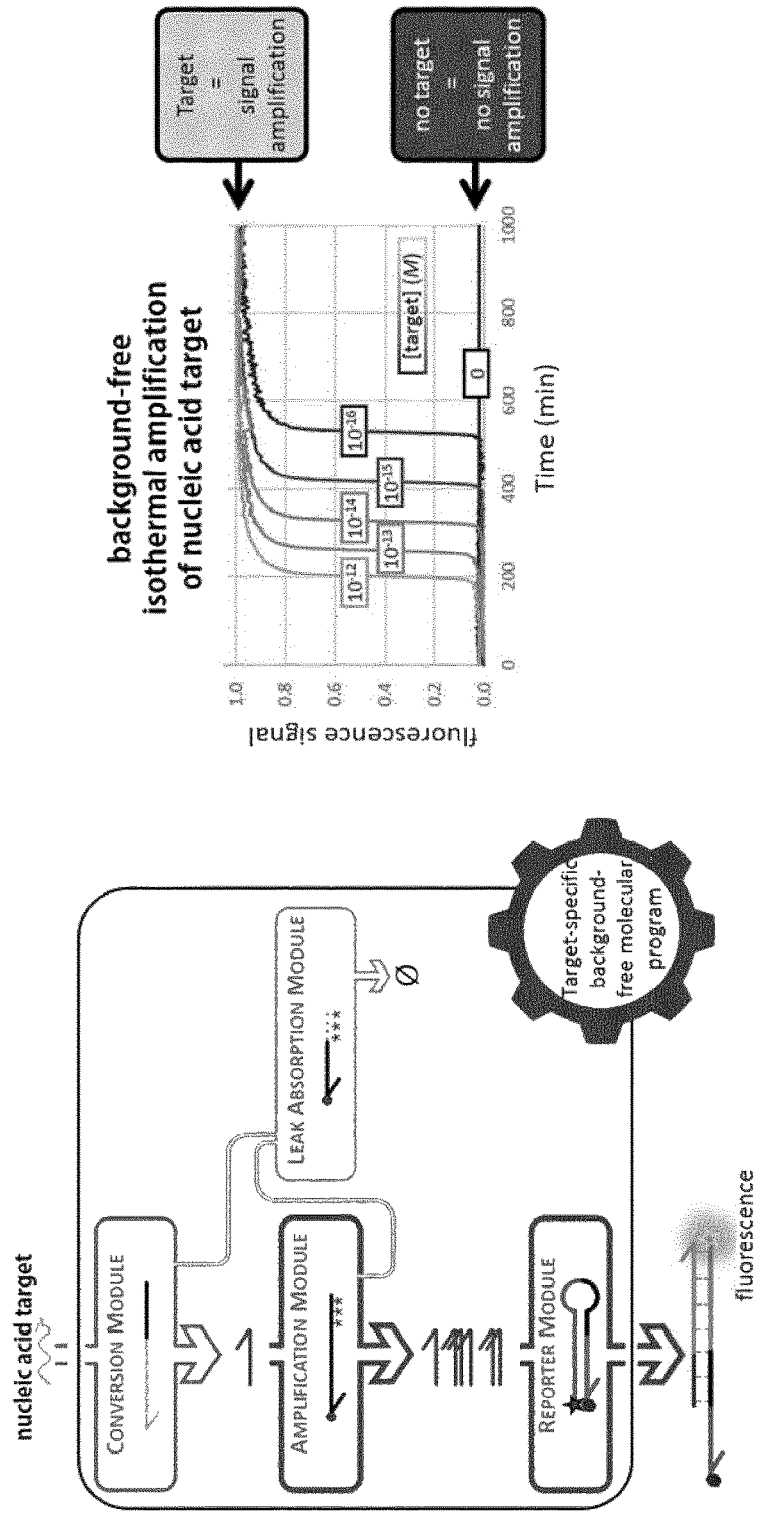
FIG. 1 is a set of schematic views showing a method of background-free isothermal amplification of nucleic acid targets.

FIG. 1 is a schematic views showing a method of background-free isothermal amplification of nucleic acid targets.

In the present embodiment, a new way to eliminate the background signal associated to exponential amplification of nucleic acid target is proposed. The principle of this approach is different from previous arts, because it is rooted in the concepts of dynamical systems, related to the field of molecular programing. Previous arts attempted to improve exponential amplification schemes (isothermal or based on temperature cycling) by improving the specificity of the monitoring (using specific probes) or by refining the robustness of the reaction (by improving the specificity of its constituents, or using additives). These optimization steps can lead only to gradual ameliorations of the sensitivity of the reaction, because the non-amplified state is still unstable, even if its self-triggering is very slow. Therefore, it is bound to generate background non-triggered amplification at some point, placing a lower limit to the concentration of target that can be detected by the technique. Here instead we will completely eliminate the background by making the non-amplified state asymptotically stable, while keeping the ability of the system to migrate to an amplified state upon specific amplification. To do this, we use molecular programming techniques to dynamically stabilize the non-amplified state in a way that does not qualitatively affect the ability of the system to perform exponential amplification. We design the set of reactions in the amplification mixture so that the amplification rate is negative at low concentration (and therefore so the low state becomes asymptotically stable), but is escaped following a finite perturbation. This is obtained by using a continuous deactivation process that is fast (it should be faster than production when in the non-amplified state, so self-triggering is not possible) but saturable (hence it becomes slower than amplification away from the non-amplified state, so that exponential amplification occurs). To do that, (1) the amplification template is modified, (2) an additional DNA template is included in the mixture and (3) an adequate mixture of enzymatic activities is used. This design guarantees that the DNA system will not initiate amplification (it will stay in the basal state) unless a given and adjustable threshold concentration of a specific species is crossed. We also show that this system enables arbitrarily low, ultrasensitive and ultra-specific detection of nucleic acids. More generally, this approach can be used to insert activation thresholds and non-linearities in enzymatic DNA-programmed circuits.

Figure 2A:
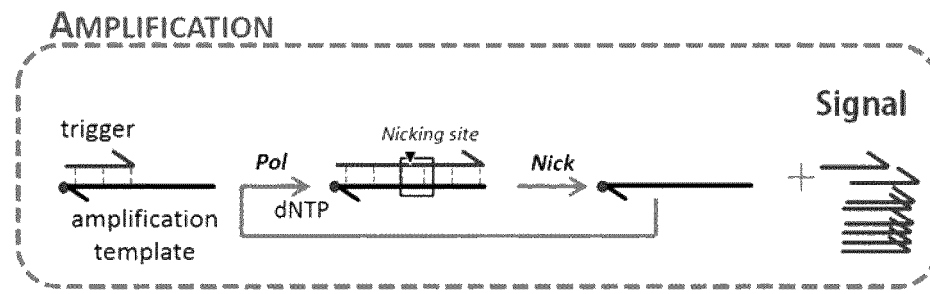
FIG. 2 is a set of schematics views showing the role of the leak-absorption-template in the new design to absorb leaks and avoid unspecific amplification from a DNA amplification loop.

In polymerase/nickase amplification schemes, the amplification is based on a replicative template with a repeat structure that mediates the amplification of a specific trigger (a short single-stranded nucleic acid) via the consecutive extension and nicking of the latter by a polymerase and a nicking enzyme, respectively. When the input side of this template is occupied by a trigger, it acts as a primer and the polymerase extends it. Then the nickase nicks the resulting duplex and releases the output. Repetitions of this process lead to creation of many copies of the output. If the template is designed so that the output can act as a trigger and prime the input side of the repeat templates (meaning input side and output side are partially or completely identical), then exponential amplification of the output (also called trigger, or "amplified sequence" in this description) happens. FIG. 2A shows a schematic representation of a simple amplification network based on polymerization/nicking as used in previous art. In most cases, the 3' end of the template is modified with a non-extensible 3' end (e.g. aminolinker, phosphate) in an attempt to limit background amplification by self-priming of the template. This process is connected to the presence of the targeted nucleic acid by using it directly as a primer, as a primer on the template upstream of the dual repeat structure (NPL 17b and 17c) or in a trigger-generating step on an additional template (which produces the trigger of amplification in presence of the target through polymerase/nickase step (NPL 17d and 17e)). Thus the target initiates the amplification loop, which then autonomously creates a large amount of DNA. This production is detected via various techniques, including fluorescence, with specific or non-specific reporters (like intercalating dyes).

NPL 17b: Xiaobo Zhang et al., "Lab on a Single Microbead: an Ultrasensitive Detection Strategy Enabling microRNA Analysis at the Single-Molecule Level," Chemical Science 6, no. 11 (2015): 6213-18, doi:10.1039/C5SC02641E.

NPL 17c: Li-Ping Ye et al., "Surface-Enhanced Raman Spectroscopy for Simultaneous Sensitive Detection of Multiple microRNAs in Lung Cancer Cells," Chemical Communications 50, no. 80 (Aug. 14, 2014): 11883-86, doi:10.1039/C4CC05598E.

NPL 17d: Hongxia Jia et al., "Ultrasensitive Detection of microRNAs by Exponential Isothermal Amplification.," Angewandte Chemie International Edition 49, no. 32 (Jul. 26, 2010): 5498-5501, doi:10.1002/anie.201001375.

NPL 17e: E Tan et al., "Isothermal DNA Amplification with Gold Nanosphere-Based Visual Colorimetric Readout for Herpes Simplex Virus Detection," Clinical Chemistry 53, no. 11 (Sep. 21, 2007): 2017-20, doi:10.1373/clinchem.2007.091116.

The problem is that template/polymerase and template/polymerase/nickase mixtures are prone to leaking reactions, and/or that the starting mixture may contain some analogs of the target that may induce some leaky production, albeit at a lower rate than the true target (see NPL 5). Because the detection is based on a positive feedback, even a minute production of trigger will inevitably lead to the start of the amplification loop, which will ultimately reach the high level, leading to a false positive detection in an end-point assay, or background amplification in the case of real-time monitoring. This weakness has been reported many times (see, for example, NPL 1-4), and the initiation by spurious polymerization or impurities has been investigated (see, for example, NPL 5). This "self-start" phenomenon is usually observed within the first hour, sometimes within a few minutes only. Such non-specific leak reaction significantly reduces the limit of detection, because self-triggering becomes in fact faster than triggering by minute amounts of targets. Moreover, it makes the analysis delicate, because, since the amplification will eventually happen anyway, one needs to monitor the time of apparition of the signal (and not only the signal itself) in order to infer the initial presence or absence of the target. However, "self-start" is a fundamental property of the design with positive feedback: it is well known from theory of dynamical system that autocatalytic loop produces first-order amplification with an intrinsically unstable 0 state. Whatever happens, they will eventually start to amplify, leading to a false positive.

Figure 2B:
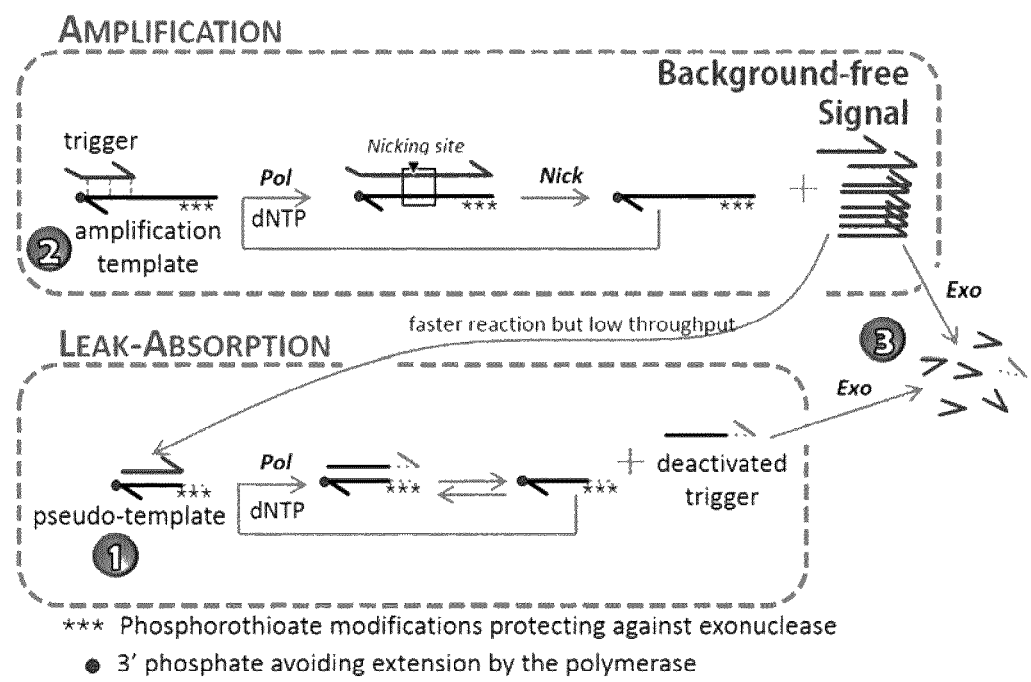

The present embodiment's approach to solve this problem is based on converting the irreversible exponential amplification system into a continuous molecular process in order to absorb leaks and stabilize the initial state. It requires a few modifications of the protocol, which together act to reduce and even suppress completely the background amplification. FIG. 2B shows the design. As shown in FIG. 2B, a number of modifications are used to remove the background amplification: addition of an exonuclease to the mixture; protection of the template with phosphorothioate modification (or other exonuclease blocking possibilities such as biotin-streptavidin modifications or modified bases) to protect the template from the exonuclease; removal of enough bases on the 3' end of the amplification template so that the affinity for the amplified sequence is reduced and the binding reaction is reversible; and importantly, addition of a second template (called pseudo-template or leak absorption oligonucleotide), which binds the amplified sequence more strongly than the regular template but only adds a few nucleotides at its 3' end and thus deactivates it for further priming on the amplification template (because its 3' end is now mismatched). In FIG. 2B, ball-terminated arrowheads show non-extensible 3' ends (3' phosphate modification), and *** represents the protection against exonuclease degradation.

In the present embodiment, a second template, called "pseudo-template" or "leak absorption template", is introduced. The pseudo-template binds and elongates inputs very much like the other template, but the resulting duplex cannot be nicked. Because the extension is short, the elongated trigger is not perfectly stable and slowly melts away. However its new 3' tail, if correctly designed, now forbids any further priming on its cognate template—it has been wasted. This slow de-hybridization step also restores the pseudo-template, allowing it to continuously and catalytically consume a small amount of triggers, and hence absorb the leak. In the presence of the exonuclease in the mixture, the deactivated trigger will eventually be digested, insuring that the pseudo-template can continuously play its role of absorbing the leak and maintaining the system in the basal state. However, the pseudo-template needs to be protected against degradation, exactly like the amplification template is. This is done using a few phosphorothioates modifications at its 5' end (or other exonuclease-blocking possibilities such as biotin-streptavidin modifications or modified bases).

The system is designed so that the trigger binds preferentially on the pseudo-template rather than on the amplification template (when the system is still in the non-amplified state). This can be obtained for example by shortening the amplification template on the input side, so that the melting temperature on the input side is lower than that on the output side and lower than the working temperature, but keeping a full length complementarity on the pseudo-template.

Though, other approaches are possible to adapt the respective binding energies of the trigger on the amplification template and pseudo-template, for example adding modified bases (such as deoxyinosine or abasic sites), or backbone modifications (such as phosphorothioates) to destabilize the duplex on the amplification template, or, on the contrary, using modifications that stabilize the duplex on the pseudo-template (such as or selected from modified bases, LNA bases, RNA bases, fluorophores, stacking agents, dangling bases, groove binders, etc.).

Finally, when an exonuclease enzyme is introduced, this enzyme can digest some of the non-protected single strand DNA present in the system and avoids the accumulation of non-specific products and extended amplification products that would eventually trigger the system if they would be left to accumulate unchecked. Therefore the system can stay permanently in the non-amplified state, waiting for a stimulus.

With these additions, the amplification rate at low concentration (in the non-amplified state) is in fact negative, and the low state can be maintained indefinitely. It is stable in the sense that it is a stable steady state of the corresponding dynamical system. However, if sufficient specific stimulus is provided (for example, by adding a sufficient concentration of trigger strand in the mixture), the pseudo-template leak absorbing capability becomes saturated, the amplification rate becomes positive and exponential amplification happens.

As discussed above, the method of the present invention may be used in the simultaneous detection of multiple targets sequences (multiplex detection). The multiplex detection, i.e. the detection of different targets at the same time in the same sample, is of major concern for biosensing application, especially for microRNA. Indeed, while the presence of a virus or a genetic disease is validated by the detection of a single specific DNA sequence, microRNA-related diseases often involved the dysregulation of several biomarkers that change the microRNA signature of a cell or tissue. A diagnosis will therefore require the detection of multiple microRNA targets (a microRNA pattern).

According to one embodiment of the invention, two autocatalytic templates are 3'-modified with different dyes allowing the detection of two different targets.

According to preferred embodiment, the reporter probes (or also called herein reporting probe or (rP)) were implemented which detect the signal strand amplified by the autocatalytic template. Compared to PCR probes (used for detecting) used in the prior art which must be designed (sequence) and optimized (length) for each target, the reporter probes used in the method of the invention are modular, meaning that they can be connected to any target through the proper bistable module (autocatalyst+pseudotemplate).

In the method of the invention the target is converted by the converter template into triggers that activate the autocatalytic template (passing a threshold set by the pseudo-template concentration) amplifying the signal. This universal signal is captured by the probe that eventually lights on. The reporter probes are self-complementary structures (hairpin) modified at both extremities by a fluorophore and a quencher (that can be either attached in 3' or 5'). The 3' stem and/or the loop are complementary to 8 to 12 nucleotides, preferably to 9 to 11 of the signal strand. When no signal strand is produced, the reporter probes are in a stem-loop structure so that the fluorophore and the quencher are in close proximity: the fluorophore is quenched and thus emits a weak fluorescence signal. If signal strands are produced, they bind the probe that results in the transitory opening of the stem and the unquenching of the fluorophore. The signal strand is finally extended along the probe by the polymerase that leads to the irreversible formation of a highly fluorescent double-stranded species. Each reporter probe is designed to bind the signal strands produced by a specific autocatalytic template. The inventors demonstrated that the specificity of this reporting probes toward very similar signal strand.

In one embodiment of the invention the reporter probes (rP), signal strands are irreversibly captured by the probe after elongation. As a result, part of the signal strands are no more available for the autocatalytic template that could lead to a delay in the amplification.

According to a preferred embodiment, in the reporter probe at least one nicking recognition site is included in the loop of the probe. As a consequence, once a signal strand is elongated by the polymerase, it can be nicked by the nicking enzyme. This reversible mechanism implies that the signal strands are only reversibly trapped by the probe and marginally affect the amplification The reporting probes comprising a nicking recognition site used in the method of the invention allow to overcome several drawbacks such as: i) the weak signal to noise ratio due to the N-quenching mechanism or distant quenching (i.e. TaqMan probes), ii) the lack of modularity since the reporting involved the direct conjugation of the dye to the autocatalytic template, hence the change of dye requires the synthesis of the corresponding autocatalytic template.

The multiplex detection assay proposed herein relies on multiple molecular programs working in parallel in the same enzymatic mixture. Each bistable node (system) is connected upstream to a converted template adapted to the target, and downstream to a reporting probe, each having different emission wavelengths.

Though these orthogonal programs should run independently, they use the same catalytic resources. This could induce competitive effects and crosstalk effect. Especially, once a bistable system has been turned on by its corresponding target, it starts amplifying the corresponding signal strand. Both enzymes sequestration and signal production by one node may affect negatively the other node. To avoid such effect, the inventors developed a strategy that consists in the transitory activation of each node instead of a constitutive production of signal strands (herein indicated as Recovery mechanism). As used herein, the term "transitory activation" relates to the short-lived production of signal strand. In other word, whereas the constitutive activation of a bistable node produces a limitless amount of signal strands, the transitory activation produces a short, transient pulse of signal strands.

To that goal, a restriction enzyme is added to the enzymatic processor. The autocatalytic template is designed so that it contains the recognition site of the restriction enzyme. In its initial state (no trigger), the autocatalytic template is single-stranded and not subject to restriction. Once an input species (trigger or signal strand) binds to the template, it is elongated and the resulting duplex is cut either by the nicking enzyme (the reaction is catalytic and regenerates the template) or by the restriction enzyme (the reaction is noncatalytic and consumes the template). As a result, the autocatalytic templates are progressively destroyed by the restriction enzyme and the autocatalysis stops, having produced signal strand only for a short time. The concentration profile of signal strands depends on the ratio of nicking and restriction enzymes that compete for the same substrate.

Thus, according to another embodiment, the amplification oligonucleotide contains a recognition site of a restriction enzyme. The recognition site may be recognized by each restriction enzyme which is able to be used in the method of the invention. Preferably, the restriction enzymes used in the invention are selected from: BsmI BamHI, EcoRI, Pst1, BsrDI, AseI, HindIII, AciI, PvuI, more preferably BsmI. Preferably, wherein a restriction enzyme is added, an exonuclease is also added.

According to one aspect, the invention also relates to a detection method of nucleic acid targets, particularly RNA comprising the implementation of the method of eliminating background amplification according to the invention. Moreover, this detection method further comprises adding a reporting probe and/or including a recognition site for restriction enzyme in the amplification template as described in the present application.

The method of eliminating background amplification of the invention will be discerned in detailed manner in the examples below referring to the annexed figures.

As indicated above, the method of eliminating background amplification according to the present invention comprises adding different oligonucleotides. The inventors assessed several different oligonucleotides which may be used in the method of the invention.

In order to help the reader, it is provided hereunder a table included all oligonucleotides (all nucleotide sequences) used in this invention.

| SEQ ID NO: | Name of the sequence | Nucleotides Sequance | Function |
|---|---|---|---|
| SEQ ID NO: 1 | CBe12PS3: | C*G*A*TCCTGAATG-CGATCCTGAATG-p | amplification template |
| SEQ ID NO: 2 | CBe12-1PS3 | C*G*A*TCCTGAATG-CGATCCTGAAT-p | amplification template |
| SEQ ID NO: 3 | CBe12-2PS3: | C*G*A*TCCTGAATG-CGATCCTGAA-p | amplification template |
| SEQ ID NO: 4 | Be12 | CATTCAGGATCG | Signal strand |
| SEQ ID NO: 5 | ptBe12T5SP: | T*T*T*T*T-CGATCCTGAATG-p | pseudo-template |
| SEQ ID NO: 6 | decoy1: | C*T*C*G*TCAGAATG-p | decoy binder |

-continued

| SEQ ID NO: | Name of the sequence | Nucleotides Sequence | Function |
|---|---|---|---|
| SEQ ID NO: 7 | decoy2: | C*T*C*G*TCAGAATG-A-p | decoy binder |
| SEQ ID NO: 8 | Ba12 | CATTCTGACGAG | signal strand |
| SEQ ID NO: 9 | CBa12-1PS4: | C*T*C*G*TCAGAATGCTCGTCAGAAT-p | amplification template |
| SEQ ID NO: 10 | ptBa12A4SP: | A*A*A*ACTCGTCAGAATG-p | pseudo-template |
| SEQ ID NO: 11 | ptBa12T5SP | T*T*T*T-CTCGTCAGAATG-p | pseudo-template |
| SEQ ID NO: 12 | ptBa12T4S3P: | T*T*T-CTCGTCAGAATG-p | pseudo-template |
| SEQ ID NO: 13 | ptBa12T3S3P: | T*T*T*-CTCGTCAGAATG-p | pseudo-template |
| SEQ ID NO: 14 | ptBa12T2S3P: | T*T*C*TCGTCAGAATG-p | pseudo-template |
| SEQ ID NO: 15 | ptBa12T1S3P: | T*-C*T*CGTCAGAATG-p | pseudo-template |
| SEQ ID NO: 16 | CBa12-2PS4: | C*T*C*G*TCAGAATG-CTCGTCAGAA-p | amplification template |
| SEQ ID NO: 17 | CBa12PS4: | C*T*C*G*TCAGAATG-CTCGTCAGAATG-p | amplification template |
| SEQ ID NO: 18 | CBa12-1PS4: | C*T*C*GTCAGAATG-CTCGTCAGAAT-p | amplification template |
| SEQ ID NO: 19 | CBa12-3PS4: | C*T*C*G*TCAGAATG-CTCGTCAGA----p | amplification template |
| SEQ ID NO: 20 | pTk12T5S4P: | T*T*T*T-CAATGACUCCTG-p | pseudo-template |
| SEQ ID NO: 21 | ApTk12A1SUP: | A*C*A*ATGACUCCTG-A-p | pseudo-template |
| SEQ ID NO: 22 | ApTk12A2SUP: | A*A*C*AATGACUCCTG-A-p | pseudo-template |
| SEQ ID NO: 23 | ApTk12A3PS: | A*A*A*-C*AATGACUCCTG-A-p | pseudo-template |
| SEQ ID NO: 24 | ApTk12A4SUP: | A*A*A*ACAATGAC8CCTG A-p | pseudo-template |
| SEQ ID NO: 25 | ApTk12A5SUP: | A*A*A*AA CAATGAC8CCTG A-p | pseudo-template |
| SEQ ID NO: 26 | ApTk12A6SUP: | A*A*A*AAA CAATGAC8CCTG A-p | pseudo-template |
| SEQ ID NO: 27 | D21DNA | TAGCTTATCAGACTGATGTTGA | DNA strand corresponding to miR-21 |
| SEQ ID NO: 28 | miR-21 | UAGCUUAUCAGACUGAUGUUGA | synthetic oligoribonucleotide |
| SEQ ID NO: 29 | Bc12 | CATTCTGGACTG | signal strand |
| SEQ ID NO: 30 | Let7a | UGAGGUAGUAGGUUGUAUAGUU | synthetic oligoribonucleotide |
| SEQ ID NO: 31 | Let7b | UGAGGUAGUAGGUUGUGUGGUU | synthetic oligoribonucleotide |

-continued

| SEQ ID NO: | Name of the sequence | Nucleotides Sequence | Function |
|---|---|---|---|
| SEQ ID NO: 32 | Let7c | UGAGGUAGUAGGUUGUAUGGUU | synthetic oligoribonucleotide |
| SEQ ID NO: 33 | Ck12-2PS4bioteg | bioteg* C*A*A* TGA CUC CTG CAA TGA CTC C p | Amplification template |
| SEQ ID NO: 34 | Cba12-2biot3 | C*T*C*G*TCAGAATG CTCGTCAGAA bioteg | amplification template |
| SEQ ID NO: 35 | ptBa12A5SP | A*A*A*A*A CTC GTC AGA ATG p | pseudo-template |
| SEQ ID NO: 36 | Cbe12-2S4P | C*G*A*T*CCTGAATGCGATCCTGAA p | amplification template |
| SEQ ID NO: 37 | ApTBe12A3S3P | A*A*A*CGATCCTGAATGAp | pseudo-template |
| SEQ ID NO: 38 | CBe12-2noPS3 | C*G*A*TCCTGAATGCGATCCTGAA | amplification template |
| SEQ ID NO: 39 | Ck12-2S4noUbioteg | Bioteg CAA TGA CUC CTG CAA TGA CTC C p | amplification template |
| SEQ ID NO: 40 | ApTk12A5S3P | A*A*A*AACAATGACUCCTGA p | pseudo-template |
| SEQ ID NO: 41 | CBe12-2AULP | C*G*A*TCCTGAATGCGATCCTGA | amplification template |
| SEQ ID NO: 42 | D21tof5TBe12S3P | C*G*A*TCCTGAAAGCGAAGTTTGACT C ATCAACATCAGTCTGATAAGCTA p | conversion template |
| SEQ ID NO: 43 | CBe12-3noPS3 | C*G*A*TCCTGAATGCGATCCTGA | amplification template |
| SEQ ID NO: 44 | D21tofBe12S0P | CGATCCTGAATG TCA ACA TCA GTC TGA TAA GCT A p | conversion template |
| SEQ ID NO: 45 | CBe12-2SPCy355 | Cy3.5 *C*G*ATCCTGAATGCGATCCATCCTGA A p | amplification template |
| SEQ ID NO: 46 | CBc12SPBMN35 | BMN3*C*A*G*TCCAGAATGCAGTCCA GAA p | amplification template |
| SEQ ID NO: 47 | pTBc12T5SP | T*T*T*T*TCAGTCCAGAATG p | pseudo-template |
| SEQ ID NO: 48 | mir92a | AGG UUG GGA UCG GUU GCA AUG CU | synthetic oligoribonucleotide |
| SEQ ID NO: 49 | 92atoF5TBe12PS0 | CGA TCC TGA AAG CGA AG T TTG ACT CAA GCA TTG CAA CCG ATC CCA ACC p | conversion template |
| SEQ ID NO: 50 | Let7atof5TBa12 S0P | CTC GTC AGA AAG CGA AGT TTG ACT CAA ACT ATA CAA CCT ACT ACC TCA p | conversion template |
| SEQ ID NO: 51 | CBa12-2AULP | C*T*C*GTCAGAATG CTCGTCAGAA A GCGAAGC p | amplification template |
| SEQ ID NO: 52 | ApTBa12A3S3P | A*A*A*CTCGTCAGAATGA | pseudo-template |
| SEQ ID NO: 53 | RPBe-Cy6 | bioteg TTT TG DDQII CAT TCAATT TTC GAT CCT GAA TG Cy5 | reporting probe |
| SEQ ID NO: 54 | CBe12-1S4bioteg | *C*G*A*TCCTGAATGCGATCCTGAAT p | amplification template |
| SEQ ID NO: 55 | Cba12Sbioteg | bioteg *C*T*C*GTCAGAATGCTCGTCAGAATG p | amplification template |

| SEQ ID NO: | Name of the sequence | Nucleotides Sequance | Function |
|---|---|---|---|
| SEQ ID NO: 56 | RPBa-Hex | biotin TTTTG BMNQ530 AATTCTATTTT CTC GTC AGA ATT Hex | reporting probe |
| SEQ ID NO: 57 | Cba12-3noPS3 | C*T*C*GTCAGAATG CTCGTCAGA | amplification template |
| SEQ ID NO: 58 | RPBe-Cy5(2) | Cy5 *T*T*CAGGTTTTCGATCCTGAA BHQ2 | reporting probe |
| SEQ ID NO: 59 | RPBe-Cy5(3) | Cy5 *A*T*TCAGAATGCGATCCTGAAT BHQ2 | reporting probe |
| SEQ ID NO: 60 | ptBa12A6biot | biotin*A*A*AAAACTCGTCAGAATG p | pseudo-template |
| SEQ ID NO: 61 | 92atof1Be12-3+3 | ATGCGATCCTGACGTTTGACTCAA GCA TTG CAA CCG ATC CCA ACC | conversion template |
| SEQ ID NO: 62 | Let7atof1Ba12-3+3 | ATGCTCGTCAGA CGT TTG ACT CAA ACT ATA CAA CCT ACT ACC TCA | conversion template |
| SEQ ID NO: 63 | CBc12-3noPS3 | C*A*G*TCCAGAATGCAGTCCAGA | amplification template |
| SEQ ID NO: 64 | RPBc-FAM | FAM*T*T*CTGG TTTTCAGTCCAGAA BHQ1 | reporting probe |

For the modified sequence, in the context of the present invention the following symbols relate to:
"bioteg": triethyleneglycol-conjugated biotin
"p": 3' phosphate modification;
"*": phosphorothioate backbone modification (protection against exonuclease);
Cy35: Cyanine3.5 fluorophore
BMN3: BMN3 fluorophore
Cy5: cyanine 5 fluorophore
Biotin: aminoethoxy-ethoxyethanol-conjugated biotin;
Hex: hexachlorofluorescein fluorophore
BHQ1 Black Hole quencher 1
BHQ2: Black Hole quencher 2
BMNQ530: BMNQ530 quencher Various combinations of templates may be used in the method of eliminating background amplification of the invention on the basis of the sequences listed above and the examples described herein. The person skilled in the art, starting from the present description and general knowledge concerning nucleotide design will be able to determine other templates and other combination in order to implement the method of the invention.

Next will be described Example 1, regarding background amplification in polymerase/nickase systems capable of exponential amplification, which is decreased, but not abolished, by only shortening the 3' end of the amplification template, or by shortening the 3' end of the amplification template and adding exonuclease.

Figures 3A, 3B:
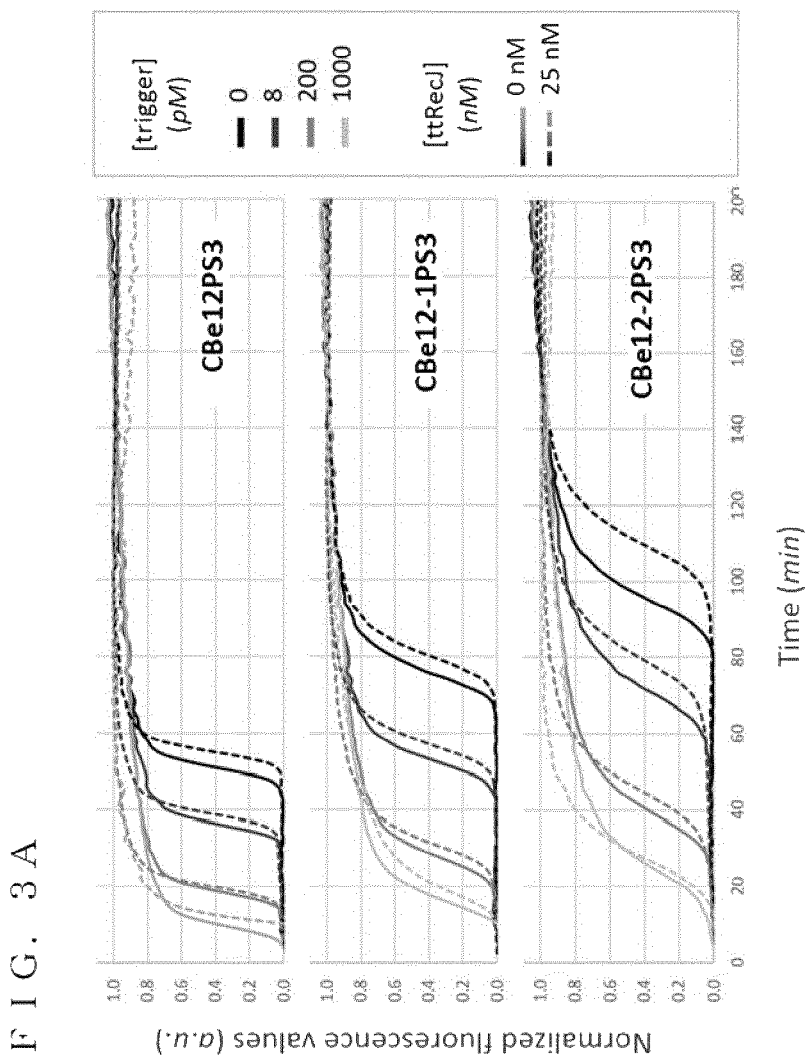
FIG. 3 is a set of graphs showing amplification profiles for a positive feedback loop based on polymerase/nickase reactions for various amplification designs and various initial concentrations of trigger.

FIG. 3A is a set of graphs showing amplification profiles for a positive feedback loop based on polymerase/nickase reactions for various amplification designs and various initial concentrations or trigger. FIG. 3B is a table showing experimental condition in Example 1.

By shortening the amplification template, the melting temperature on the input side becomes much lower than the working temperature. This avoids the generation of stable intermediates by spurious reactions, because, after nicking of the extended product (cf. "deactivated trigger" in FIG. 2B), it is likely that the input will melt away and re-hybridize (on the same template or another) before it can trigger the production of another output. Therefore there is no irreversible step in the activation process, and this results in a decrease of the rate of the background amplification. The fact that the amplification reaction happens well above the melting temperature for the trigger on the input side of the template indicates that the polymerase has a high affinity for the primer-template structure, which allows it to capture and extend even transiently formed substrates.

To show this, an exponential amplification system using the polymerase Bst2.0 WarmStart, the nicking enzyme Nb.BsmI and possibly an exonuclease was built, and its behavior was observed (as shown in FIG. 3) in the presence of various quantities of its trigger or in the absence of trigger. We use an intercalating dye to report on the concentration of DNA in the mixture. The amplification reaction was driven by a single amplification template, which was either a perfect dual repeat of an 11-mer containing the nicking enzyme recognition site, or had been shortened by one or two bases on the input (3') side. The thermophilic 5'→3' exonuclease ttRecJ from Thermus thermophilus (purified and stored as in NLPL 18) was used. It is generally used at a final concentration of 25 nM in the following Examples.

NPL 18: Yamagata A, Masui R, Kakuta Y, Kuramitsu S, Fukuyama K (2001) Overexpression, purification and characterization of RecJ protein from Thermus thermophilus HB8 and its core domain. Nucleic Acids Research 29(22):4617.

A reaction mixture is assembled, with the following final concentrations in the buffer (polymerase and nicking enzyme were obtained from commercial stocks) (cf. FIG. 3B). The templates were used at 50 nM in the final mixture. The 3' Phosphate modification was intended to block possible (templated or untemplated) extension of the 3' end of the templates. Other types of modifications could be used as well for the same purpose (in fact any 3' terminal OH modification could be used):

CBe12PS3:
C*G*A*TCCTGAATG-CGATCCTGAATG-Phos
(corresponding to SEQ ID NO: 1)

CBe12-1PS3:
C*G*A*TCCTGAATG-CGATCCTGAAT-Phos
(corresponding to SEQ ID NO: 2)

CBe12-2PS3:
C*G*A*TCCTGAATG-CGATCCTGAA-Phos
(corresponding to SEQ ID NO: 3)

At the start of the incubation, the input (Be12=CATTCAGGATCG, corresponding to SEQ ID NO: 4) was introduced in the tubes at 0 pM (milliQ was used instead), 8 pM, 200 pM and 1 nM concentrations.

Reactions were assembled on ice in a total volume of 10 µL and run at 45° C. in a MiniOpticon or CFX96 real-time PCR detection system (Biorad). The fluorescence in the EvaGreen channel was monitored every 2 minutes using the first channel of the CFX96 thermocycler. Enzymes: Bst2.0 WarmStart DNA polymerase and the nicking endonuclease Nb.BsmI (both from NEB) were respectively used at 4 U/mL and 400 U/mL (respectively 0.05% and 4% final dilutions of the commercial stock solutions) and ttRecJ was used at 25 nM when added. As illustrated in FIG. 3A, it can be seen that the background amplification (amplification in the absence of trigger), already reported for previous polymerase/nickase exponential amplification systems, is delayed for templates with missing bases on the 3' side. However, it is still observed after some time, even in the presence of exonuclease. This background amplification has been attributed to spurious polymerization (i.e. polymerization in the absence of primer or template, see, for example, NPL 21) or the presence of impurities in the mixture (see NPL 1 to 5), but it is in fact an intrinsic property of simple exponential (first order) nucleic acid amplification systems. NPL 21: Ogata N, Miura T (1998) Creation of genetic information by DNA polymerase of the thermophilic bacterium *Thermus thermophilus*. Nucleic Acids Research 26(20):4657-4661.

Next will be described Example 2, regarding elimination of background amplification using a pseudo-template.

Figure 4:
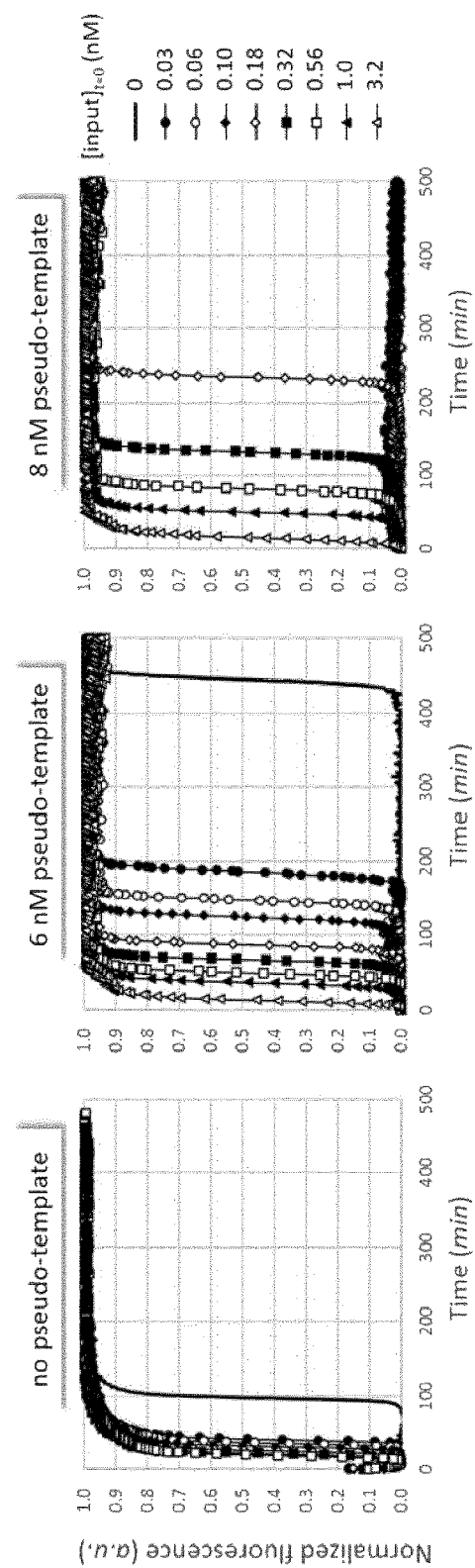
FIG. 4 is a set of graphs showing effect of the pseudo-template on the background amplification.

FIG. 4 is a set of graphs showing effect of the pseudo-template on the background amplification. FIG. 5 is a table showing experimental condition in Example 2.

The amplification template as in Example 1 is combined with an additional strand, called a pseudo-template (leak absorption template) and an exonuclease, introduced in the same mixture. The pseudo-template sequence has two parts. The 3' side is the complementary to the amplified sequence. The 5' part is a short extension, which encodes the sequence of the tail that will be appended to the amplified sequence. It can be chosen arbitrarily but one should avoid the same sequence as the amplification template at that position (because in this case, the extended amplified sequence would not be deactivated and could still be extended after migration to the amplification template). For the same reason it needs to be long enough, preferably between 2 and 6 nucleotides so that it efficiently blocks extension of the amplified sequence once it has been tailed. Moreover, the thermodynamic characteristics of that tail sequence will impact the efficiency of the pseudo-template in its function of eliminating the background amplification as demonstrated in Example 3. The exonuclease is included in the mixture in order to continuously remove a fraction of the single strands.

In the present Example, an amplification system is created using the Bst DNA polymerase, warm start, and the nicking enzyme Nb.BsmI, the template CBe12-2PS3 (sequence: C*G*A*TCCTGAATG-CGATCCTGAA-Phos, corresponding to SEQ ID N0:3) and the pseudo-template pTBe12T5SP (sequence: T*T*T*T*T-CGATCCTGAATG-Phos, corresponding to SEQ ID NO: 5) at various concentrations (0, 6 nM, 8 nM). Then these mixtures are split in different tubes, which are spiked with various quantities of input (Be12=CATTCAGGATCG, corresponding to SEQ ID NO:4), and the behavior is observed by using the intercalating dye EvaGreen to follow the concentration of DNA in the mixture by fluorescence. The composition is shown in a table of FIG. 5 and the results are shown as graphs of the time plot of EvaGreen fluorescence in FIG. 4.

It can be observed in FIG. 4 that, at a sufficient concentration of pseudo-template, the background amplification completely vanishes, and a threshold for amplification appears. The left end graph (with no pseudo-template, but with exonuclease) shows again that the addition of the exonuclease alone does not qualitatively change the function of the system. The exponential amplification is still observed in the presence of trigger and the self-start phenomenon (in the absence of trigger) happens around time=100 minutes. With addition of the pseudo-template, the system keeps its ability to exponentially amplify the signal but, above a given concentration of pseudo-template (the value is between 6 and 8 nM, based on graphs in the center and the right end), the self-start phenomenon is completely abolished, and the amplification now happens only above a given threshold of input concentration.

Next will be described Example 3, regarding mechanism of background amplification removal.

Figure 6:
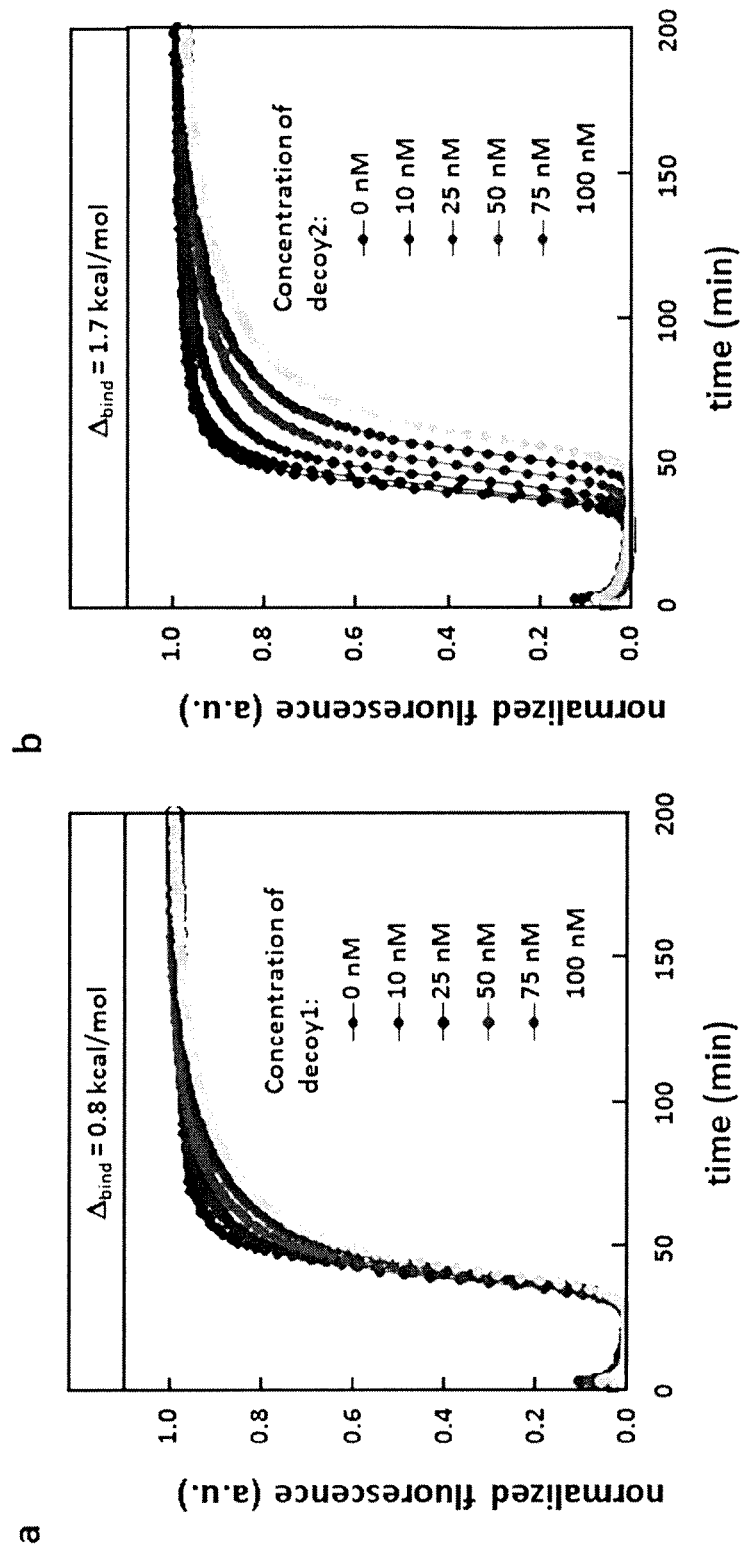
FIG. 6 is a set of graphs showing effect of a simple decoy on a simple autocatalytic loop.

FIG. 6 is a set of graphs showing effect of a simple decoy on a simple autocatalytic loop. FIG. 7 is a first table showing experimental condition in Example 3.

The mechanism, by which the pseudo-template can remove background amplification, is different from the use of blocking agents, competitive inhibitors or suicide inhibitors. This is because the mechanism at play here involves a continuous, active, irreversible and catalytic modification of the species undergoing exponential growth, and not just a modification or a minimization of the non-specific reaction rate. This is to say that the non-specific production still occurs, but is continuously absorbed by the system's design as long as it is below some threshold value. Above this threshold value, the leak-absorption capacity is overcome and exponential amplification starts. Therefore, to completely eliminate background amplification, one needs to introduce a sufficient amount of pseudo-template whose continuous absorption and deactivation capacity is higher than the leak rate.

In the present Example, the difference between pseudo-template, which actively deactivates a fraction of the amplified sequence, and passive competitor, which competes for the binding of the amplified sequence, but does not modify it, is experimentally demonstrated. A master mix with the composition shown in a table of FIG. 7 is created.

Additionally, various concentrations of two decoy binders (decoy1=C*T*C*G*TCAGAATG-Phos, corresponding to SEQ ID NO: 6 and decoy2=C*T*C*G*TCAGAATG-A-Phos, corresponding to SEQ ID NO: 7 which are protected against degradation, can bind the amplification sequence, but do not lead to its elongation) are introduced. However, no trigger (i.e. no Ba12=CATTCTGACGAG, corresponding to SEQ ID NO:8) is introduced, and, upon incubation at 45° C., the mixture is observed until the background amplification happens.

FIG. 6 shows an effect of a simple decoy on the autocatalytic loop mediated by CBa12-2PS4 (corresponding to SEQ ID NO: 16). It can be seen that background amplification occurs within one hour and is marginally affected by the addition of decoy binders decoy1 (see FIG. 6A) or decoy2 (see FIG. 6B), even when the decoy is a better binder and is twice more concentrated than the amount of autocatalytic template used (100 nM). This is in sharp contrast to the effect of pseudo-templates, which efficiently eliminate the background amplification, even when much lower concentrations are used. This supports the fact that a very different mechanism is at play, not similar to the use of blocking agents.

It is seen in FIG. 6, that, if a simple sequence complementary to the trigger (i.e. a "passive" competitive binder, not involving a transformation of the substrate) is included in the mixture, stabilization of the non-amplified state is never detected, even when the affinity of the trigger for the decoy competitor is much larger than for the amplification template, and this decoy competitor is present in very high concentration (compared with Example 2 where only 8 nM of pseudo-template is enough to completely abolish the background amplification). This shows that the catalytic, continuous chemical modification of the substrate, leading to its de-activation, which is an innovative point in our approach, is necessary to obtain the effect.

Next will be described Example 4, regarding optimization of background amplification removal.

Figure 8A:
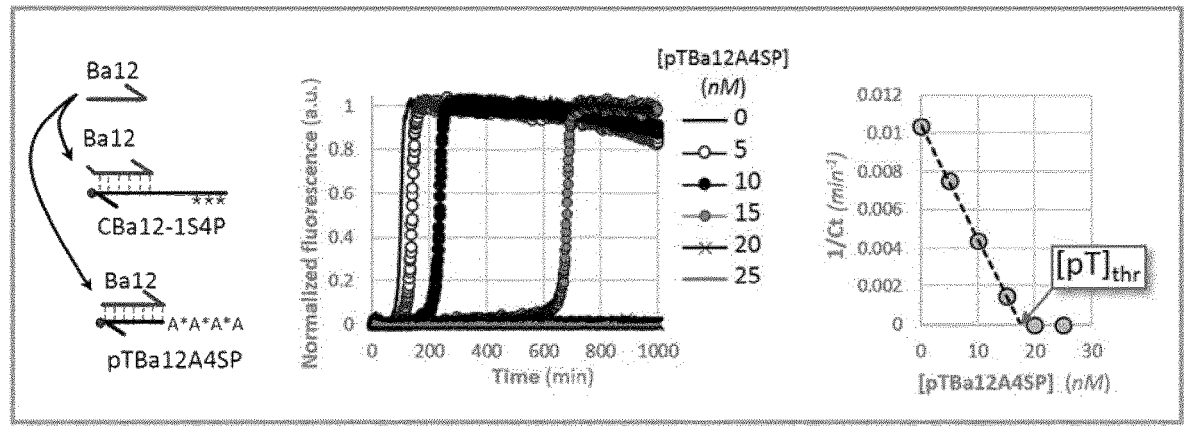
FIG. 8 is a set of graphs showing the removal of background amplification.
Figure 8B:
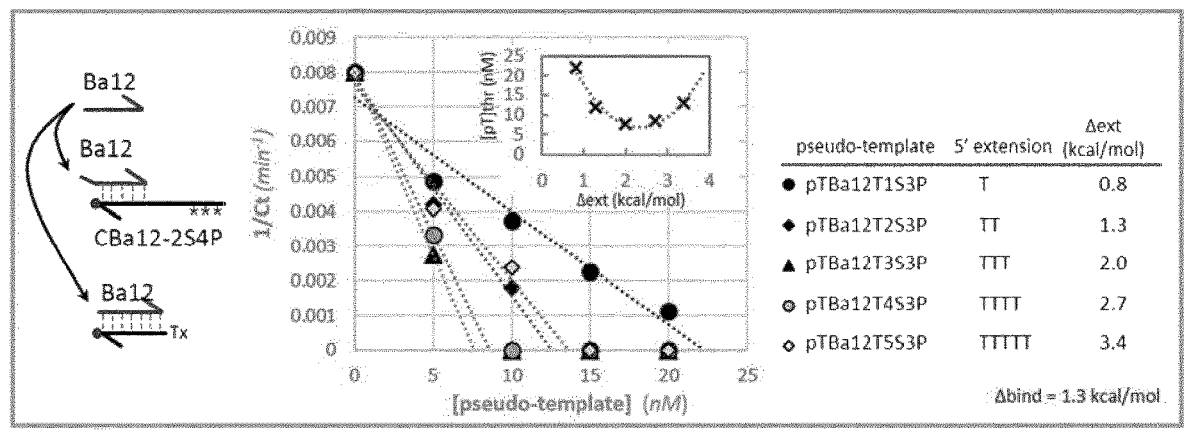
Figure 8C:
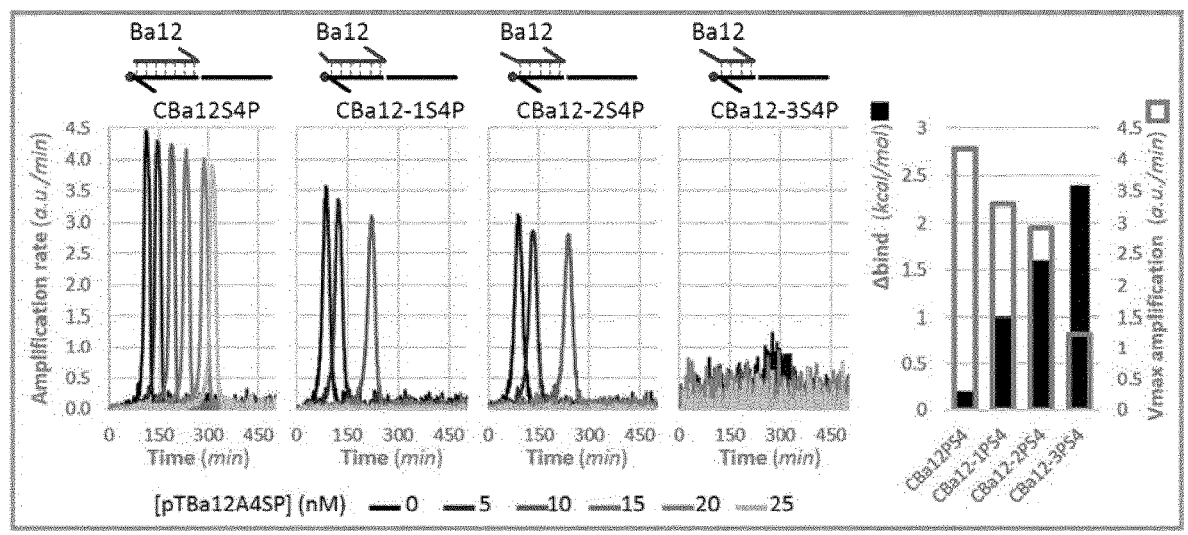

FIG. 8 shows the removal of background amplification using a pseudo-template and ttRecJ, and optimization of the design for the template and pseudo-template. Each fluorescence time trace represents an independent experiment. FIG. 8A shows a background removal by increasing concentrations of pseudo-template (amplification template=CBa12-1PS4: C*T*C*G*TCAGAATGCTCGTCAGAAT-Phos, corresponding to SEQ ID NO: 9), pseudo-template=pTBa12A4SP: A*A*A*ACTCGTCAGAATG-Phosp, corresponding to SEQ ID NO: 10). Plotting 1/Ct as a function of pseudo-template concentration shows in some cases a linear correlation. In these cases, a linear regression allows the determination of the critical pseudo-template concentration (noted [pT]thr, i.e. the concentration above which background amplification vanishes). FIG. 8B shows the effect of pseudo-template design. Amplification template CBa12-2PS4 (corresponding to SEQ ID NO: 16) was incubated with varying concentrations of various pseudo-templates and the time to self-start was measured. The pseudo-templates used all have the same sequence except for the tailing bases at the 5' end. FIG. 8C shows the influence of the design of the amplification template. Various amplification templates (schematized in the upper panels) were incubated in the presence of varying concentrations of a given pseudo-template.

A master mix with the composition shown in a table of FIG. 9 is created.

Additionally, various concentrations of the pseudo-template pTBa12A4SP (sequence: A*A*A*A*CTCGTCAGAATG-Phos, corresponding to SEQ ID NO: 10) ranging from 0 to 25 nM, are introduced. However, no trigger (i.e. no Ba12=CATTCTGACGAG, corresponding to SEQ ID NO: 8)) is introduced, and upon incubation at 45° C. the fluorescence of the mixture is observed until the background amplification happens.

FIG. 8A shows an evaluation of the evolution of the background amplification time as a function of the concentration of pseudo-template in the mixture. When the inverse of the background amplification time is plotted as a function of pseudo-template, a line intersects the x-axis. This confirms that the background amplification time is delayed to hyperbolically increasing time, using small and finite concentrations of pseudo-templates. This is a signature of the bifurcation to the bistable regime. This proves that the working principle of background removal as presented here is rooted in out-of-equilibrium dynamical systems, and not in improvement of the specific kinetic rates versus the non-specific kinetic rates.

It was also attempted to evaluate the best design for the two nucleic acid elements which are used to encode the behavior of the system: the amplification template and the pseudo-template.

First, for the pseudo-template, the same mixture is assembled as above, but now with added various concentrations (from 0 to 20 nM) of pseudo-templates with various designs (ptBa12T5SP=T*T*T*T*T-CTCGTCAGAATG-Phos (corresponding to SEQ ID NO: 11), ptBa12T4S3P=T*T*T*T-CTCGTCAGAATG-Phos; (corresponding to SEQ ID NO: 12) ptBa12T3S3P=T*T*T*-CTCGTCAGAATG-Phos—(corresponding to SEQ ID NO: 13); ptBa12T2S3P=T*T*C*TCGTCAGAATG-Phos—(corresponding to SEQ ID NO: 14); ptBa12T1S3P= T-*C*T*CGTCAGAATG-Phos, —(corresponding to SEQ ID NO: 15)), which differ in their 3' tailing extremity. All these experiments use CBa12-2PS4 (sequence: C*T*C*G*TCAGAATG-CTCGTCAGAA-Phos, —(corresponding to SEQ ID NO: 16)) as the amplification template. In FIG. 8B, optimal design rules are found: the pseudo-template requires at least a two-base tail to efficiently eliminate the background amplification; above this length, pseudo-template designs with shorter tails are more efficient (more experiments are presented in FIG. 10). This is because their turnover, linked to the de-hybridization rate of the extended trigger from the pseudo-template, is faster, so that these shorter pseudo-templates are more efficient.

Second, the design of the template is looked at, by removing zero, one, two or three bases on the input side, and having a 3' phosphate modification to avoid re-elongation of the template (by trigger-templated extension). The reaction is assembled as above, with various templates (CBa12PS4=C*T*C*G*TCAGAATGCTCGTCAGAATG-Phos; —(corresponding to SEQ ID NO: 17) CBa12-1PS4=C*T*C*G*TCAGAATG-CTCGTCAGAAT - - - Phos; —(corresponding to SEQ ID NO: 18) CBa12-2PS4=C*T*C*G*TCAGAATGCTCGTCAGAA - - - Phos; —(corresponding to SEQ ID NO: 16) CBa12-3PS4=C*T*C*G*TCAGAATGCTCGTCAGA - - - Phos; —(corresponding to SEQ ID NO: 19) where "- -" is used to highlight the removed bases) and, in each case, various concentrations of an efficient pseudo-template (ptBa12A4SP=A*A*A*A*CTCGTCAGAATG-Phos, —corresponding to SEQ ID NO: 10) are added. FIG. 8C shows that it is necessary to have at least one base deleted from the template to observe the complete background-removal effect by the pseudo-template. This can be rationalized by the fact that it is necessary that the effective first-order rate with the pseudo-template is higher than that with the amplification template. The removal of two bases also provides a system where the self-start can be abolished while maintaining a correct amplification rate. However, the removal of three bases on the amplification template decreases excessively the amplification rate.

Next will be described Example 5, regarding the generality of the mechanism of background amplification removal.

Figure 10:
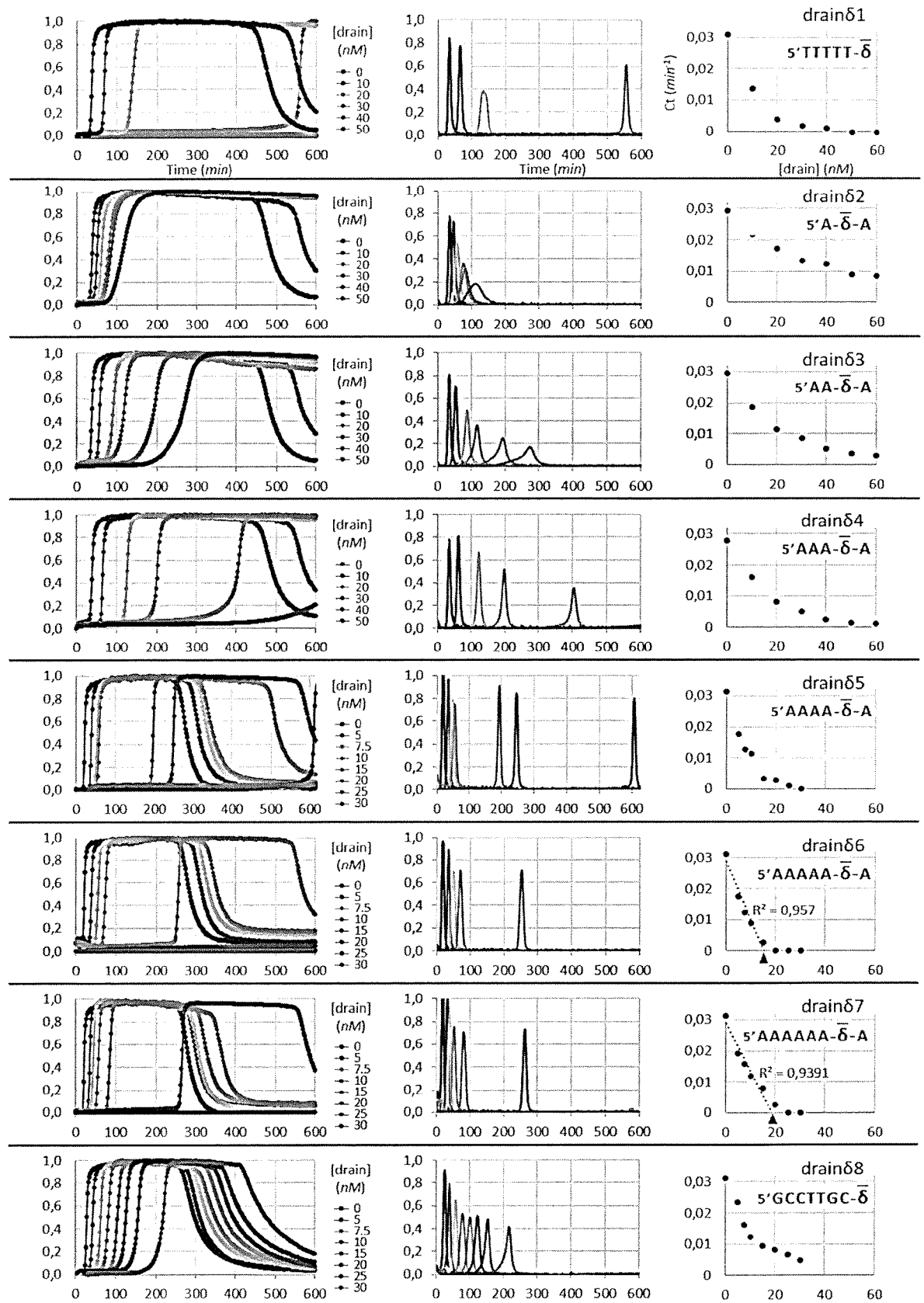
FIG. 10 is a set of graphs showing the effect of various pseudo-template designs.
Figure 12:
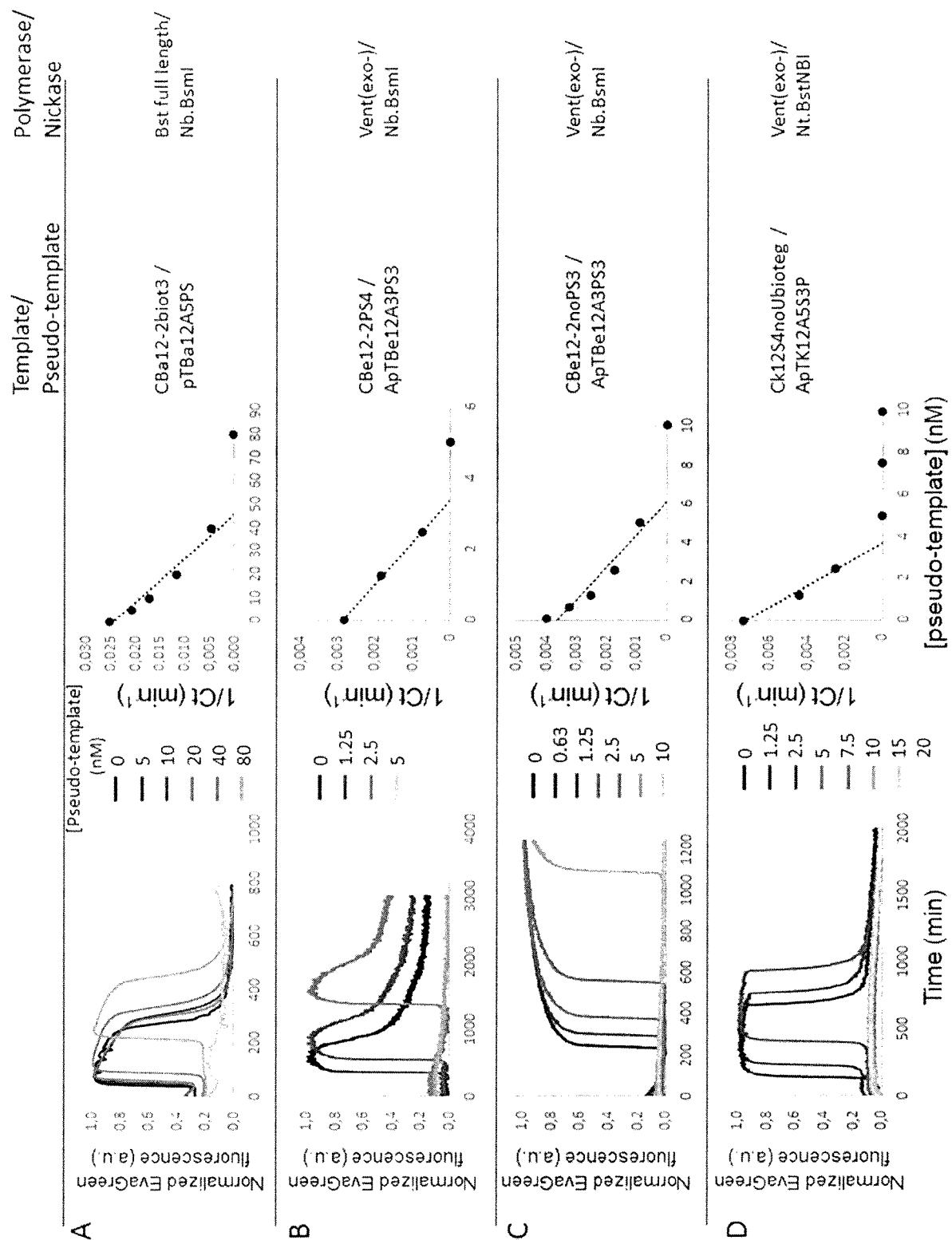
FIG. 12 is a set of graphs showing background amplification removal with template and pseudo-template pairs.

FIG. 10 is a set of graphs showing effect of various pseudo-template designs. FIG. 11 is a first table showing experimental condition in Example 5. FIG. 12 is a set of graphs showing background amplification removal with template and pseudo-template pairs. FIG. 13 is a second table showing experimental condition in Example 4. FIG. 14 is a third table showing experimental condition in Example 4. FIG. 15 is a fourth table showing experimental condition in Example 4. FIG. 16 is a fifth table showing experimental condition in Example 5.

In the present Example, it will be shown that the effect does not depend on the particular properties of the enzymes used in the amplification process. First, we test another nicking enzyme to drive the amplification process (Nt.BstNBI) and we check that pseudo-templates are still able to remove the background amplification. We thus show that the approach is also valid for amplification systems using Nt.BstNBI as the nicking component.

The relative arrangement of the recognition and cleavage site is different between Nt.BstNBI and Nb.BsmI (Nb.BsmI is the nickase used in Examples 1-4). For Nt.BstNBI, the recognition site of the nickase is completely contained within the sequence of the input and the nicking position is four nucleotides downstream of the recognition site. As a consequence, the recognition site has to be deactivated on the pseudo-template sequence (if not, then the extended product on the pseudo-template could be nicked back to its original trigger length). It was shown that this is obtained by a dT→dU mutation on the bottom (template, non-nicked) strand of the recognition sequence, therefore all pseudo-templates were designed with this mutated sequence (NPL 18b).

NPL 18b: Alexandre Baccouche et al., "Dynamic DNA-Toolbox Reaction Circuits: a Walkthrough," Methods, February 2014, doi:10.1016/j.ymeth 0.2014.01.015.

Also one should be careful that the nicking enzyme Nt.BstNBI cannot efficiently process blunt recognition sites. It is found that at least one closed GC or CG pair is required 5' of the GAGTC recognition site (in the case of an open terminal AT pair it was found that the dangle energy brought by an additional mismatched or dangling A led to correct nicking rates). This constraint limits the number of bases that can be removed from the input side of the template without affecting the nicking rate. Here two bases are removed from the 12-bases repeat sequence, so the additional closing pair is present.

A master mix with the composition shown in a table of FIG. 11 is created.

This mixture is complemented with different concentrations of pseudo-template with various designs (drainδ1-8, in order: pTk12T5S4P=T*T*T*T*T-CAATGACUCCTG-P— (corresponding to SEQ ID NO: 20); ApTk12A1SUP= A*C*A*ATGACUCCTG-A-P—(corresponding to SEQ ID NO: 21); ApTk12A2SUP=A*A*C*AATGACUCCTG-A-P—(corresponding to SEQ ID NO: 22); ApTk12A3PS A*A*A*-C*AATGACUCCTG-A-P—(corresponding to SEQ ID NO: 23); ApTk12A4SUP= A*A*A*ACAATGACUCCTG A-P—(corresponding to SEQ ID NO: 24); ApTk12A5SUP=A*A*A*AA CAATGAC8CCTG A-P—(corresponding to SEQ ID NO: 25); ApTk12A6SUP=A*A*A*AAA CAATGACUCCTG A-P, —(corresponding to SEQ ID NO: 26)). The amplification is monitored in real-time with the double-strand specific intercalating dye EvaGreen and no trigger is introduced in the initial reaction mix.

FIG. 10 illustrates the results of the experiments using Nt.BstNBI as the nicking enzyme. Very similar to the case of the systems running on Nb.BsmI, in the absence of pseudo-template, and even in the presence of the exonuclease ttRecJ, the background amplification is always observed (The fact that the curves come back toward the base line after some time in the high state is due to the exhaustion of available dNTPs: when too little or no more dNTPs are available in the mixture, the production of new triggers stops, and the digestion of existing triggers by the exonuclease decreases their concentration so that the fluorescent signal starts to decrease. The length of the time spent in the plateau can be simply tuned to any desired time by adjusting the initial concentration of dNTP in the mixture). However, various pseudo-templates are able to stabilize the 0 state when present in sufficiently large amounts. By comparison with the case of Nb.BsmI, for the same concentration of amplification template, larger concentrations of pseudo-template are typically required for the complete removal of background amplification.

Second, some other polymerases, such as Bst full length and Vent(exo-), were tested in combination with these two different nickases. Experimental conditions are given in the tables of FIG. 13-16, and the results are shown in FIG. 12. It is found that, in every case, there is a concentration of pseudo-template that is able to abolish the background amplification and stabilize the non-amplifying state. As expected, this concentration depends on the details of the enzyme used and the design or modifications of the amplification template and pseudo-template, because those molecular details will affect the leak rate and the efficiency of the pseudo-template.

The fact that various nickases, various polymerases, various sequences for the amplified species, and various design for the amplification template and pseudo-template can be used proves the generalization of the present approach. It shows that it is not linked to a particular chemical property of some compounds such as high fidelity, high specificity or high purity, but is a new and general principle to delay and even completely remove background amplification using the principles of dynamical systems. We move from an amplify-only exponential amplification system, which is bound to initiate amplification, toward a bistable system, which can stay indefinitely in any one of two alternative states, but also switch from one to the other.

FIG. 12 demonstrates background amplification removal with template and pseudo-templates pairs using various combinations of polymerase and nicking enzyme. FIG. 12A illustrates a case using the DNA polymerase Bst full length and the nickase Nb.BsmI. FIGS. 12B and 12C illustrate cases using the DNA polymerase Vent(exo-) and the nickase Nb.BsmI. FIG. 12D illustrates a case using the DNA polymerase Vent(exo-) and the nickase Nt.BstNBI. In each of FIG. 12A-12D, the left end illustrates the time traces of each sample containing a varying concentration of pseudo-template, the second illustrates the linear correlation between the pseudo-template concentration and 1/Ct, the third illustrates templates and pseudo-templates used, and the right end illustrates polymerase and nickase used.

Next will be described Example 6, regarding ultrasensitive detection of miRNA targets or analogs using the pseudo-template approach.

Figure 17:
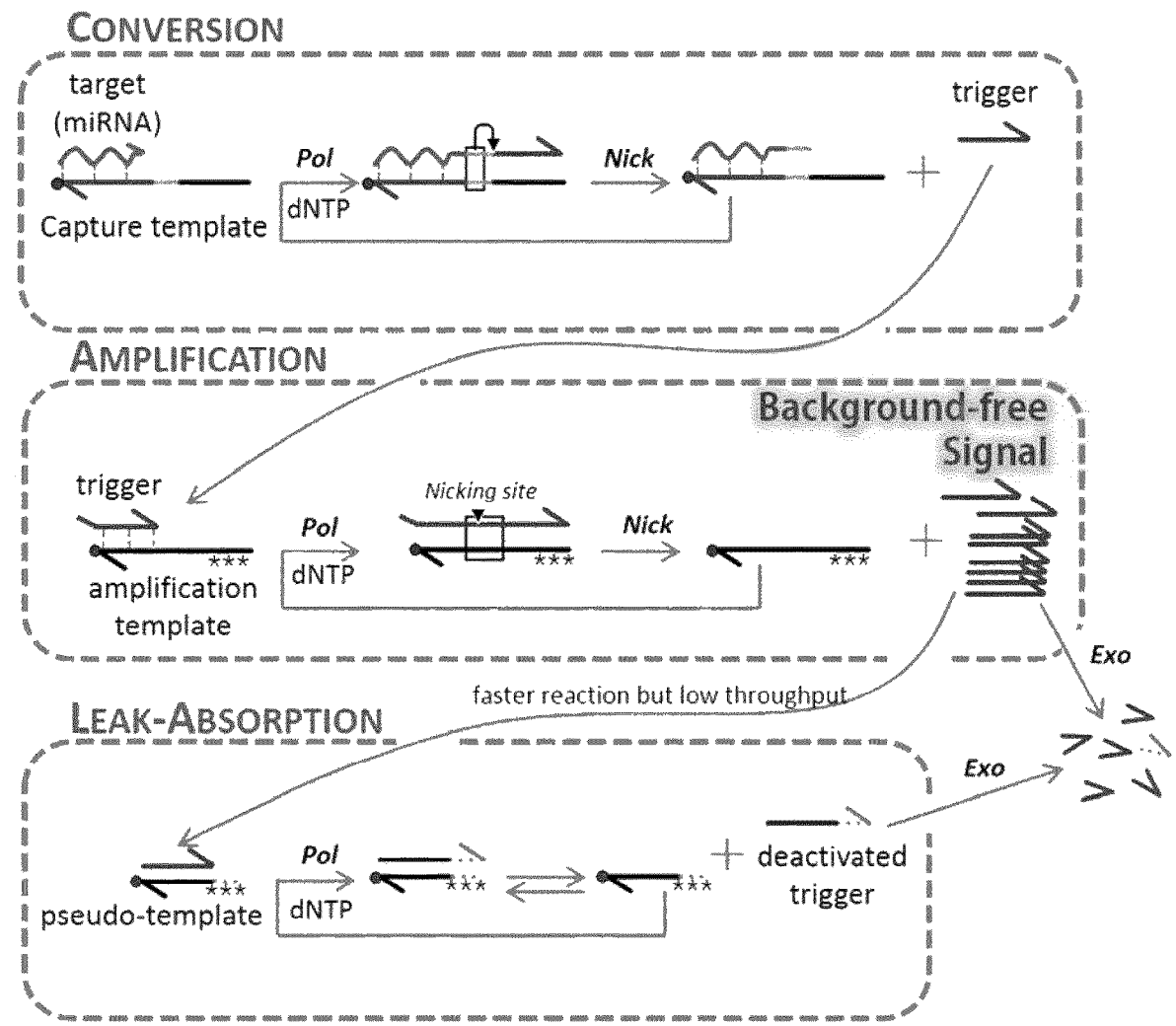
FIG. 17 is a set of schematic views showing general principle for ultrasensitive detection of low copy number targets.

FIG. 17 is a set of schematic views showing general principle for the use of background-free amplification loops for the ultrasensitive detection of low copy number targets.

Figure 18:
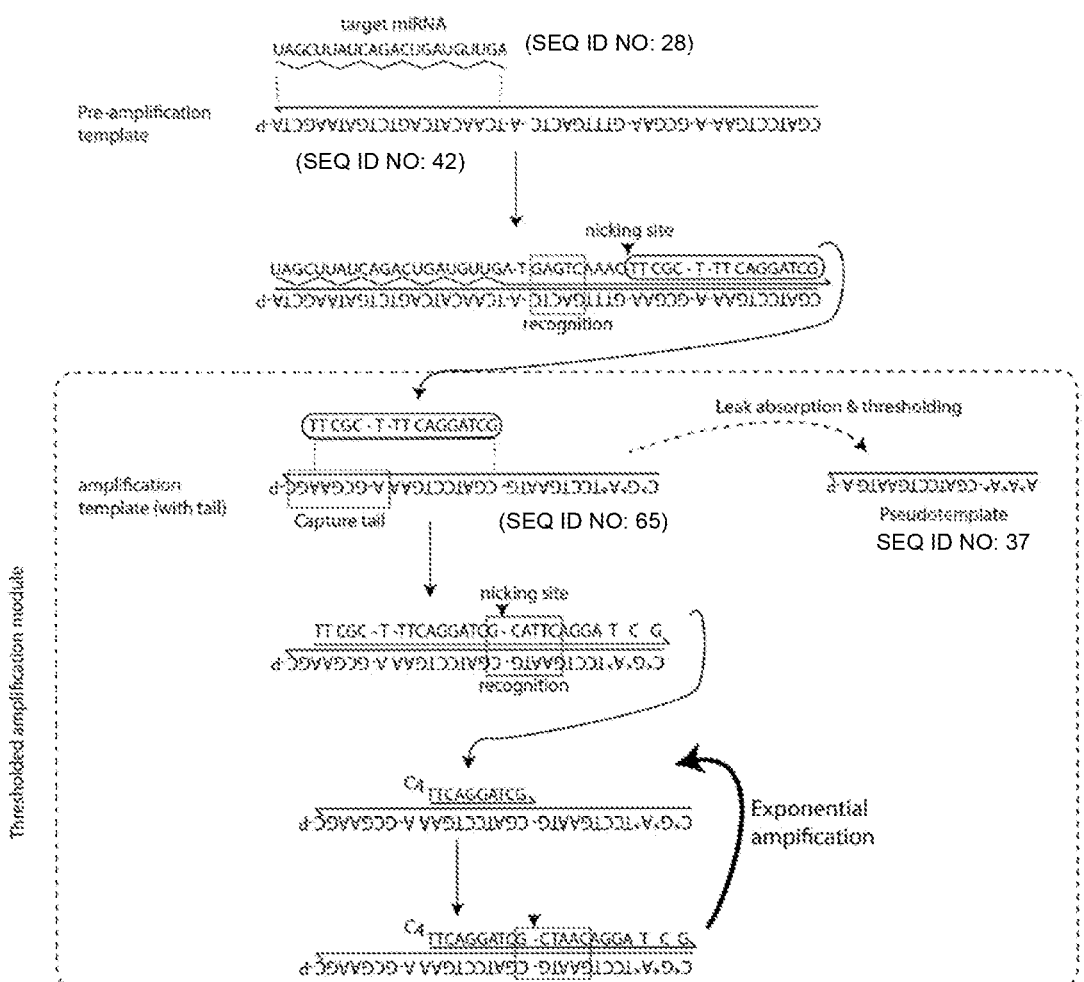
FIG. 18 is a set of schematic views showing strand design and working principle for ultrasensitive miRNA detection with tailed amplification templates.
Figure 20:
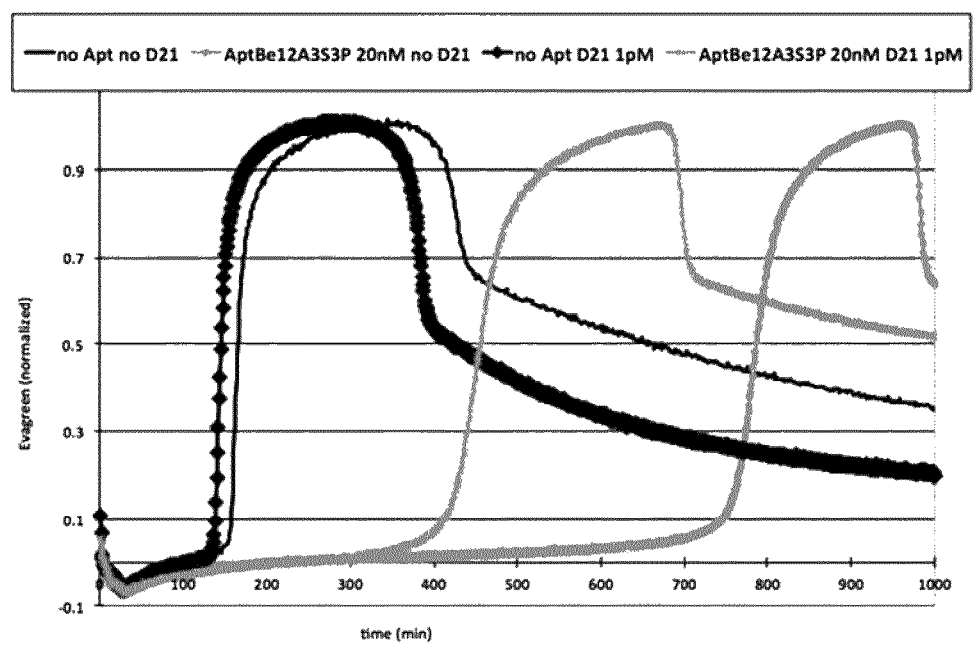
FIG. 20 is a set of graphs showing detection of the DNA analog of miR-21.
Figure 21:
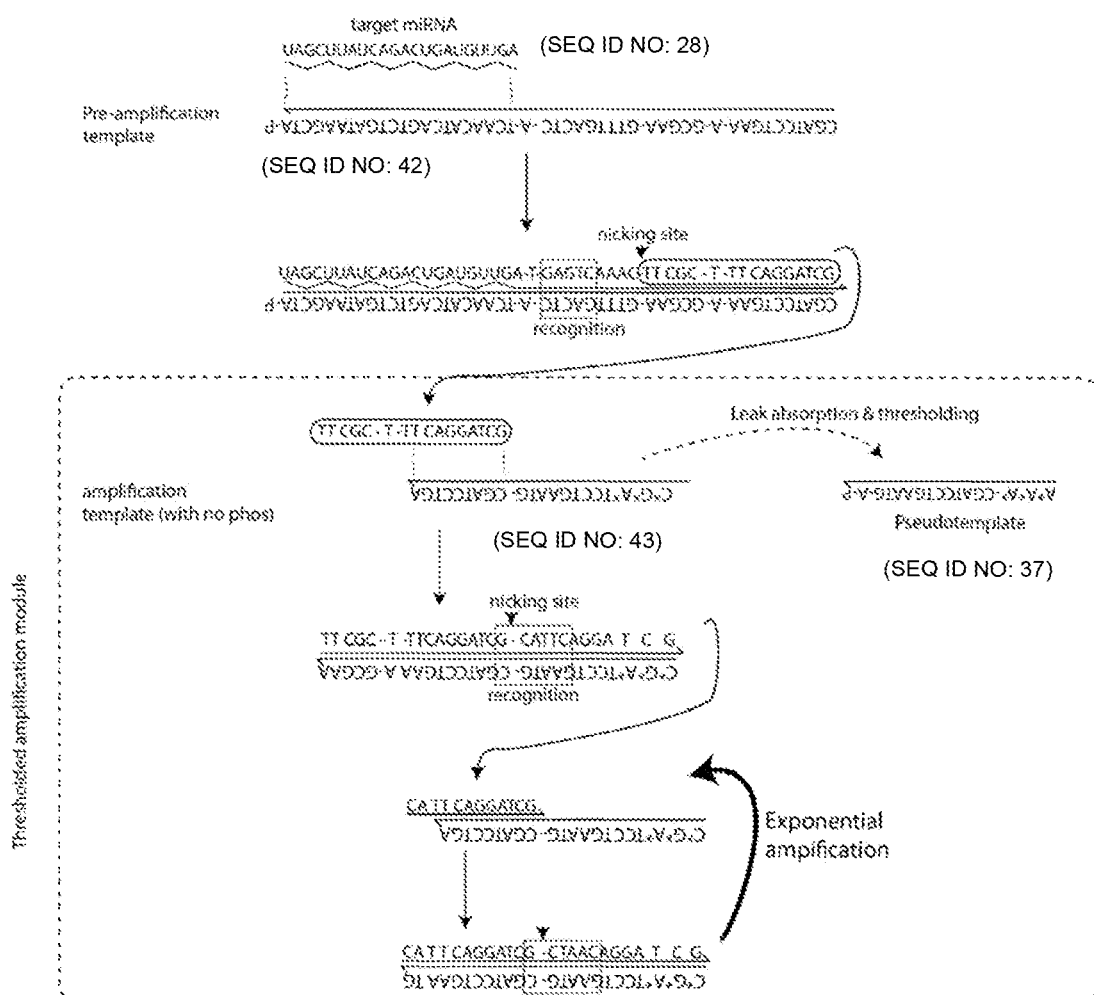
FIG. 21 is a set of schematic views showing strand design and working principle for ultrasensitive miRNA detection with un-blocked amplification template.
Figure 23:
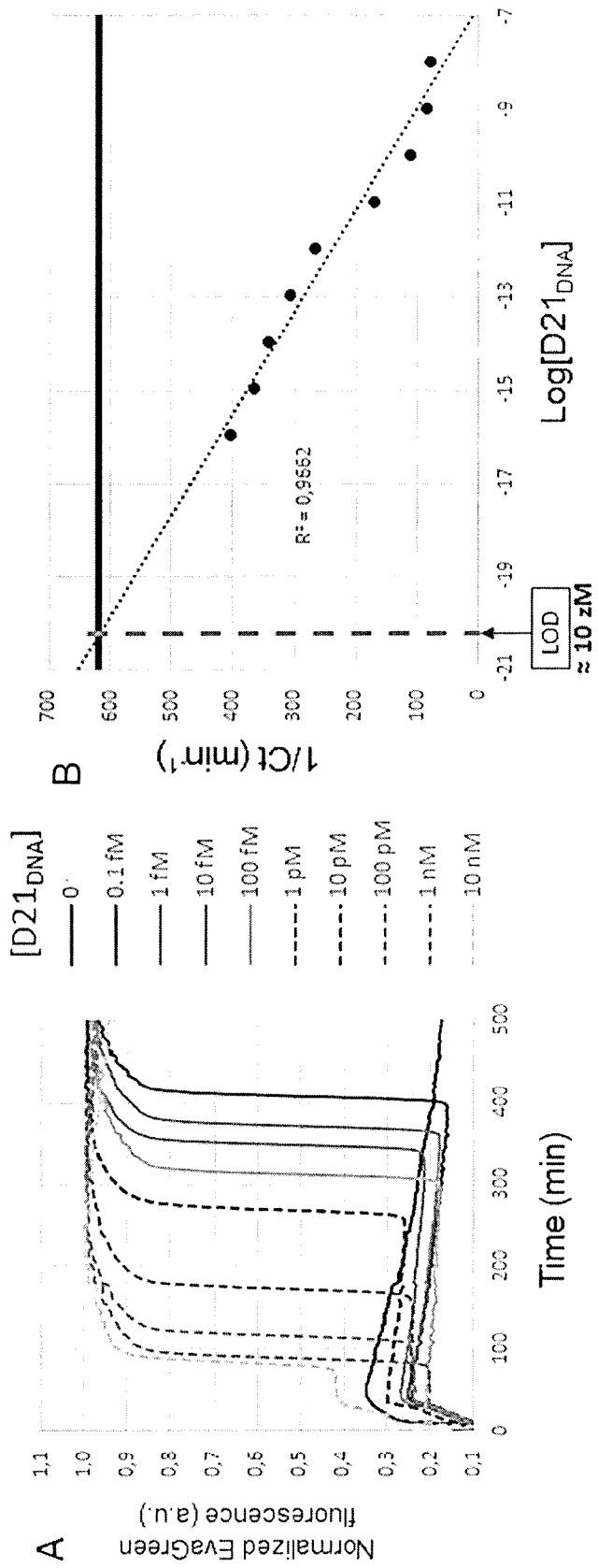
FIG. 23 is a set of graphs showing measurement of the limit of detection.
Figure 24:
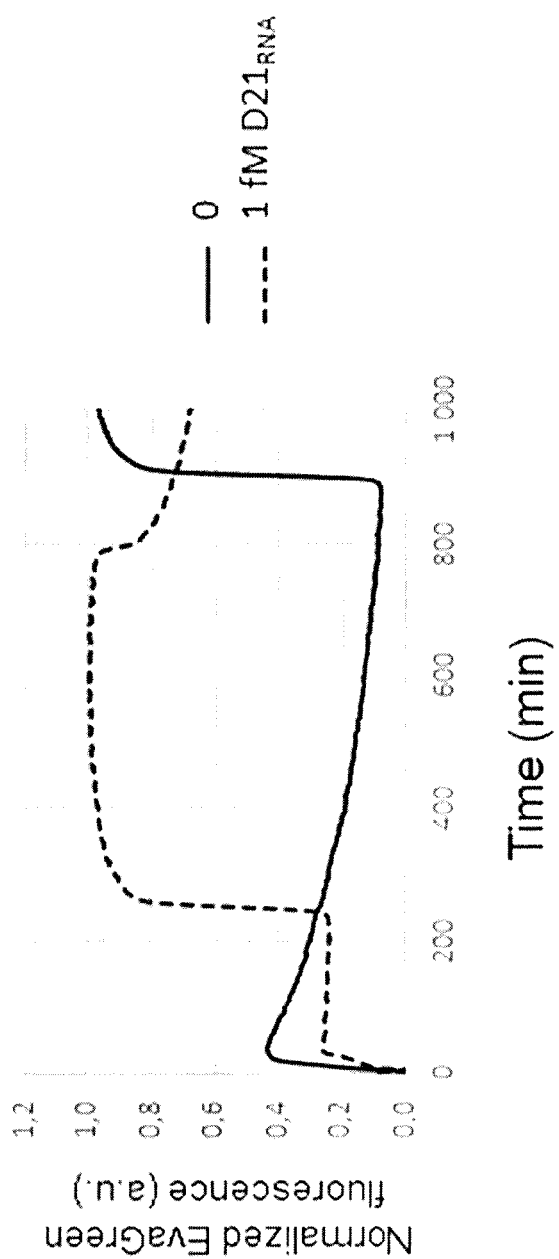
FIG. 24 is a set of graphs showing robust discrimination of the presence/absence of micro RNA target miR-21 at 1 fM.

The basic concept is that the low copy number target is used to force the amplification loop beyond its threshold, and thus triggers amplification. In comparison to various other methods, such a PCR, LAMP, RPA, RCA, NASBA and the likes, the low copy number target itself is not amplified. In this example, we propose two approaches to use the low copy number target to force the amplification loop beyond its threshold. FIG. 18 is a set of schematic views showing strand design and working principle for ultrasensitive miRNA detection with tailed amplification templates. FIG. 19 is a first table showing experimental condition in Example 6. FIG. 20 is a set of graphs showing ultrasensitive detection of the DNA analog of miR-21. FIG. 21 is a set of schematic views showing strand design and working principle for ultrasensitive miRNA detection with un-blocked amplification template. FIG. 22 is a second table showing experimental condition in Example 6. FIG. 23 is a set of graphs showing the evaluation of the limit of detection. FIG. 24 is a set of graphs showing robust discrimination of the presence/absence of micro RNA target miR-21 at 1 fM.

To show the potential applications for robust and sensitive detection of nucleic acids, we show here that the background-free exponential loop described above can be connected with a conversion template designed to sense an arbitrary (decided by the experimenter) sequence. The general principle for ultrasensitive detection of low copy number targets, using the background amplification-free system described in the present disclosure, is shown in FIG. 17. This design is generic and modular because only the conversion template needs to be adapted if the assay is re-purposed to a new target. As an example, a miRNA (miR-21), or its DNA analog, is selected as the target here, but it should be understood that many other sequences of interest (in particular any other miRNA or RNA sequence or DNA sequence) could be detected using the same design.

One exemplary assay design (design 1) goes as follows: a sequence for the amplification loop (amplification sequence: Be12=CATTCAGGATCG, —corresponding to SEQ ID NO: 4) is selected and the amplification template (with deleted bases on the input side) and the corresponding pseudo-template are designed, then a small tail is added on the 3' side of the amplification template. This tail will be used to bind some sequences with a higher affinity than the amplification sequence. Additionally a conversion template is created, whose input side corresponds to the target sequence (here the miRNA of interest), and output sequence is the complementary to the input side of the amplification template, including the 3' tail that is not part of the dual repeat structure. The design is schematized in FIG. 18. A mixture with the composition shown in a table of FIG. 19 is prepared.

The conversion template is inserted at a low concentration in the mixture to avoid the generation of leaky products by this strand. The mixtures (with or without pseudo-template) are separated in two tubes and 0 (pure milliQ water) or 1 pM of the target species (the DNA strand corresponding to miR-21 sequence: $D21_{DNA}$=TAGCTTATCAGACT-GATGTTGA, corresponding to SEQ ID NO: 27) are spiked in the mixtures just before incubation. The results are shown in FIG. 20, where, in the presence of the pseudo-template, the 1 pM concentration is easily distinguished from the background amplification, because the target positive tube provides a detectable signal starting from t=400 minutes, whereas the negative control does not amplify before 700 minutes. In the absence of pseudo-template, the tubes with or without target amplify almost simultaneously, proving that the pseudo-template is necessary for robust and sensitive target/no target discrimination. It is clear that such an assay can be very easily redesigned toward any other miRNA or nucleic acid of interest, as it is sufficient to change the input sequence of the conversion template to be the complementary to the targeted miRNA or sequence. No modification of the thresholded amplification module is required. It is also well known that many polymerases can use indifferently DNA or RNA sequences as primers, so this result should be valid for the detection of the true miRNA, besides its DNA analog. This is in fact demonstrated in the following experiments.

Another assay design (design 2) based on similar principle uses non-blocked amplification templates (i.e. with no 3' phosphate or other 3' modification) with deletions. These templates can extend to capture efficiently the signals emitted by the conversion template. This approach is schematized in FIG. 21. A mixture with the composition shown in a table of FIG. 22 is prepared.

To evaluate the limit of detection of this approach, the mixture is spiked with various concentrations of the DNA analog of miR-21 ($D21_{DNA}$=TAGCTTATCAGACT-GATGTTGA—corresponding to SEQ ID NO: 27), ranging from 1 nM to 1 fM.

It is noteworthy that the extrapolated limit of detection is obtained around 10 zM, which represents less than one target molecule in a 10 µL test tube. Therefore, it appears theoretically feasible to detect a unique molecule in a test tube.

Then a similar experiment is performed to detect the synthetic oligoribonucleotide miR-21, which is the true biological target. The experimental conditions are the same as above. The system is initiated with 0 or 1 fM of miR-21 (sequence miR-21=UAGCUUAUCAGACUGAU-GUUGA—corresponding to SEQ ID NO: 28). FIG. 24 represents the time trace recorded for each of the two samples. It clearly demonstrates that this system easily discriminates the sample containing the RNA target, even at a very small concentration, from the control sample (no target). Note that in both experiments, the inclusion of the conversion template in the mixture restores a degree of self-start (background amplification), but this one happens so late that it does not limit the sensitivity for practical purpose. For example in FIG. 23, a linear regression can be used to estimate the limit of sensitivity of the assay, which is estimated at 10 zM, i.e. 6 molecules of target per milliliter. This phenomenon also appears to be dependent on the structure of the conversion template, and Example (ultrasensitive and ultra-specific) described below shows a case where the conversion template does not generate any detectable background amplification.

Next will be described Example 7, regarding multiplexing the background-free detection modules using specific fluorescent reporting.

FIG. 25 is a set of schematic views showing multiplexing the detection modules with sequence-specific fluorescent reporting. FIG. 26 is a table showing experimental condition in Example 7.

Performing multiple detection in a single tube allows to decrease the preparation time and the reagent cost of assays and is a commonly used technique in analytical PCR (quantitative PCR). However, multiplexing capability is more rare in the case of isothermal amplifications. In particular it has never been reported for polymerase/nickase exponential amplification schemes, probably because of their strong tendency to display untriggered amplification. Nevertheless, a parallelized assay has been reported for the simultaneous detection of Let-7a (corresponding to SEQ ID NO: 30) and mir21—(corresponding to SEQ ID NO: 28) by EXPAR but it actually uses two simplex assay (meaning that the sample is split and the detection of each target is conducted in separated test tube) (see NPL 20). To detect simultaneously two targets within a unique sample using the background-free amplification modules described above, we tested the construction of a duplex system based on a mixture of two independent template/pseudo-template systems (see FIG. 25). The sequences of the two triggers and the two amplification templates are designed to avoid cross-binding, and the pseudo-templates are constructed according to the rules introduced above. Relative concentrations are also inferred from the previous results, only keeping the total concentration of autocatalytic templates constant to mitigate enzyme load (see, for example, NPL 19). Additionally, two fluorescent dyes are attached as N-quenching reporters (see, for example, NPL 16) on the amplification templates in order to generate species-specific fluorescence reporting (using state of the art knowledge). A mixture with the composition shown in a table of FIG. 26 is assembled.

NPL 19: van Roekel H W H, et al. (2014) Automated Design of Programmable Enzyme-Driven DNA Circuits. ACS Synth Biol:141110070157007.

NPL 20: Zhang Y, Zhang C Y, Sensitive Detection of microRNA with Isothermal Amplification and a Single-Quantum-Dot-Based Nanosensor, Anal. Chem (2012).

When the four oligonucleotides are combined in a tube, the fluorescence signals show that, in the absence of any target, no amplification happens, for up to 1000 minutes. However, if either one, or both of the targets (Bc12=CATTCTGGACTG; —(corresponding to SEQ ID NO: 29) Be12=CATTCAGGATCG—(corresponding to SEQ ID NO: 4)) are inserted at 20 nM in the mixture, they are detected and amplified specifically by the corresponding background free amplification module, without affecting the other module (see FIG. 25). FIG. 25A illustrates that a duplex detection assay can be constructed by combining two independent detection modules as schematized, and monitored with two fluorescent dyes attached to the templates. FIG. 25B illustrates change over time of BMN3 and Cy3.5 fluorescence after injection of the four possible combinations of the two targets (no trigger; Bc12 only; Be12 only; Bc12 and Be12). It is noteworthy that even when one module switches to the high state, the pseudo-template of the second amplification loop is still able to buffer the perturbations and maintain its module in the low state.

This shows that it is possible to perform multiple detections simultaneously in the same mixture and to build multiplex assays using the present disclosure.

Next will be described Example 8, regarding the generality of the approach to detect low concentrations of various detect nucleic acid targets, and its ultrasensitive and ultraspecific character.

FIG. 27 is a set of graphs showing experimental results concerning the detection of miRNA miR92a. FIG. 29 is a set of schematic view showing the specificity of the detection of a miRNA target compared to mismatching analogs. Each of FIGS. 28 and 30 is a table showing experimental condition in Example 8.

FIG. 27 displays an experimental set up to detect the RNA target miR92a (cf. FIG. 28 for experimental condition). It uses the same design as the one presented in Example 6 second design (FIG. 21) and comprises the following elements: i) an unphosphated autocatalytic template shortened by three nucleotides in its 3' part, CBe12-3noPS3 (SEQ ID NO: 43) which uses the nickase Nb.BsmI (sequences are given below), ii) the cognate pseudo-template AptBe12A3S3P (SEQ ID NO: 37), iii) the conversion template 92atoF5TBe12PS0 (SEQ ID NO: 49), which uses the nickase Nt.BstNBI. The 3-component system is contacted with the 4-enzyme processor (polymerase Vent(exo-), nickases Nb.BstBsmI, Nt.BstNBI and exonuclease ttRecJ) and incubated with a concentration of the RNA target miR92a ranging from 10 aM to 10 nM (plus negative control). FIG. 27A represents the time-traces for each sample recorded with EvaGreen. FIG. 27B shows the plot of the corresponding Cts as a function of the target concentration. While the control sample (without target) stays off on for the experiment duration—proving again the total removal of the unspecific background amplification—samples containing the target sequentially switch on according to the miR92a concentration with a linear relationship. This set of experiments shows that 10 aM concentration of the target can be detected very robustly compared to the negative control, which demonstrates complete removal of the background amplification, even in the presence of a conversion template. It also suggests that much smaller concentrations could be detected as well. This result supports the generality of the approach and its efficiency for the detection of a variety of clinically relevant RNA targets.

Figure 29A:
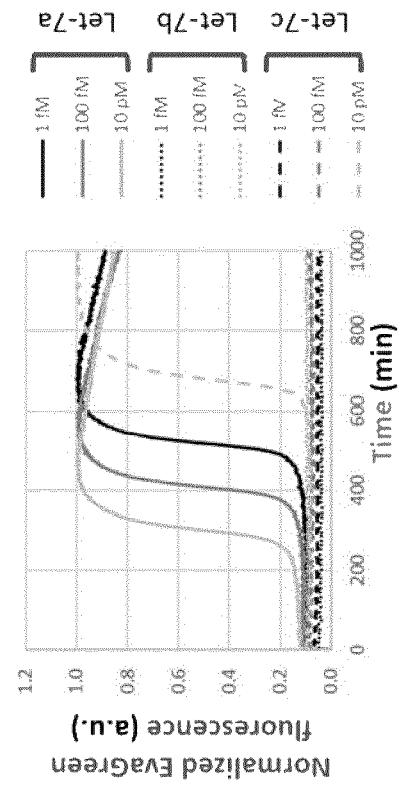
FIG. 29 is a set of schematic view showing the specificity of the detection of a miRNA target compared to mismatching analogs.
Figure 29B:
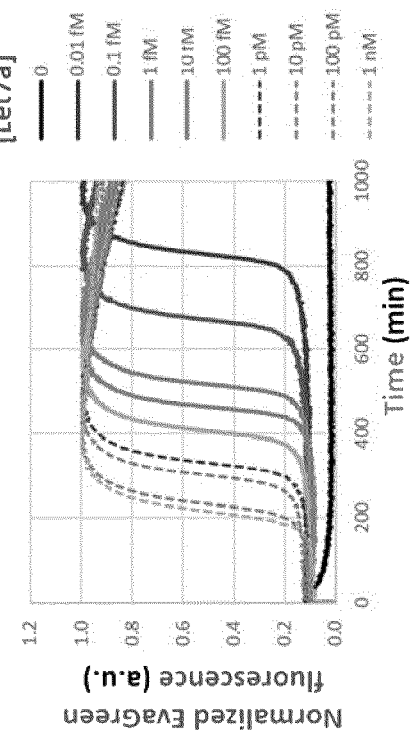
Figure 29C:
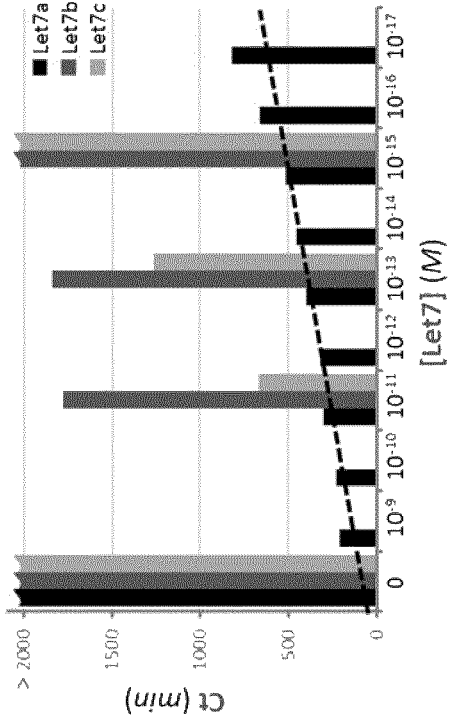
Figure 29D:
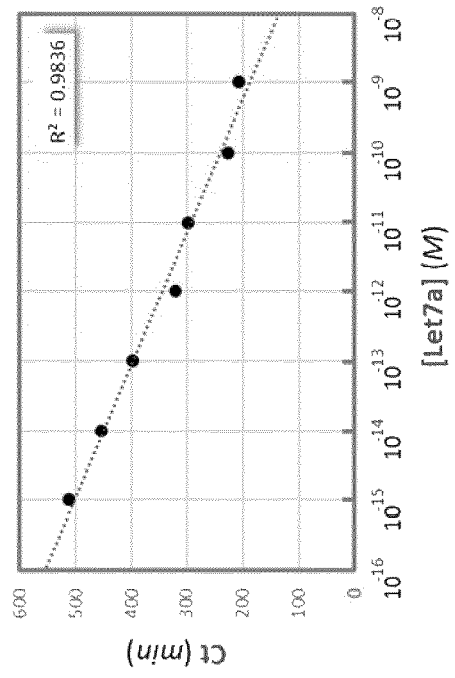

When designing a detection scheme, one needs to check not only the sensitivity of the assay but also its specificity, that is, its ability to separate the target from a background of similar compounds. Here we look at the ability of the system to separate a given target from its close analogs. We show that the selectivity is extremely good, with at least 10000 times difference in sensitivity for a single mismatch. FIG. 29 is a set of schematic views showing experimental results for the specific detection of the miRNA Let7a (see FIG. 30 for experimental condition). It involves a 3-strand assay design similar to the one of Example 6 design 1 (FIG. 18): the shortened autocatalytic template CBa12-2AULP (SEQ ID NO: 51), the pseudo-template ApTBa12A3S3P (SEQ ID NO: 52) and the conversion template Let7atoF5TBa12 (SEQ ID NO: 50). The 3 DNA strands are contacted with the 4-enzymes processor (polymerase Vent(exo-), nickases Nb.BstBsmI, Nt.BstNBI and exonuclease ttRecJ) and incubated with the cognate target Let7a (sequence=UGAGGUAGUAGGUUGUAUAGUU, SEQ ID NO: 30) or the mismatching microRNA analogs Let7c (sequence=UGAGGUAGUAGGUUGUAUGGUU, SEQ ID NO: 32) and Let7b (sequence=UGAGGUAGUAGGUUGUGUGGUU, SEQ ID NO: 31), which have 1 and 2 mismatches respectively). FIG. 29A and FIG. 29B represent the time-traces and the plot of Cts for each sample containing an increasing concentration of the correct target Let7a. As in FIG. 27, the experiment shows a linear correlation between the time of amplification (Ct) and the concentration of target, down to 10 aM pf target while the negative control does never produce amplification. FIG. 29C shows the time-traces of independent samples containing either the matching target Let7a or the mismatching analogs Let7b or Let7c (1 fM, 100 fM and 10 pM). Comparatively, samples containing Let7a amplify much before than samples triggered with Let7b or Let7c, even if the latter are present at high concentration. As a proof of the high specificity of the assay, the Ct for the sample withl fM of Let7a is around 500 minutes while 10 pM (namely 10000 times more) of the analog species Let7c (which has a single mismatch) is still 200 minutes later, below 700 minutes. FIG. 29D displays the amplification time (Ct) for the various miRNA, emphasizing the very high specificity of the assay. As a conclusion, the current embodiment is able to efficiently differentiate the correct target from single and double mismatched analogs.

Next will be described Example 9, regarding adjusting the threshold concentration of trigger necessary to initiate amplification.

Figure 31:
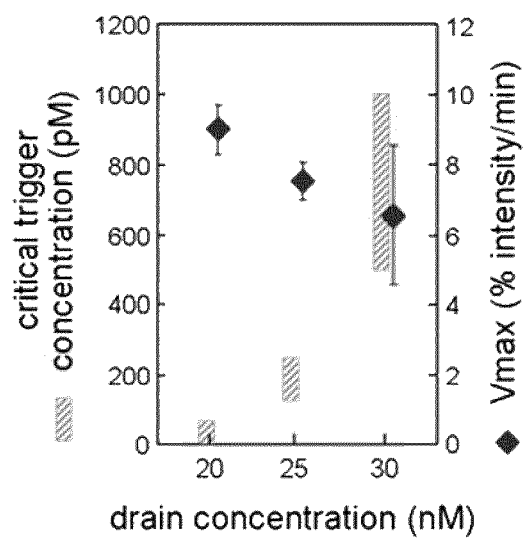
FIG. 31 is a graph showing experimental results supporting the existence of a tunable threshold.

FIG. 31 is a graph showing experimental results supporting the existence of a tunable threshold.

For a given template/pseudo-template pair in the bistable regime, we show that the concentration of trigger required to switch the system to the high state increases with the concentration of the pseudo-template (see FIG. 31). FIG. 31 illustrates that a tunable threshold can be implemented with pseudo-template, at the cost of amplification rate. In FIG. 31: 50 nM of autocatalytic template ßtoß is incubated with 20, 25 or 30 nM of pseudo-template ß and various concentrations of trigger ß; the hashed bars indicate the range, within which the threshold trigger concentration required to switch the system to the high state can be found; the blue dots indicate the maximum amplification rate. At the same time, the maximum amplification rate decreases with increasing pseudo-template concentration as the latter starts outweighing the positive feedback loop. In other words, systems with lower threshold are also more responsive.

Next will be described a computational analysis of the principles that enable the template/pseudo-template approach presented here to eliminate background amplification.

FIG. 32 is a set of schematic views showing a strategy to remove background amplification and some kinetic simulations of the behavior of the system, based on numerical integration of the corresponding ODE (see NPL 18b).

Figure 32A:
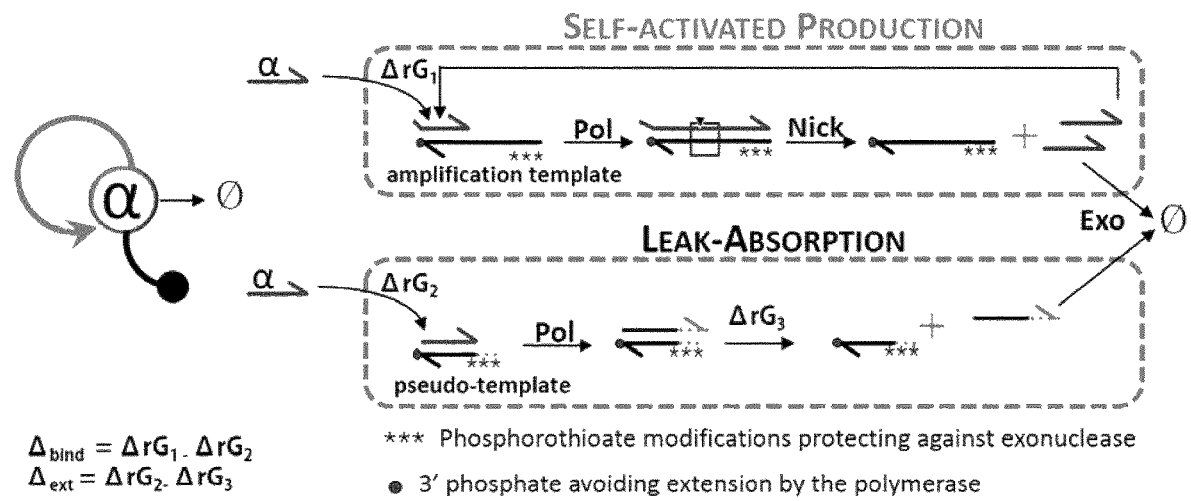
FIG. 32 is a set of schematic views showing a strategy to remove background amplification and some kinetic simulations of the behavior of the system, based on numerical integration of the corresponding ODE (Ordinary Differential Equation)

FIG. 32A presents a strategy to remove the background amplification and stabilize the non-amplifying state. The approach is based on a "pseudo-template", which elongates inputs very much like a regular DNA toolbox template, but cannot be nicked. The elongated input slowly melts away, but its new 3' tail, if correctly designed, now forbids any further priming on its cognate template—it has been wasted. This slow de-hybridization step also restores the pseudo-template, which therefore acts as a catalyst, not a substrate. Assuming enzymes are in their linear regime, the first-order rate associated with the pseudo-template pathway is controlled by the pseudo-template concentration and by the duplex formation—hence by the binding affinity of the pseudo-template relative to that of the amplification template. As mentioned above, this can be adjusted, for example by removing a few bases on the binding site of the template. In turn, the maximum deactivation rate by the pseudo-template will depend on the slow de-hybridization step, and hence will be controlled by the stability increase brought by tailing the input along the pseudo-template. Thus two design parameters are naturally defined, which are the thermodynamic binding difference between production and pseudo-templates ($\Delta_{bind}$) and the increase in stability associated with extension on the pseudo-template ($\Delta_{ext}$).

Figure 32B:
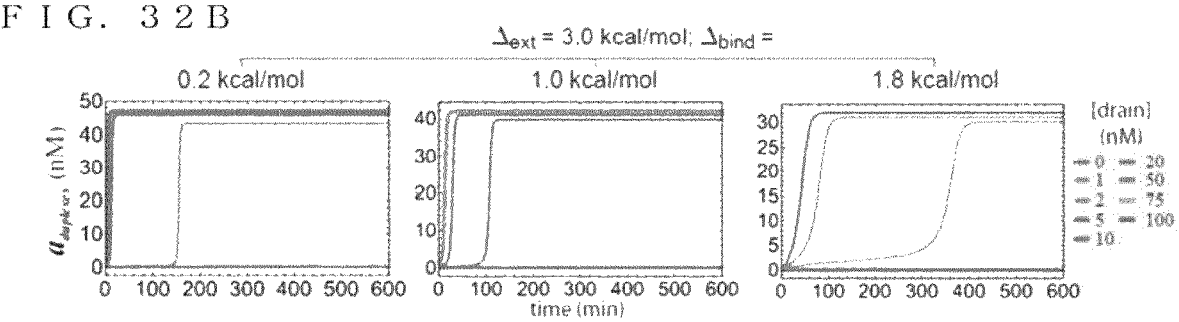
Figure 32C:
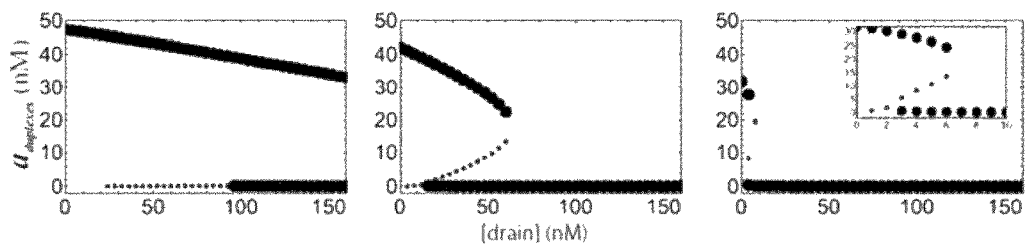

Because the set of enzymatic and DNA hybridization reactions involved in the DNA toolbox are well mapped, it is possible to build a complete, quantitative kinetic model that keeps these two energy differences as free parameters (according to the method disclosed in NPL 18b). This ODE model contains 15 variables, one for each DNA strand or DNA complex. A numerical search for bistability, by applying small perturbation to the system in the non-amplified state, yields the following conclusions. First, bistability can be obtained over a wide range of the $\Delta_{bind}/\Delta_{ext}$ space, provided $\Delta_{bind}$ is above a minimal value, and enough pseudo-templates are included (FIG. 32B). Second, pseudo-templates with lower $\Delta_{ext}$ are more efficient. However, the requirement of fast capture of triggers imposes a minimal concentration of pseudo-templates, which may negatively affect the amplification rate, if pseudo-templates turnover too fast (i.e. low $\Delta_{ext}$).

These numerical conclusions are precisely in line with the result of the experiments described in Example 1 to 5. In the absence of pseudo-template, the simple, autocatalytic loop shown in FIG. 28A induced by a repeat template produces first-order amplification with an intrinsically unstable 0 state: as already reported (see, for example, NPL 5) and shown in Example 1, even in the absence of trigger, and irrespective of the $\Delta_{bind}$ value and the presence of an exonuclease, a system capable of exponential amplification will self-start, initiated by spurious polymerization or impurities. However, when a sufficient amount of pseudo-template is incorporated in the system, it could be observed that the 0 state became stable (see FIG. 4 in Example 2 or FIG. 8 in Example 3 for example). At the same time, amplification could be readily observed after triggering with a small concentration of trigger strands. The experimental plots of Ct versus the concentration of pseudo-templates are typical of the saddle node bifurcation observed in the numerical simulations (FIG. 32C), where bistability is suddenly observed above a critical concentration of pseudo-template.

Alternative designs with different $\Delta_{bind}/\Delta_{ext}$ values were tested and it was found that a rather good agreement with the expectations: pseudo-template requires at least a two-base tail to efficiently deactivate the triggers; above this length, pseudo-template designs with lower $\Delta_{ext}$ are more efficient, i.e. lead to bistability with lower concentrations (see FIG. 8B in Example 3). Still in line with predictions, a minimal value of $\Delta_{bind}$ appears necessary for bistable behavior with reasonable pseudo-template concentrations, but excessive destabilization of the autocatalytic template yields unresponsive systems, even if they are very easily brought to the bistable regime (see FIG. 8C in Example 3).

These numerical simulations therefore agree with the experimental results and support the fact that reduction and complete removal of background amplification are due to the transition from a monostable exponential amplification system toward a bistable system. Moreover, because this transition is controlled by experimental parameters, such as the sequence of the amplification template and the pseudo-template, or their respective concentrations, it is possible to obtain systems that are both devoid of any background amplification and suitable for ultrasensitive and ultra-specific and multiplexed detection of nucleic acids, as shown in Examples 6, 7 and 8 and 12.

Multiplex detection assays of micro RNA by a background-free amplification method according to the invention using reporting probe are described in Example 10 below and the obtained results are shown in FIGS. 33 to 37.

Figure 33:
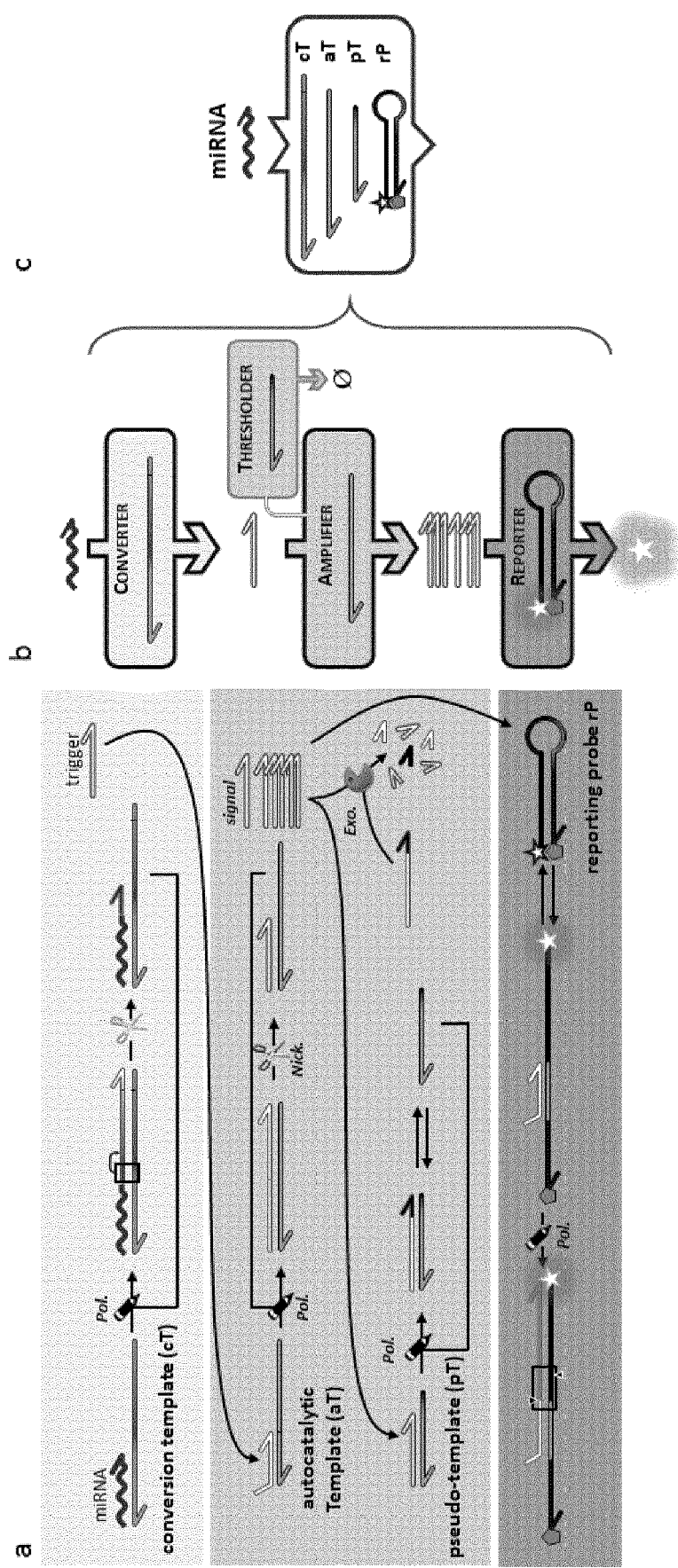
FIG. 33 is a synthetic DNA circuit for the detection of microRNA. a. General schema. b. Simplified representation of the connectivity of the DNA circuit. c. Schematic of a DNA circuit dedicated to the detection of one particular microRNA.

FIG. 33 shows a general presentation of synthetic DNA circuit for the detection of microRNA according to the invention using reporting probe. A bistable switch made of an autocatalytic template (which catalyzes the exponential amplification of the signal strands) and a pseudo-template (which deactivates the signal strand produced by leaky reactions) is connected upstream to a conversion template (which binds the target and in turn produce triggers for the autocatalytic template) and downstream to a reporting probe (which produces a specific fluorescence signal).

Figure 34:
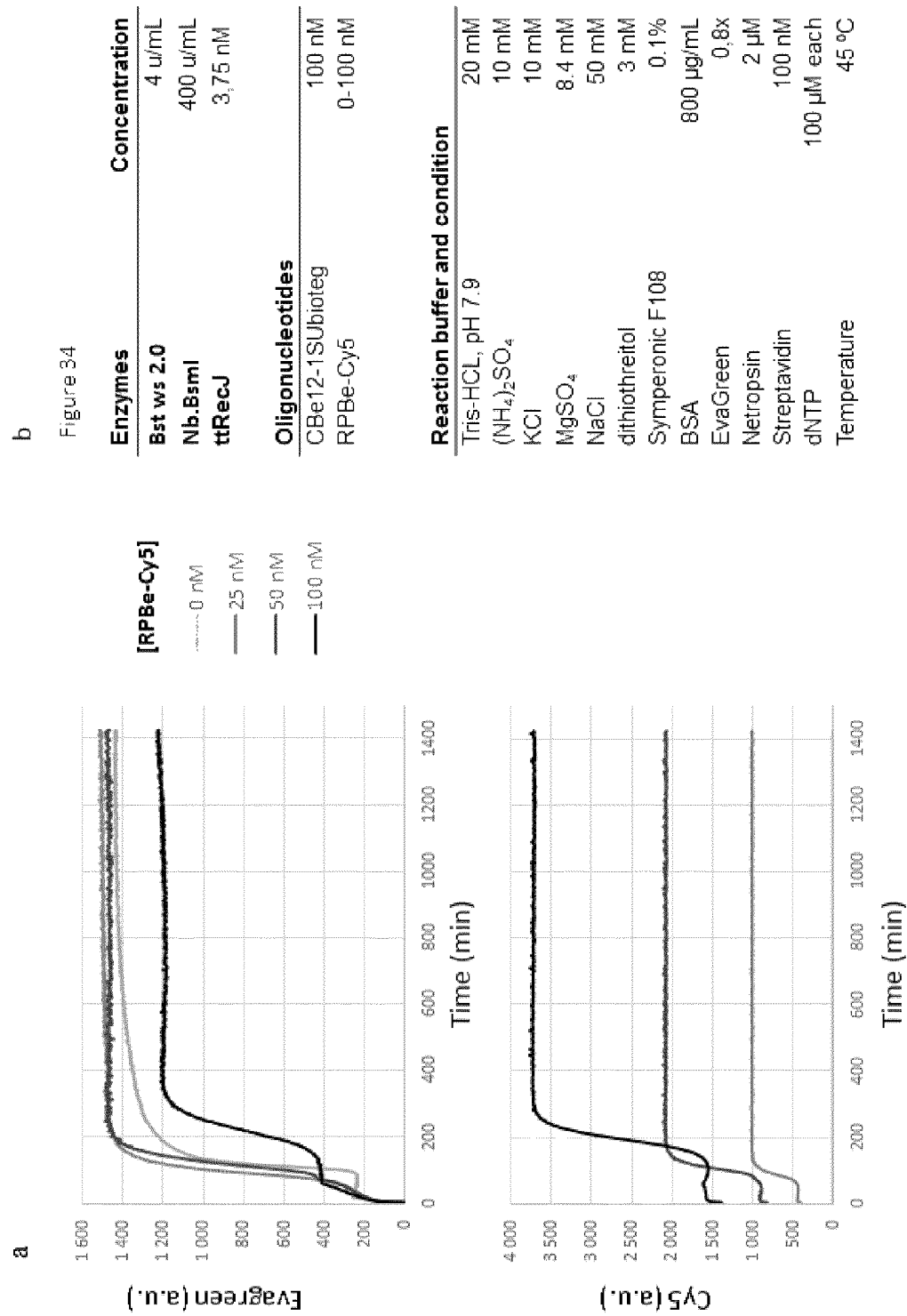
FIG. 34 is a first generation of reporting probes (rP), wherein a. shows the measurement of the specific signal (cyanine 5) and of the non-specific EvaGreen signal b. shows the experimental conditions when a signal strand produced by an autocatalyst (CBe12-1SUbioteg) with the reporter probe RPBe-Cy5 (Bioteg TTT TG DDQII CAT TCA ATT TTC GAT CCT GAA TG Cy5) is detected.

Firstly, the inventors demonstrated reporting probe generation (FIG. 34). In this experiment, they demonstrated the detection of a signal strand produced by an autocatalyst (CBe12-1S4bioteg, corresponding to the SEQ ID NO: 54) with the reporter probe RPBe-Cy5 (Bioteg TTT TG DDQII CAT TCA ATT TTC GAT CCT GAA TG Cy5, corresponding to SEQ ID NO: 58). No trigger is added in the initial condition and the autocatalysis starts after a short delay due to non-specific reaction. It was observed that the signal specific signal (cyanine 5) is correlated to the non-specific EvaGreen signal (which reports the total amount of double strands). It is to note that the signal to noise ratio is not affected by the concentration of the probe but will rather depends on the quenching efficiency, quantum yield of the fluorophore and other physico-chemical considerations.

Figure 35:
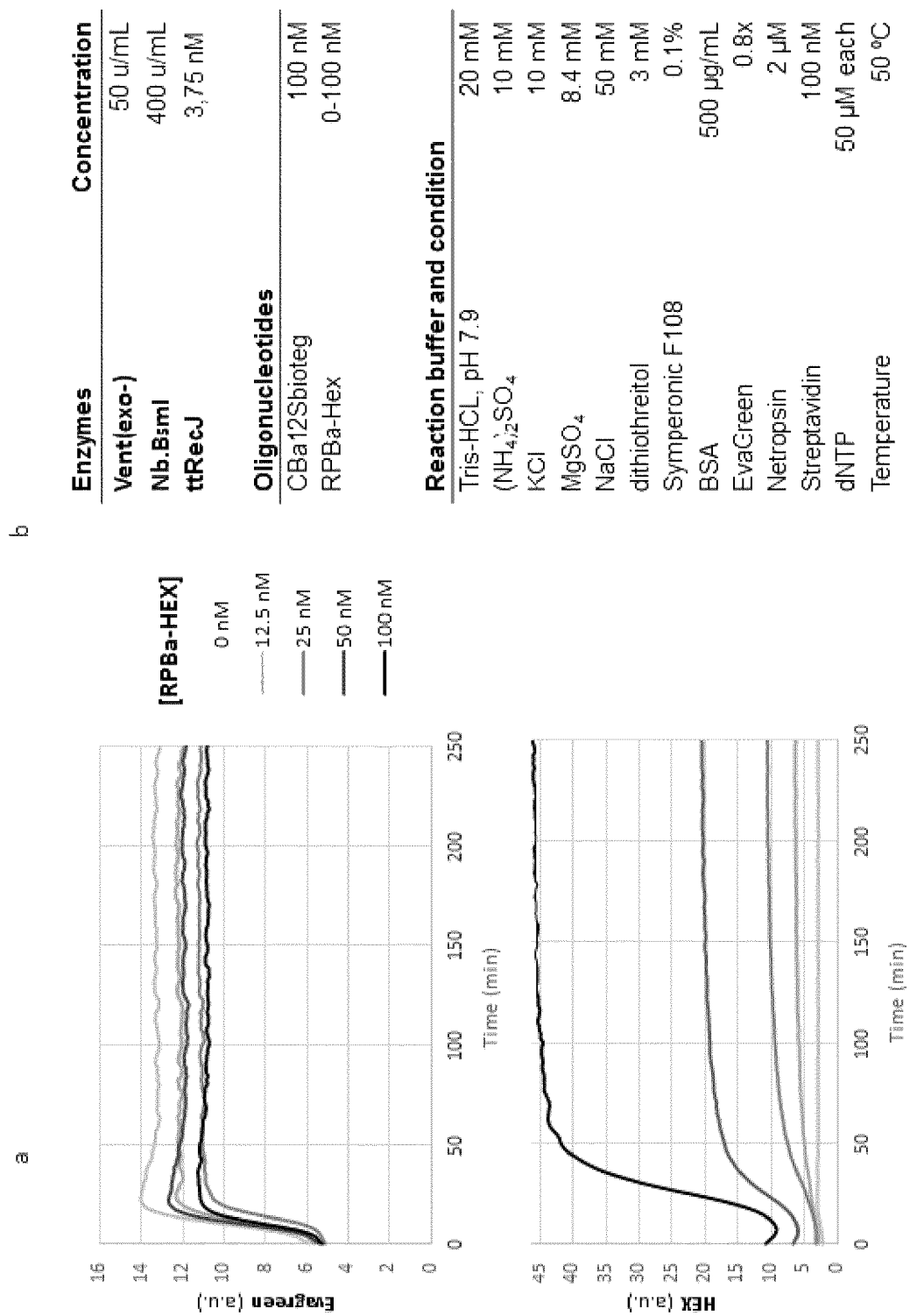
FIG. 35 a. shows the use of a second reporter probe (RPBa-Hex: Biotin TTTTG DDQII AATTCTATTTT CTC GTC AGA ATT HEX) that reports the presence of sequence Ba12 (CATTCTGACGAG), produced by the autocatalytic template CBa12PS4bioteg (Bioteg *C*T*C*GTCAGAATG-CTCGTCAGAATG-Phosp). b. Experimental conditions.

Then, the inventors designed a second reporter probe (RPBa-Hex: Biotin TTTTG DDQII AATTCTATTTT CTCGTCAGAATT HEX, corresponding to SEQ ID NO: 56) that reports the presence of the sequence Ba12 (CATTCTGACGAG, corresponding to SEQ ID NO: 8), produced by the autocatalytic template CBa12PS4bioteg (Bioteg *C*T*C*GTCAGAATG-CTCGTCAGAATG-Phosp, SEQ ID NO: 17). The amplification curves recorded both with EvaGreen (nonspecific) and Hex (specific) chromophores demonstrate the efficacy of the probe to report the production of Ba12 (FIG. 35).

Figure 36:
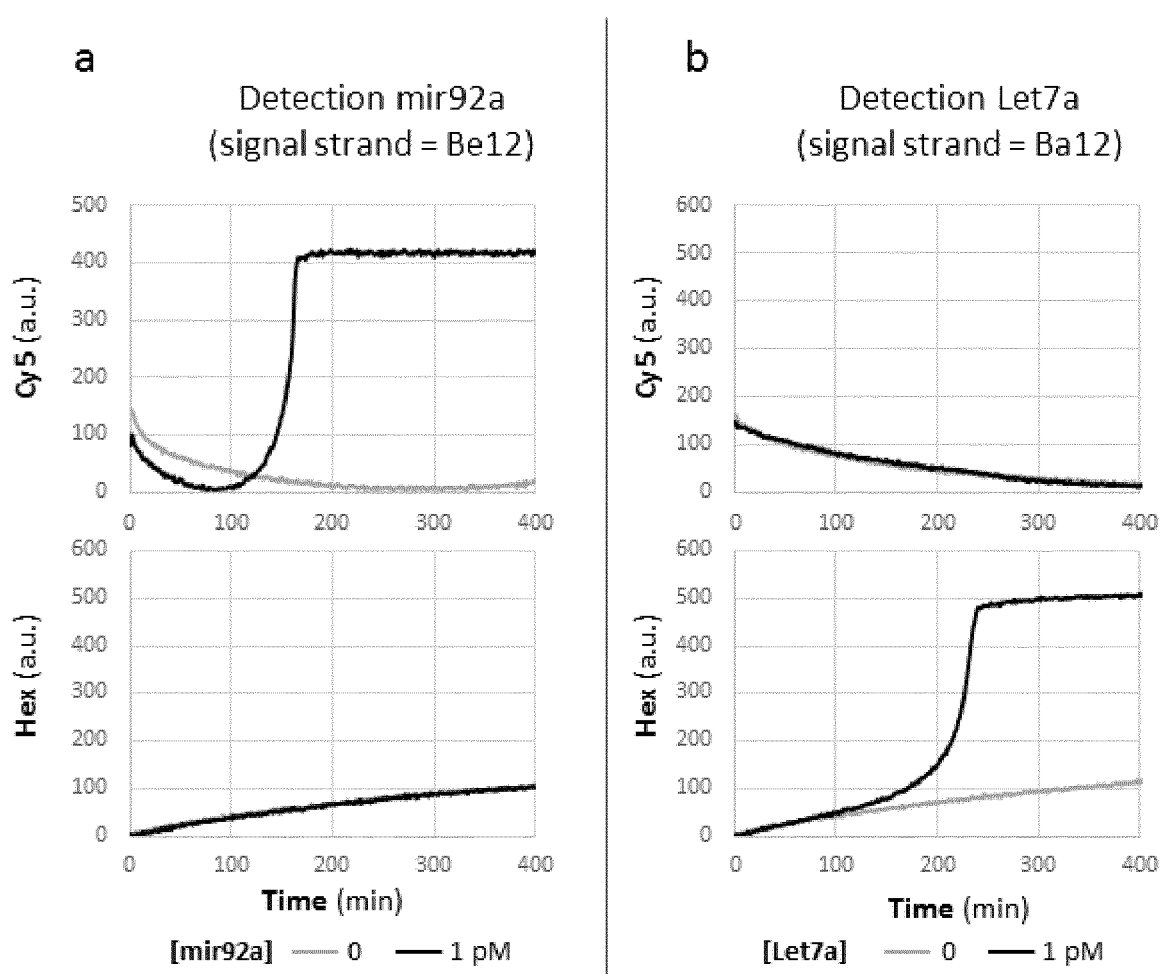
FIG. 36 is an evaluation of the specificity of reporting probe (rP). a. Detection of the sequence of mir92a b. Detection of the target Let7a. c. and d. Experimental conditions.

The specificity of the reporting probe (rP) was also assessed (FIG. 36). To that goal, two molecular programs are assembled separately: a. one for the detection the sequence of mir92a (SEQ ID NO: 28) that amplifies the signal strand Be12 (92atoF5TBe12S0P/CBe12-3noPS3/pTBe12T5SP or SEQ ID NO: 49/SEQ ID NO: 63/SEQ ID NO: 5: respectively); b. one for the detection of the target Let7a that amplifies the signal Ba12 (Let7atoF5TBa12S0P/CBa12-3noPS3/pTBa12T5SP or SEQ ID NO: 49/SEQ ID NO: 57/SEQ ID NO: 11). Each system is put in separated tube in presence of both reporter probes (RPBe-Cy5, (SEQ ID NO: 53) and RPBa-Hex (SEQ ID NO: 56), the enzymatic processor and 0 or 1 pM of the cognate target. In both cases, it was observed: i) signal amplification only in presence of the target while the negative controls do not lead to any detectable positive signal and ii) the specific reporting of both reporter probes: RPBe-Cy5 and RPBa-Hex report exclusively the presence of Be12 (triggered by the presence of mir92a) and Ba12 (triggered by the presence of Let7a), respectively.

Figure 37:
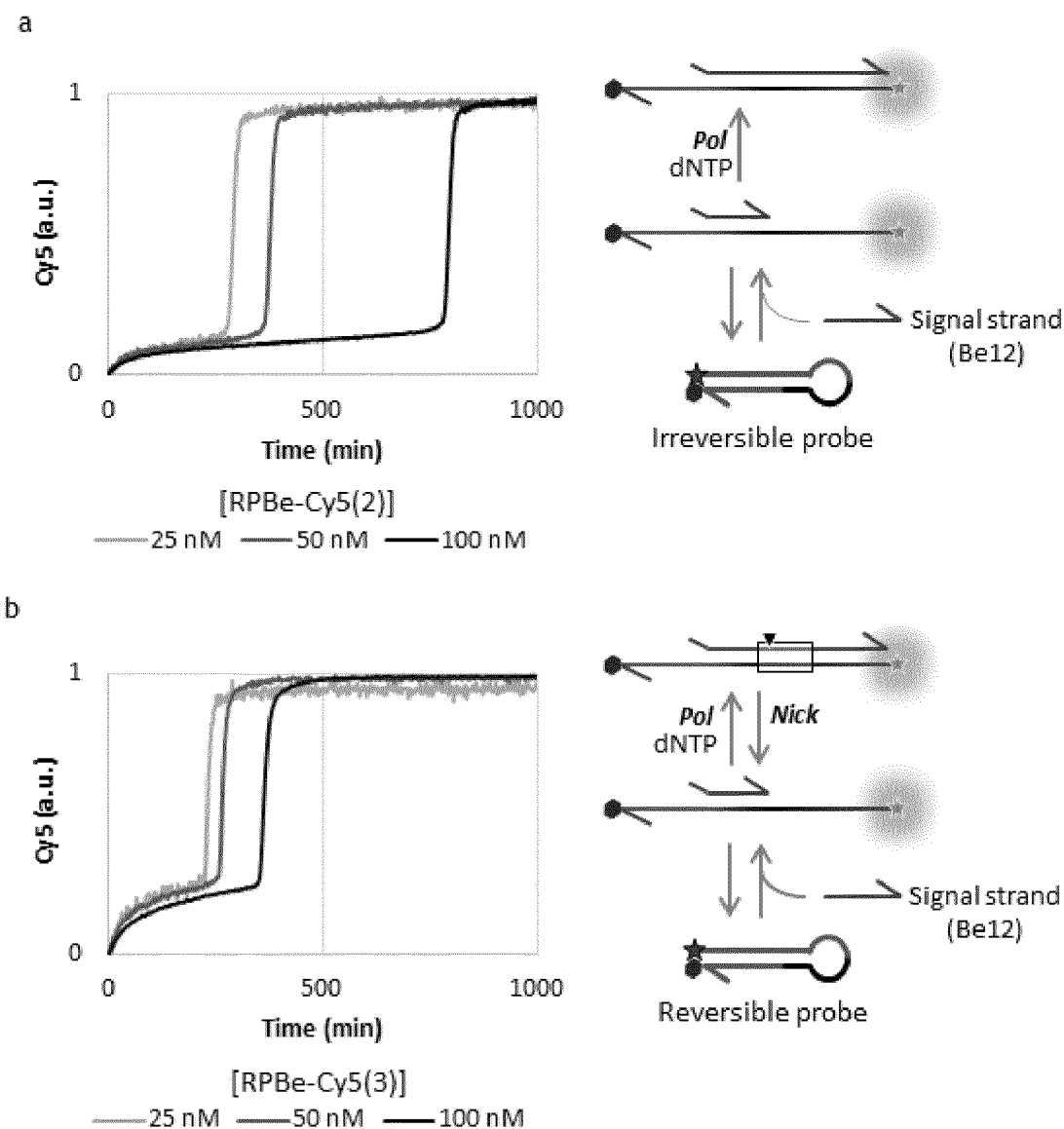
FIG. 37 shows irreversible vs reversible reporting strategy. a. Irreversible reporting strategy. b. Reversible reporting strategy. c. Experimental conditions.

In further development, the inventors compared two types of reporting strategy, irreversible and reversible reporting strategy. The obtained results are shown in FIG. 37.

In the previous design the signal strands are irreversibly captured by the probe by polymerization (formation of a stable duplex shown in FIG. 37a).

In another preferred development according to the invention, the probe are designed to exhibit the nicking recognition site after the signal strand is polymerized. As a result, the duplex can be cut by the nicking enzyme (e.g. Nb. BsmI) leading to the dynamical reversible reporting strategy.

The obtained results show that a non-nickable probe consumes signal strands and acts thereby as a noncatalytic pseudo-template. Therefore, it was observed a significant delay in the amplification. On the contrary, a reversible probe consumes only transiently the signal strands that are regenerated by nicking. Consequently, the delay in the amplification is much less important.

In Example 11 below, the inventors demonstrated that a mechanism called "Recovery mechanism" avoiding both enzymes sequestration and signal production by one node that may affect negatively another node in multiplex detection assay wherein orthogonal programs running independently use the same catalytic resources. The strategy developed by the inventors consists in the transitory activation of each node instead of constitutive production of signal strands. To that goal, a restriction enzyme is added to enzymatic processor.

Figure 38:
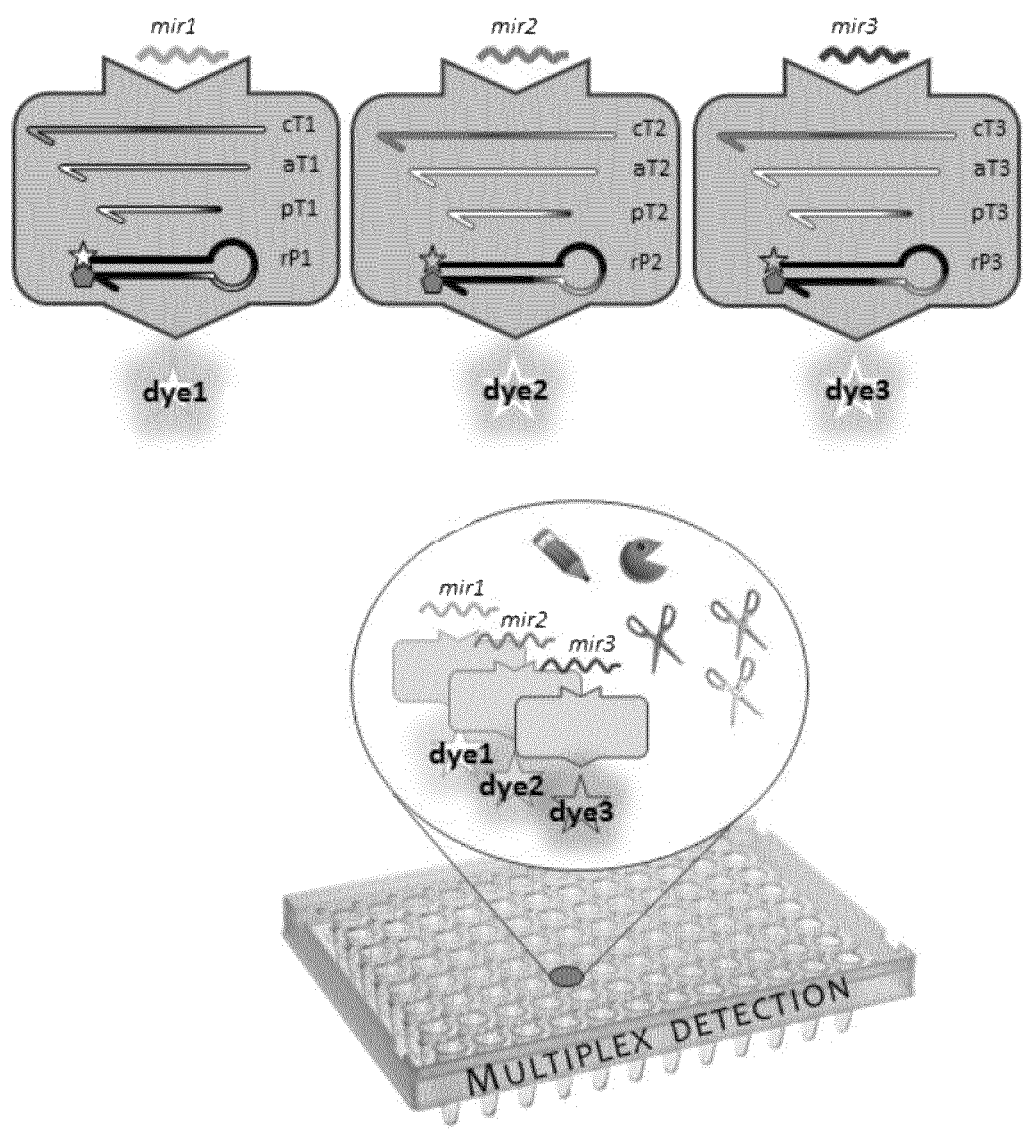
FIG. 38 shows a multiplex detection of microRNA with orthogonal DNA circuits: principle in solution.

The principle of multiplex detection of microRNA with orthogonal DNA circuits in solution is shown in FIG. 38.

Figure 39:
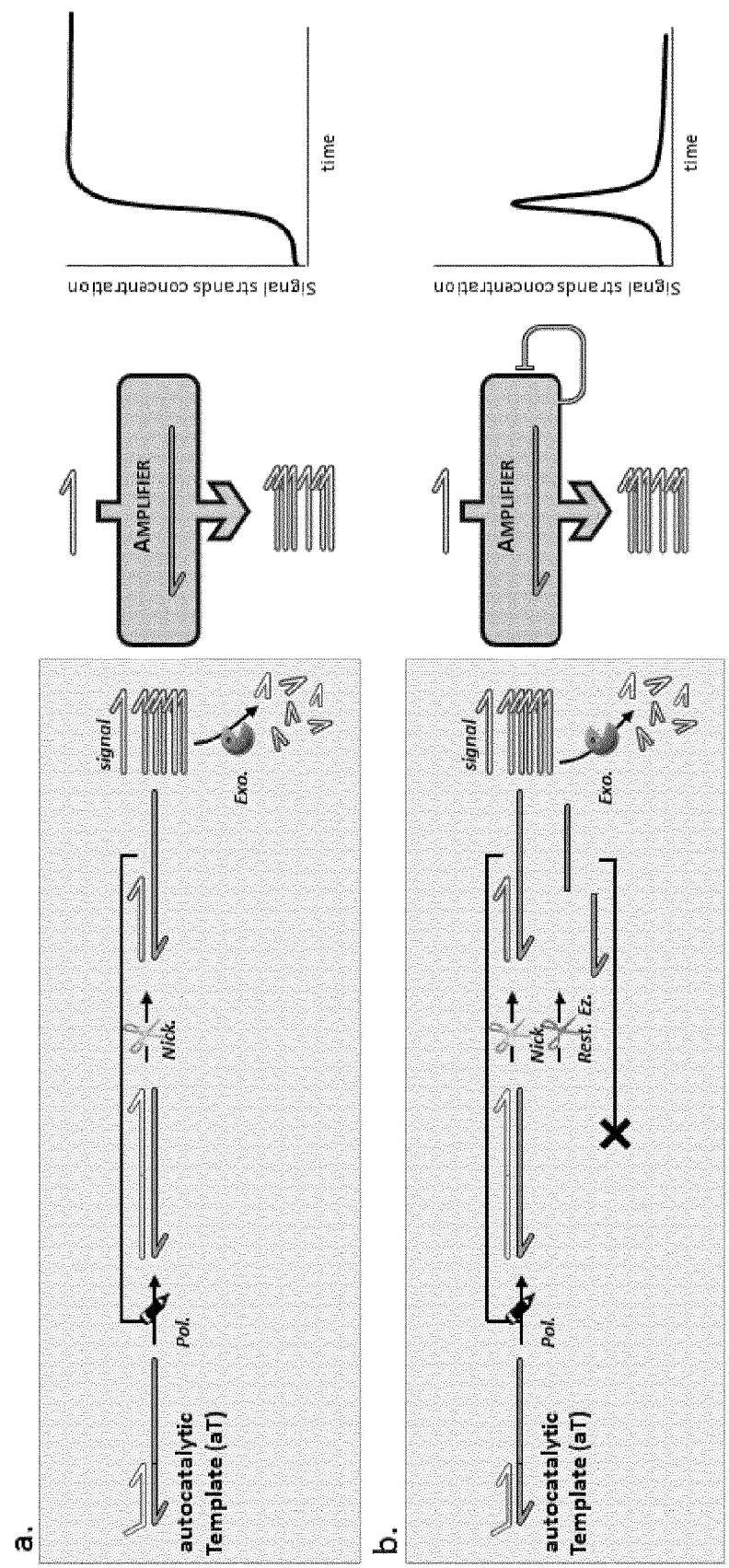
FIG. 39 shows a comparison between autocatalytic systems without or with recovery mechanism. a. Autocatalytic system without the recovery mechanism. b. Autocatalytic system with the recovery mechanism.

FIG. 39 shows the results obtained with autocatalytic system without and with recovery mechanism.

As shown in FIG. 39a, when the autocatalytic system operates without recovery mechanism, the exponential amplification loop leads to the accumulation of signal strands. In presence of the exonuclease acting as a sink, the system reaches a steady state where the concentration of signal strands plateaus (the production is balanced by the degradation).

As shown in FIG. 39b, when the autocatalytic system operates with the recovery mechanism, in addition to the nickase (Nb.BsmI), a restriction enzyme (BsmI) is added to the enzymatic processor. Both have the substrate, i.e. the double-stranded autocatalytic template. After polymerization of a trigger, the resulting duplex can be cut either by the nickases or by the restriction enzyme. Consequently, while the exponential amplification still persists, the templates are gradually degraded by the restriction enzyme, the degradation speed depending on the ratio nickases/restriction enzyme. The autocatalytic loop eventually stops and the signal strands are depolymerized by the exonuclease and do not accumulate anymore.

The transitory production of signal strand is experimentally shown in FIG. 40. The experimental conditions are shown in FIG. 40c. 100 nM of the autocatalytic template is put in presence of the enzymatic mixture. The enzymatic processor is completed with a varying amount of the restriction enzymes (BsmI, from 0 to 200 u/mL). In absence of restriction enzymes (RE), the autocatalysis in presence of the exonuclease drives the system to the steady state where the constant production of signal strands is counterbalanced by the degradation. If the RE is introduced, it progressively destroyed the active template (i.e. the template that have bound and driven the polymerization an input strand), so that the production eventually stops and the concentration of signal strands goes back to 0. The sharpness and amplitude of the transient production of signal strands depend on the ratio nickases/restriction enzyme (FIG. 40 a).

The autocatalytic template is put in presence of varying concentrations of pseudo-template which is used here to delay the self-start. The experiment shows first that the presence of the restriction enzyme does not prevent the amplification. Second, the efficiency of the recovery remains the same along time, even after 1000 minutes of incubation (FIG. 40b).

In order to prove the efficiency of the recovery mechanism the inventors measured the concentration of the amplified trigger (Be12, whose production is catalyzed by the amplifier CBe12-3noPS3 (SEQ ID NO: 43)) after amplification with a full detection system (FIG. 41a). First, two tubes containing the DNA circuit and the enzymatic machinery (polymerase, exonuclease, nickases) were triggered by 1 nM of Be12, in presence (200 u/mL) or absence of the restriction enzyme BsmI. The two duplicated samples were allowed to run for 350 minutes before the reaction is stopped (tubes were put at 4° C., FIG. 41b). An aliquot (1/100th) of these samples were then reamplified in presence of 100 nM of template Cbe12-3noPS3 and 4 nM of pseudo-template pTBe12T5SP 'SEQ ID NO: 5). The fluorescence of EvaGreen was then monitored at 50° C. to determine the Ct (amplification time), which were then compared to the Ct values obtained using a set of standard Be12 solution of known concentrations (FIG. 41d). While in absence of the restriction enzyme, a high concentration of Be12 (>20 nM) is present in the sample after 350 min, this amount is much lower if the restriction enzyme mediated the arrest of the production ([Be12] <<3 nM) (FIG. 41e).

Figure 41:
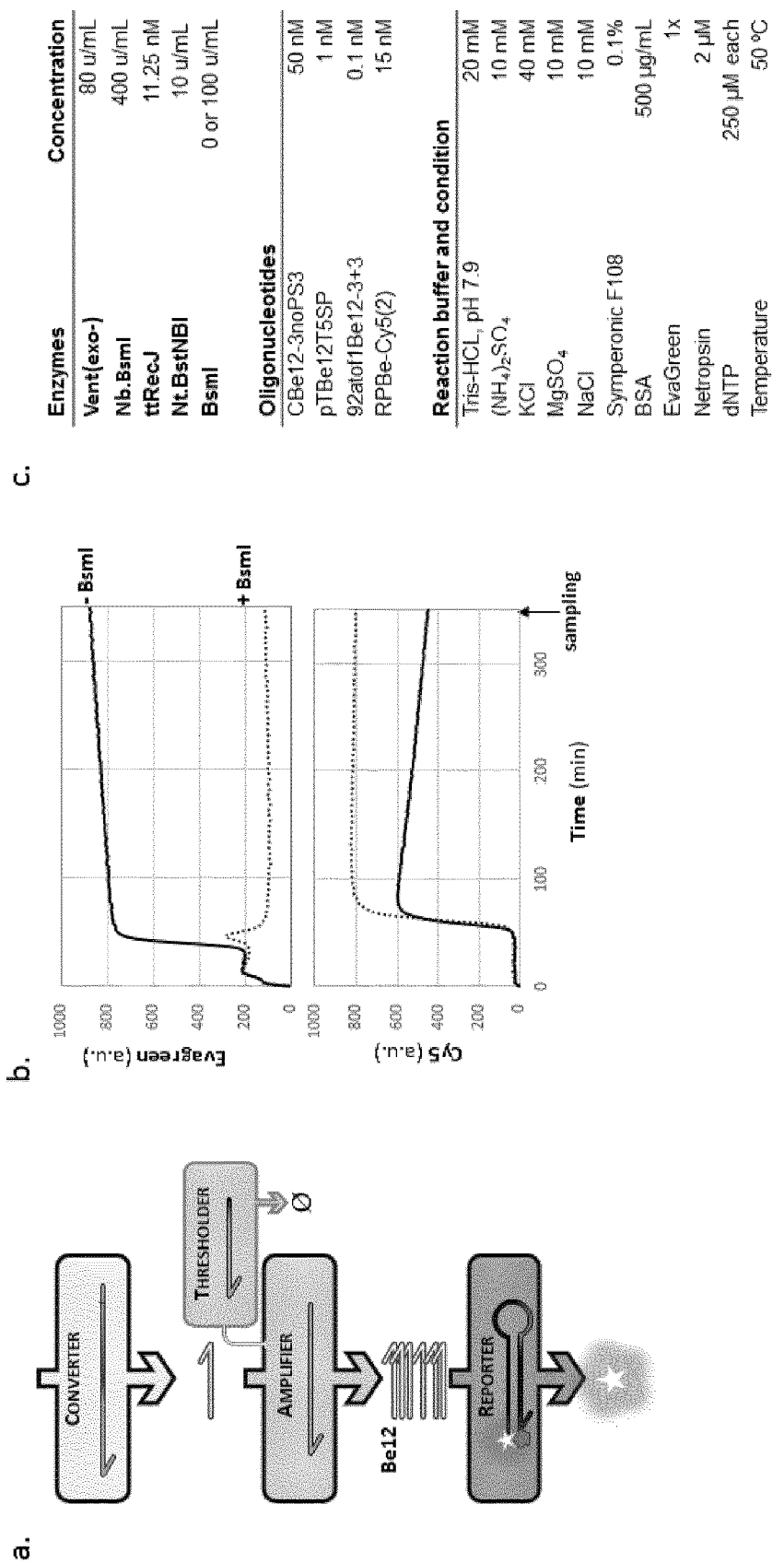
FIG. 41 shows contaminants elimination after recovery. a. Topology of the studied circuit: 4 DNA strands (converter, thresholder, amplifier and reporter templates). b. Amplification curves of two samples (with or without the restriction enzyme BsmI). c. Experimental conditions used in the panel (a and b). d. Standard calibration curve of the Ct values as a function of the initial concentration of Be12. e. An aliquot of the previous samples (with or without BsmI) f. Experimental conditions for samples and standard reamplification (panel d and e).

The obtained results show that in absence of RE, the Evagreen signal reaches a plateau (FIG. 41a). If the RE is introduced, the Evagreen signal recorded a short spike before going back to initial fluorescence state while the reporter probe retains a high fluorescence signal due to the cleavage of the probes (FIG. 41b). The reaction is stopped at 350 minutes before reamplification. The experimental conditions used in the panel are shown in FIG. 41c. FIG. 41 d is standard calibration curve of the Ct values as a function of the initial concentration of Be12. FIG. 41d shows that in presence of the restriction enzyme, the concentration of Be21 is drastically reduced in comparison to the sample without the RE (and thus that accumulated a high amount of contamination molecules). Experimental conditions for samples and standard reamplification (panel d and e are shown in FIG. 41O.

Figure 42:
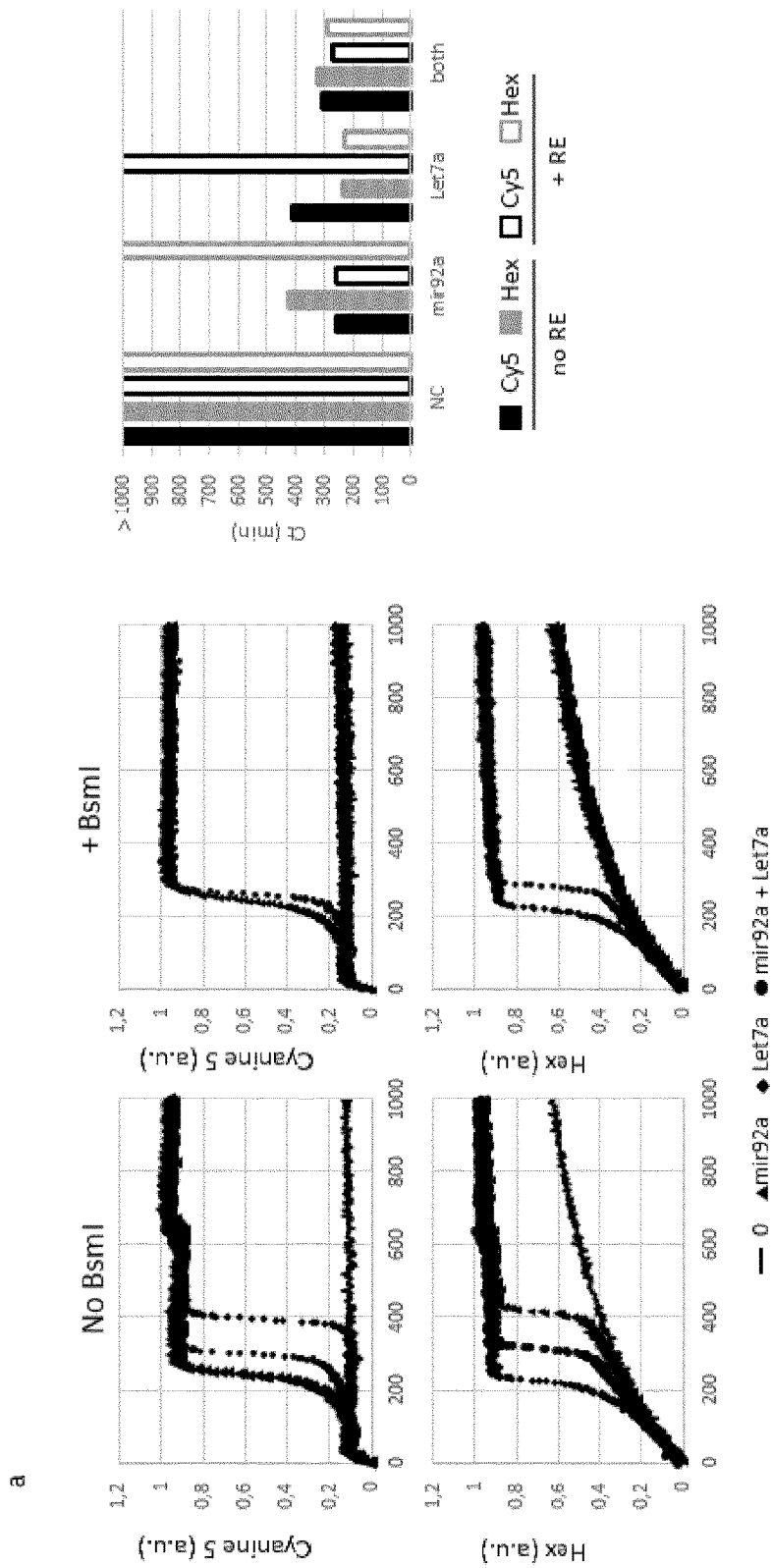
FIG. 42 shows the importance of the recovery mechanism for the duplex assay. a. Multiplex assay+/−BsmI (RE) Cbe-mir92a-Cy5 Cba-Let7a-HEX. b. Experimental conditions.

In the Example 12, the inventors investigated the feasibility of the multiplex detection of different microRNA from the same sample. To that goal, different DNA circuits have been assembled to detect the microRNAs mir92a (SEQ ID NO: 48) or Let7a (SEQ ID NO: 30). The reporting probes are functionalized with cyanine 5 and Hex, respectively. In FIG. 42, the two programs are pooled together with enzymatic processor containing or not the restriction enzymes BsmI. For each series, the sample is spiked either with no target, one of the two targets or both targets. In absence of the restriction enzyme, it is important to note that once a bistable module switches ON (triggered by the cognate target), it eventually leads to the unspecific amplification of the second bistable module (even in absence of the second target). This can be explained by the cross-talk mechanism mentioned above. If the restriction enzyme is introduced, only the corresponding bistable switch turns ON, demonstrating the efficacy and the importance of the recovery mechanism for multiplexing applications. Consequently, it was demonstrated that a decent specificity cannot be reached in absence of BsmI due to coupling mechanisms between the two programs. However, the recovery mechanism allows the decoupling of the two programs and thus the specific detection of both targets.

Figure 43:
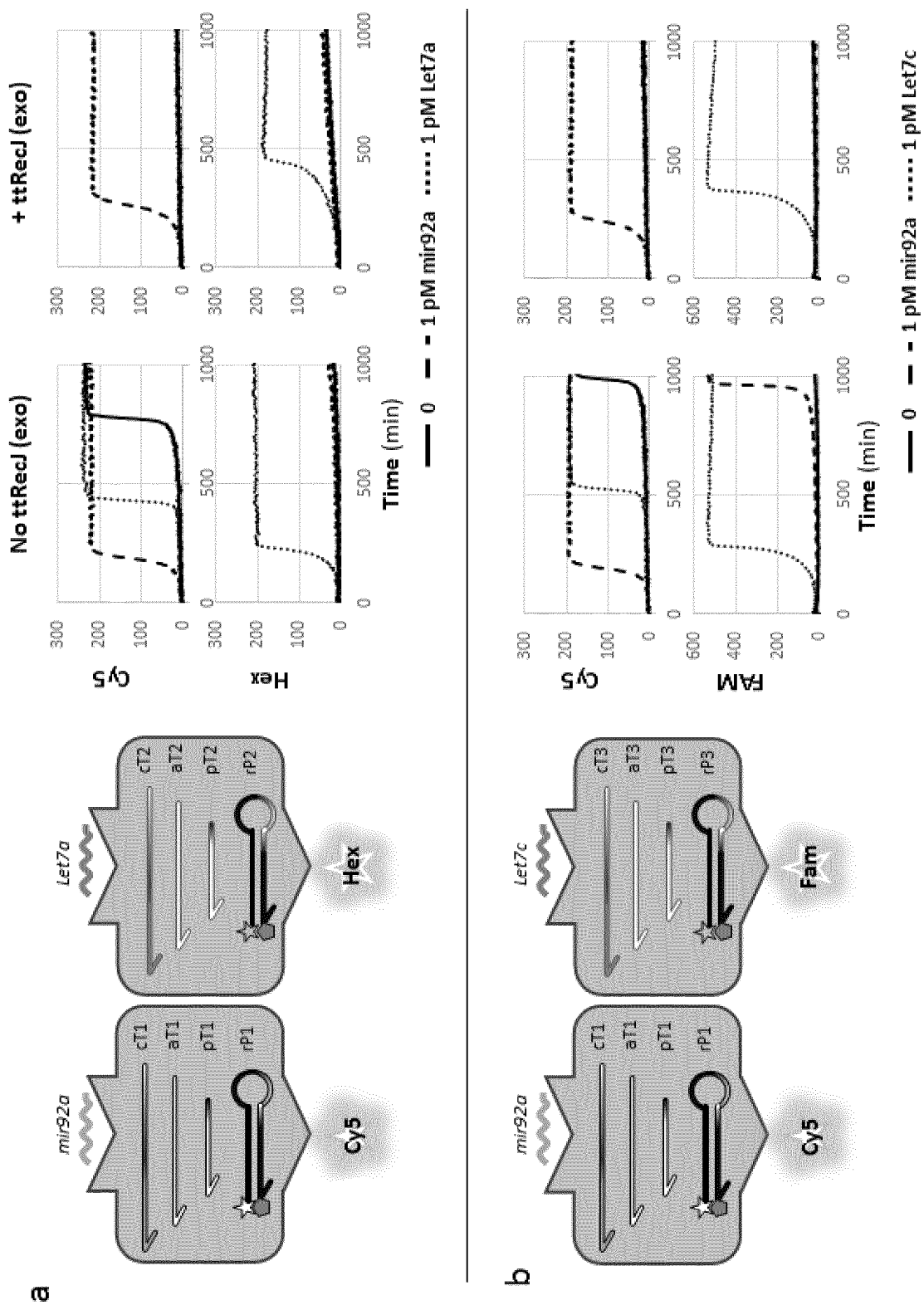
FIG. 43 shows the importance of the recovery mechanism for the duplex assay. a. Duplex detection of mir92a and Let7a. b. Duplex detection of mir92a and Let7c. c. Experimental conditions.

Using the same assay, the inventors further demonstrated the importance of the exonuclease for the multiplex detection using this assay based on isothermal exponential amplification of the signal. Two independent DNA circuits are used to assess to presence of two targets from the same sample: 1) duplex detection of mir92a (SEQ ID NO: 48) and Let7a 'SEQ ID NO: 30) (FIGS. 43a and 2) duplex detection of mir92a (SEQ ID NO: 48) and Let7c (SEQ ID NO: 32) (FIG. 43b). The experimental conditions of this assay are shown in FIG. 43 c.

FIG. 43 shows that in absence of the exonuclease, the amplification of one node leads to the accumulation of signal strands that interfere with the second node and eventually drive its amplification. In presence of the exonuclease, the signal strands are destroyed once the amplification is stopped by the recovery mechanism. Acting as a sink, the exonuclease regulates the amplification and brings the concentration of signal strands down to 0. This transient and sharp production of signal strands is enough to light on the reporter probe but not enough to interfere with the second node, safeguarding the independence of the DNA circuits. Therefore, the inventors demonstrated here the specific detection of two targets using two DNA circuits pooled in the same sample.

As described above, in the present embodiment, a new way to reduce and eliminate the background signal in isothermal amplification is proposed. The principle is to ensure that the amplification rate is decreased and possibly negative at low concentration of trigger, so that the low state becomes stable, but is still fast at higher concentrations of trigger, so that it amplification happens following a finite perturbation. This is obtained by using the continuous deactivation process that is fast but saturable. The design described herein uses (1) a modified amplification template, (2) a small concentration of deactivating pseudo-template, and (3) a mixture of polymerizing and depolymerizing enzymes guarantees that the DNA system will not initiate amplification unless a given and adjustable threshold is crossed. This threshold can be set arbitrarily low for ultrasensitive detection and also provides high specificity and multiplexing capabilities. More generally, this approach can be used to insert activation thresholds and non-linearities in enzymatic DNA-programmed circuits. The present description also demonstrates that the method of eliminating background amplification according to the invention may be efficiently used in multiplex detection method, particularly for microRNA detection. The addition of reporting probes into another templates used in the method of the invention and the use of the recovery mechanism described above allow obtaining rapid, specific and less expensive detection The disclosure in this Description is not limited to the above embodiment, but may be diversely modified and varied. Thus, the modifications and variations are not excluded from the scope of protection of the Claim(s) attached hereto.

INDUSTRIAL APPLICABILITY

The present invention is applicable to a general method of eliminating background amplification in isothermal DNA amplification, and obtaining robust multiplexed, ultra-specific and ultrasensitive detection of various nucleic acid targets.

The invention claimed is:

1. A method of isothermal amplification of a nucleic acid target sequence to obtain an amplified sequence, the method comprising:
   (a) obtaining a mixture of:
      (i) buffer comprising a polymerase, nicking enzyme and exonuclease,
      (ii) a first oligonucleotide which is an amplification oligonucleotide having a nucleic acid sequence between 10 and 40 nucleotides, wherein the sequence includes a partial repeat structure containing a nicking enzyme recognition site,
      (iii) a second oligonucleotide which is a leak absorption oligonucleotide having a nucleic acid sequence between 10 and 35 nucleotides, a 3' end that is complementary to the amplified sequence, and a 5' end that encodes a sequence of a tail which is appended to the amplified sequence, the sequence of the tail having a length between 2 and 6 nucleotides and being different from the amplified sequence, and
      (iv) a third oligonucleotide which is a target-specific conversion oligonucleotide having a 3' end that is complementary to the nucleic acid target sequence and a 5' end at least partially complementary to 3' end of the amplification oligonucleotide;
   (b) adding the mixture of (a) to a sample to be analyzed;
   (c) incubating the sample at constant temperature; and
   (d) detecting the nucleic acid target sequence through amplification of the amplified sequence, while eliminating background amplification by the leak absorption oligonucleotide.

2. The method according to claim 1, wherein the first oligonucleotide is able to bind and exponentially amplify the amplified sequence and the second oligonucleotide is able to bind, extend, deactivate and release the products of polymerization along the first oligonucleotide, thereby inducing a threshold, which corresponds to a minimal concentration of the amplified sequence under which the amplification reaction is repressed and above which it is activated.

3. The method according to claim 1, wherein a 3' end of the third oligonucleotide binds to a target sequence to obtain, upon polymerization and nicking, a sequence able to activate the first oligonucleotide above the threshold adjusted by controlling concentration of the second oligonucleotide.

4. The method according to claim 1, wherein the polymerase and the nicking enzyme can drive the isothermal amplification and the exonuclease can avoid saturation of the system.

5. The method according to claim 1, wherein amplification is initiated only when a mixture of enzymes and oligonucleotides receives stimulation above a predetermined threshold.

6. The method according to claim 2, wherein the threshold is adjusted by controlling a concentration of the second oligonucleotide.

7. The method according to claim 1, wherein a 3' end of the first oligonucleotide has a reduced affinity for an amplified sequence, in comparison to the 5' end output part of the first oligonucleotide and to the binding part of the second leak-absorption oligonucleotide.

8. The method according to claim 2, wherein a 3' end of the second oligonucleotide is complementary to the sequence amplified by the first oligonucleotide, and a 5' end of the second oligonucleotide serves as a template for the polymerase to add a nucleotide sequence at the 3' end of the amplified sequence.

9. The method according to claim 6, wherein concentrations of the first and second oligonucleotides are selected so that a reaction of the first oligonucleotide is faster than a reaction of the second oligonucleotide at suprathreshold concentration of the amplified sequence but the reaction on the second oligonucleotide is faster than the reaction of the first oligonucleotide at subthreshold concentration of the amplified sequence, wherein the threshold is between 10 aM and 20 nM, thereby eliminating amplification unless the stimulus threshold is crossed.

10. The method according to claim 1, wherein the target sequence is an RNA or DNA strand of known sequence, which can be used as a biomarker.

11. The method according to claim 10, wherein multiple target sequences are simultaneously detected within the same sample using multiple sets of the first, the second and the third oligonucleotide with orthogonal sequences able to detect and report independently their specific targets.

12. The method according to claim 1, wherein the method further comprises adding a fourth oligonucleotide which is a reporting probe.

13. The method according to claim 12, wherein the reporting probe is a fluorescent probe.

14. The method according to claim 12, wherein the reporting probe detects the amplified sequences amplified by the amplification oligonucleotide.

15. The method according to claim 12, wherein the reporting probe is a single strand with a self-complementary structure modified at both ends by a fluorophore and/or a quencher.

16. The method according to claim 12, wherein the reporting probe comprises a loop which includes a nicking recognition site.

17. The method according to claim 1, wherein the amplification oligonucleotide contains a recognition site of a restriction enzyme.

18. The method according to claim 17, wherein the degradation speed of the double strand amplification template is controlled by varying the ratio nickase/restriction enzyme.

19. The method according to claim 17, wherein a restriction enzyme is added.

20. The method according to claim 19, wherein a restriction enzyme is added with an exonuclease.

* * * * *

SEQUENCE LISTING

```
<160> NUMBER OF SEQ ID NOS: 64

<210> SEQ ID NO 1
<211> LENGTH: 24
<212> TYPE: DNA
<213> ORGANISM: artificial
<220> FEATURE:
<223> OTHER INFORMATION: CBe12PS3: template having 3'phosphate
      modification and and phosphorothioate backbone modification
```

<400> SEQUENCE: 1
cgatcctgaa tgcgatcctg aatg                                      24

<210> SEQ ID NO 2
<211> LENGTH: 23
<212> TYPE: DNA
<213> ORGANISM: artificial
<220> FEATURE:
<223> OTHER INFORMATION: CBe12-1PS3: template having 3'phosphate
      modification and and phosphorothioate backbone modification

<400> SEQUENCE: 2
cgatcctgaa tgcgatcctg aat                                       23

<210> SEQ ID NO 3
<211> LENGTH: 22
<212> TYPE: DNA
<213> ORGANISM: artificial
<220> FEATURE:
<223> OTHER INFORMATION: CBe12-2PS3: template having 3'phosphate
      modification and and phosphorothioate backbone modification

<400> SEQUENCE: 3
cgatcctgaa tgcgatcctg aa                                        22

<210> SEQ ID NO 4
<211> LENGTH: 12
<212> TYPE: DNA
<213> ORGANISM: artificial
<220> FEATURE:
<223> OTHER INFORMATION: Be12

<400> SEQUENCE: 4
cattcaggat cg                                                   12

<210> SEQ ID NO 5
<211> LENGTH: 17
<212> TYPE: DNA
<213> ORGANISM: artificial
<220> FEATURE:
<223> OTHER INFORMATION: ptBe12T5SP:pseudo- template having 3'phosphate
      modification and and phosphorothioate backbone modification

<400> SEQUENCE: 5
tttttcgatc ctgaatg                                              17

<210> SEQ ID NO 6
<211> LENGTH: 12
<212> TYPE: DNA
<213> ORGANISM: artificial
<220> FEATURE:
<223> OTHER INFORMATION: decoy1: decoy binder having 3'phosphate
      modification and and phosphorothioate backbone modification

<400> SEQUENCE: 6
ctcgtcagaa tg                                                   12

<210> SEQ ID NO 7
<211> LENGTH: 13
<212> TYPE: DNA
<213> ORGANISM: artificial
<220> FEATURE:
<223> OTHER INFORMATION: decoy2: decoy binder having 3'phosphate
      modification and and phosphorothioate backbone modification -continued

```
<400> SEQUENCE: 7
ctcgtcagaa tga                                                           13

<210> SEQ ID NO 8
<211> LENGTH: 12
<212> TYPE: DNA
<213> ORGANISM: artificial
<220> FEATURE:
<223> OTHER INFORMATION: Ba12

<400> SEQUENCE: 8
cattctgacg ag                                                            12

<210> SEQ ID NO 9
<211> LENGTH: 23
<212> TYPE: DNA
<213> ORGANISM: artificial
<220> FEATURE:
<223> OTHER INFORMATION: CBa12-1PS4: amplification template having
      3'phosphate modification and and phosphorothioate backbone
      modification

<400> SEQUENCE: 9
ctcgtcagaa tgctcgtcag aat                                                23

<210> SEQ ID NO 10
<211> LENGTH: 16
<212> TYPE: DNA
<213> ORGANISM: artificial
<220> FEATURE:
<223> OTHER INFORMATION: ptBa12A4SP: pseudo-template having 3'phosphate
      modification and and phosphorothioate backbone modification

<400> SEQUENCE: 10
aaaactcgtc agaatg                                                        16

<210> SEQ ID NO 11
<211> LENGTH: 17
<212> TYPE: DNA
<213> ORGANISM: artificial
<220> FEATURE:
<223> OTHER INFORMATION: ptBa12T5SP: pseudo-template having 3'phosphate
      modification and and phosphorothioate backbone modification

<400> SEQUENCE: 11
tttttctcgt cagaatg                                                       17

<210> SEQ ID NO 12
<211> LENGTH: 16
<212> TYPE: DNA
<213> ORGANISM: artificial
<220> FEATURE:
<223> OTHER INFORMATION: ptBa12T4S3P: pseudo-template having 3'phosphate
      modification and and phosphorothioate backbone modification

<400> SEQUENCE: 12
ttttctcgtc agaatg                                                        16

<210> SEQ ID NO 13
<211> LENGTH: 15
<212> TYPE: DNA
<213> ORGANISM: artificial
<220> FEATURE:
<223> OTHER INFORMATION: ptBa12T3S3P: pseudo-template having 3'phosphate
      modification and and phosphorothioate backbone modification
```

```
<400> SEQUENCE: 13
tttctcgtca gaatg                                                   15

<210> SEQ ID NO 14
<211> LENGTH: 14
<212> TYPE: DNA
<213> ORGANISM: artificial
<220> FEATURE:
<223> OTHER INFORMATION: ptBa12T2S3P: pseudo-template having 3'phosphate
      modification and and phosphorothioate backbone modification

<400> SEQUENCE: 14
ttctcgtcag aatg                                                    14

<210> SEQ ID NO 15
<211> LENGTH: 13
<212> TYPE: DNA
<213> ORGANISM: artificial
<220> FEATURE:
<223> OTHER INFORMATION: ptBa12T1S3P: pseudo-template having 3'phosphate
      modification and and phosphorothioate backbone modification

<400> SEQUENCE: 15
tctcgtcaga atg                                                     13

<210> SEQ ID NO 16
<211> LENGTH: 22
<212> TYPE: DNA
<213> ORGANISM: artificial
<220> FEATURE:
<223> OTHER INFORMATION: CBa12-2PS4: amplification template having
      3'phosphate modification and and phosphorothioate backbone
      modification

<400> SEQUENCE: 16
ctcgtcagaa tgctcgtcag aa                                           22

<210> SEQ ID NO 17
<211> LENGTH: 24
<212> TYPE: DNA
<213> ORGANISM: artificial
<220> FEATURE:
<223> OTHER INFORMATION: CBa12PS4: template having 3'phosphate
      modification and and phosphorothioate backbone modification

<400> SEQUENCE: 17
ctcgtcagaa tgctcgtcag aatg                                         24

<210> SEQ ID NO 18
<211> LENGTH: 23
<212> TYPE: DNA
<213> ORGANISM: artificial
<220> FEATURE:
<223> OTHER INFORMATION: CBa12-1PS4: template having 3'phosphate
      modification and and phosphorothioate backbone modification

<400> SEQUENCE: 18
ctcgtcagaa tgctcgtcag aat                                          23

<210> SEQ ID NO 19
<211> LENGTH: 21
<212> TYPE: DNA
<213> ORGANISM: artificial
<220> FEATURE:
<223> OTHER INFORMATION: CBa12-3PS4: template having 3'phosphate
      modification and and phosphorothioate backbone modification
```

```
<400> SEQUENCE: 19
ctcgtcagaa tgctcgtcag a                                              21

<210> SEQ ID NO 20
<211> LENGTH: 17
<212> TYPE: DNA
<213> ORGANISM: artificial
<220> FEATURE:
<223> OTHER INFORMATION: pTk12T5S4P: draind1-8pseudo-template

<400> SEQUENCE: 20
tttttcaatg acucctg                                                   17

<210> SEQ ID NO 21
<211> LENGTH: 14
<212> TYPE: DNA
<213> ORGANISM: artificial
<220> FEATURE:
<223> OTHER INFORMATION: ApTk12A1SUP: draind1-8pseudo-template

<400> SEQUENCE: 21
acaatgacuc ctga                                                      14

<210> SEQ ID NO 22
<211> LENGTH: 15
<212> TYPE: DNA
<213> ORGANISM: artificial
<220> FEATURE:
<223> OTHER INFORMATION: ApTk12A2SUP: draind1-8pseudo-template

<400> SEQUENCE: 22
aacaatgacu cctga                                                     15

<210> SEQ ID NO 23
<211> LENGTH: 16
<212> TYPE: DNA
<213> ORGANISM: artificial
<220> FEATURE:
<223> OTHER INFORMATION: ApTk12A3PS: draind1-8pseudo-template

<400> SEQUENCE: 23
aaacaatgac ucctga                                                    16

<210> SEQ ID NO 24
<211> LENGTH: 16
<212> TYPE: DNA
<213> ORGANISM: artificial
<220> FEATURE:
<223> OTHER INFORMATION: ApTk12A4SUP: draind1-8pseudo-template

<400> SEQUENCE: 24
aaaacaatga ccctga                                                    16

<210> SEQ ID NO 25
<211> LENGTH: 17
<212> TYPE: DNA
<213> ORGANISM: artificial
<220> FEATURE:
<223> OTHER INFORMATION: ApTk12A5SUP: draind1-8pseudo-template

<400> SEQUENCE: 25
aaaaacaatg accctga                                                   17
```

```
<210> SEQ ID NO 26
<211> LENGTH: 18
<212> TYPE: DNA
<213> ORGANISM: artificial
<220> FEATURE:
<223> OTHER INFORMATION: ApTk12A6SUP: draind1-8pseudo-template

<400> SEQUENCE: 26
aaaaaacaat gaccctga                                                 18

<210> SEQ ID NO 27
<211> LENGTH: 22
<212> TYPE: DNA
<213> ORGANISM: artificial
<220> FEATURE:
<223> OTHER INFORMATION: D21DNA: DNA strand corresponding to miR-21

<400> SEQUENCE: 27
tagcttatca gactgatgtt ga                                            22

<210> SEQ ID NO 28
<211> LENGTH: 22
<212> TYPE: RNA
<213> ORGANISM: artificial
<220> FEATURE:
<223> OTHER INFORMATION: synthetic oligoribonucleotide miR-21

<400> SEQUENCE: 28
uagcuuauca gacugauguu ga                                            22

<210> SEQ ID NO 29
<211> LENGTH: 12
<212> TYPE: DNA
<213> ORGANISM: artificial
<220> FEATURE:
<223> OTHER INFORMATION: Bc12

<400> SEQUENCE: 29
cattctggac tg                                                       12

<210> SEQ ID NO 30
<211> LENGTH: 22
<212> TYPE: RNA
<213> ORGANISM: artificial
<220> FEATURE:
<223> OTHER INFORMATION: Let7a

<400> SEQUENCE: 30
ugagguagua gguuguauag uu                                            22

<210> SEQ ID NO 31
<211> LENGTH: 22
<212> TYPE: RNA
<213> ORGANISM: artificial
<220> FEATURE:
<223> OTHER INFORMATION: Let7b

<400> SEQUENCE: 31
ugagguagua gguugugugg uu                                            22

<210> SEQ ID NO 32
<211> LENGTH: 22
<212> TYPE: RNA
<213> ORGANISM: artificial
<220> FEATURE:
<223> OTHER INFORMATION: Let7c
```

-continued

```
<400> SEQUENCE: 32
ugagguagua gguuguaugg uu                                              22

<210> SEQ ID NO 33
<211> LENGTH: 22
<212> TYPE: DNA
<213> ORGANISM: Artificial Sequence
<220> FEATURE:
<223> OTHER INFORMATION: Ck12-2PS4bioteg

<400> SEQUENCE: 33
caatgacucc tgcaatgact cc                                              22

<210> SEQ ID NO 34
<211> LENGTH: 22
<212> TYPE: DNA
<213> ORGANISM: Artificial Sequence
<220> FEATURE:
<223> OTHER INFORMATION: Cba12-2biot3

<400> SEQUENCE: 34
ctcgtcagaa tgctcgtcag aa                                              22

<210> SEQ ID NO 35
<211> LENGTH: 17
<212> TYPE: DNA
<213> ORGANISM: Artificial Sequence
<220> FEATURE:
<223> OTHER INFORMATION: ptBa12A5SP

<400> SEQUENCE: 35
aaaaactcgt cagaatg                                                    17

<210> SEQ ID NO 36
<211> LENGTH: 22
<212> TYPE: DNA
<213> ORGANISM: Artificial Sequence
<220> FEATURE:
<223> OTHER INFORMATION: Cbe12-2S4P

<400> SEQUENCE: 36
cgatcctgaa tgcgatcctg aa                                              22

<210> SEQ ID NO 37
<211> LENGTH: 16
<212> TYPE: DNA
<213> ORGANISM: Artificial Sequence
<220> FEATURE:
<223> OTHER INFORMATION: ApTBe12A3S3P

<400> SEQUENCE: 37
aaacgatcct gaatga                                                     16

<210> SEQ ID NO 38
<211> LENGTH: 22
<212> TYPE: DNA
<213> ORGANISM: Artificial Sequence
<220> FEATURE:
<223> OTHER INFORMATION: CBe12-2noPS3

<400> SEQUENCE: 38
cgatcctgaa tgcgatcctg aa                                              22
```

```
<210> SEQ ID NO 39
<211> LENGTH: 22
<212> TYPE: DNA
<213> ORGANISM: Artificial Sequence
<220> FEATURE:
<223> OTHER INFORMATION: Ck12-2S4noUbioteg

<400> SEQUENCE: 39
caatgacucc tgcaatgact cc                                              22

<210> SEQ ID NO 40
<211> LENGTH: 18
<212> TYPE: DNA
<213> ORGANISM: Artificial Sequence
<220> FEATURE:
<223> OTHER INFORMATION: ApTk12A5S3P

<400> SEQUENCE: 40
aaaaacaatg acucctga                                                   18

<210> SEQ ID NO 41
<211> LENGTH: 21
<212> TYPE: DNA
<213> ORGANISM: Artificial Sequence
<220> FEATURE:
<223> OTHER INFORMATION: CBe12-2AULP

<400> SEQUENCE: 41
cgatcctgaa tgcgatcctg a                                               21

<210> SEQ ID NO 42
<211> LENGTH: 48
<212> TYPE: DNA
<213> ORGANISM: Artificial Sequence
<220> FEATURE:
<223> OTHER INFORMATION: D21tof5TBe12S3P

<400> SEQUENCE: 42
cgatcctgaa agcgaagttt gactcatcaa catcagtctg ataagcta                  48

<210> SEQ ID NO 43
<211> LENGTH: 21
<212> TYPE: DNA
<213> ORGANISM: Artificial Sequence
<220> FEATURE:
<223> OTHER INFORMATION: CBe12-3noPS3

<400> SEQUENCE: 43
cgatcctgaa tgcgatcctg a                                               21

<210> SEQ ID NO 44
<211> LENGTH: 34
<212> TYPE: DNA
<213> ORGANISM: Artificial Sequence
<220> FEATURE:
<223> OTHER INFORMATION: D21tofBe12S0P

<400> SEQUENCE: 44
cgatcctgaa tgtcaacatc agtctgataa gcta                                 34

<210> SEQ ID NO 45
<211> LENGTH: 26
<212> TYPE: DNA
<213> ORGANISM: Artificial Sequence
<220> FEATURE:
<223> OTHER INFORMATION: CBe12-2SPCy355
```

```
<400> SEQUENCE: 45
cgatcctgaa tgcgatccat cctgaa                                          26

<210> SEQ ID NO 46
<211> LENGTH: 22
<212> TYPE: DNA
<213> ORGANISM: Artificial Sequence
<220> FEATURE:
<223> OTHER INFORMATION: CBc12SPBMN35

<400> SEQUENCE: 46
cagtccagaa tgcagtccag aa                                              22

<210> SEQ ID NO 47
<211> LENGTH: 17
<212> TYPE: DNA
<213> ORGANISM: Artificial Sequence
<220> FEATURE:
<223> OTHER INFORMATION: pTBc12T5SP

<400> SEQUENCE: 47
tttttcagtc cagaatg                                                    17

<210> SEQ ID NO 48
<211> LENGTH: 23
<212> TYPE: RNA
<213> ORGANISM: Artificial Sequence
<220> FEATURE:
<223> OTHER INFORMATION: mir92a

<400> SEQUENCE: 48
agguugggau cgguugcaau gcu                                             23

<210> SEQ ID NO 49
<211> LENGTH: 48
<212> TYPE: DNA
<213> ORGANISM: Artificial Sequence
<220> FEATURE:
<223> OTHER INFORMATION: 92atoF5TBe12PS0

<400> SEQUENCE: 49
cgatcctgaa agcgaagttt gactcaagca ttgcaaccga tcccaacc                  48

<210> SEQ ID NO 50
<211> LENGTH: 48
<212> TYPE: DNA
<213> ORGANISM: Artificial Sequence
<220> FEATURE:
<223> OTHER INFORMATION: Let7atof5TBa12S0P

<400> SEQUENCE: 50
ctcgtcagaa agcgaagttt gactcaaact atacaaccta ctacctca                  48

<210> SEQ ID NO 51
<211> LENGTH: 30
<212> TYPE: DNA
<213> ORGANISM: Artificial Sequence
<220> FEATURE:
<223> OTHER INFORMATION: CBa12-2AULP

<400> SEQUENCE: 51
ctcgtcagaa tgctcgtcag aaagcgaagc                                      30
```

```
<210> SEQ ID NO 52
<211> LENGTH: 16
<212> TYPE: DNA
<213> ORGANISM: Artificial Sequence
<220> FEATURE:
<223> OTHER INFORMATION: ApTBa12A3S3P

<400> SEQUENCE: 52
aaactcgtca gaatga                                                       16

<210> SEQ ID NO 53
<211> LENGTH: 28
<212> TYPE: DNA
<213> ORGANISM: Artificial Sequence
<220> FEATURE:
<223> OTHER INFORMATION: RPBe-Cy6

<400> SEQUENCE: 53
ttttgcattc aattttcgat cctgaatg                                          28

<210> SEQ ID NO 54
<211> LENGTH: 23
<212> TYPE: DNA
<213> ORGANISM: Artificial Sequence
<220> FEATURE:
<223> OTHER INFORMATION: CBe12-1S4bioteg

<400> SEQUENCE: 54
cgatcctgaa tgcgatcctg aat                                               23

<210> SEQ ID NO 55
<211> LENGTH: 24
<212> TYPE: DNA
<213> ORGANISM: Artificial Sequence
<220> FEATURE:
<223> OTHER INFORMATION: Cba12Sbioteg

<400> SEQUENCE: 55
ctcgtcagaa tgctcgtcag aatg                                              24

<210> SEQ ID NO 56
<211> LENGTH: 28
<212> TYPE: DNA
<213> ORGANISM: Artificial Sequence
<220> FEATURE:
<223> OTHER INFORMATION: RPBa-Hex

<400> SEQUENCE: 56
ttttgaattc tattttctcg tcagaatt                                          28

<210> SEQ ID NO 57
<211> LENGTH: 21
<212> TYPE: DNA
<213> ORGANISM: Artificial Sequence
<220> FEATURE:
<223> OTHER INFORMATION: Cba12-3noPS3

<400> SEQUENCE: 57
ctcgtcagaa tgctcgtcag a                                                 21

<210> SEQ ID NO 58
<211> LENGTH: 20
<212> TYPE: DNA
<213> ORGANISM: Artificial Sequence
```

```
<220> FEATURE:
<223> OTHER INFORMATION: RPBe-Cy5(2)

<400> SEQUENCE: 58
ttcaggtttt cgatcctgaa                                              20

<210> SEQ ID NO 59
<211> LENGTH: 21
<212> TYPE: DNA
<213> ORGANISM: Artificial Sequence
<220> FEATURE:
<223> OTHER INFORMATION: RPBe-Cy5(3)

<400> SEQUENCE: 59
attcagaatg cgatcctgaa t                                            21

<210> SEQ ID NO 60
<211> LENGTH: 18
<212> TYPE: DNA
<213> ORGANISM: Artificial Sequence
<220> FEATURE:
<223> OTHER INFORMATION: ptBa12A6biot

<400> SEQUENCE: 60
aaaaaactcg tcagaatg                                                18

<210> SEQ ID NO 61
<211> LENGTH: 45
<212> TYPE: DNA
<213> ORGANISM: Artificial Sequence
<220> FEATURE:
<223> OTHER INFORMATION: 92atof1Be12-3+3

<400> SEQUENCE: 61
atgcgatcct gacgtttgac tcaagcattg caaccgatcc caacc                  45

<210> SEQ ID NO 62
<211> LENGTH: 45
<212> TYPE: DNA
<213> ORGANISM: Artificial Sequence
<220> FEATURE:
<223> OTHER INFORMATION: Let7atof1Ba12-3+3

<400> SEQUENCE: 62
atgctcgtca gacgtttgac tcaaactata caacctacta cctca                  45

<210> SEQ ID NO 63
<211> LENGTH: 21
<212> TYPE: DNA
<213> ORGANISM: Artificial Sequence
<220> FEATURE:
<223> OTHER INFORMATION: CBc12-3noPS3

<400> SEQUENCE: 63
cagtccagaa tgcagtccag a                                            21

<210> SEQ ID NO 64
<211> LENGTH: 20
<212> TYPE: DNA
<213> ORGANISM: Artificial Sequence
<220> FEATURE:
<223> OTHER INFORMATION: RPBc-FAM

<400> SEQUENCE: 64
ttctggtttt cagtccagaa                                              20
```